US010287622B2

(12) United States Patent
Belyaev

(10) Patent No.: US 10,287,622 B2
(45) Date of Patent: May 14, 2019

(54) PLURALITY OF TRANSPOSASE ADAPTERS FOR DNA MANIPULATIONS

(71) Applicant: Agilent Technologies, Inc., Santa Clara, CA (US)

(72) Inventor: Alexander S. Belyaev, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/035,038

(22) PCT Filed: Sep. 5, 2014

(86) PCT No.: PCT/US2014/054218
§ 371 (c)(1),
(2) Date: May 6, 2016

(87) PCT Pub. No.: WO2015/069374
PCT Pub. Date: May 14, 2015

(65) Prior Publication Data

US 2016/0289737 A1 Oct. 6, 2016

Related U.S. Application Data

(60) Provisional application No. 62/013,833, filed on Jun. 18, 2014, provisional application No. 61/901,037, filed on Nov. 7, 2013.

(51) Int. Cl.

| | |
|---|---|
| ***C12Q 1/68*** | (2018.01) |
| ***C12N 9/22*** | (2006.01) |
| ***C12Q 1/6806*** | (2018.01) |
| ***C12Q 1/6869*** | (2018.01) |
| ***C12Q 1/6874*** | (2018.01) |

(52) U.S. Cl.
CPC ............. *C12Q 1/6806* (2013.01); *C12N 9/22* (2013.01); *C12Q 1/6869* (2013.01); *C12Q 1/6874* (2013.01); *C12Y 207/07* (2013.01)

(58) Field of Classification Search
None
See application file for complete search history.

(56) References Cited

U.S. PATENT DOCUMENTS

| | | | | |
|---|---|---|---|---|
| 6,437,109 | B1 | 8/2002 | Reznikoff et al. | |
| 7,803,550 | B2 | 9/2010 | Makarov et al. | |
| 8,192,941 | B2 | 6/2012 | Kuersten | |
| 8,481,292 | B2 | 7/2013 | Casbon et al. | |
| 8,685,678 | B2 | 4/2014 | Casbon et al. | |
| 2003/0143740 | A1 * | 7/2003 | Wooddell ................ | C12N 9/22 435/455 |
| 2007/0172839 | A1 | 7/2007 | Smith et al. | |
| 2012/0301925 | A1 * | 11/2012 | Belyaev ............ | C12N 15/1093 435/91.5 |
| 2013/0017978 | A1 | 1/2013 | Kavanagh et al. | |
| 2013/0023423 | A1 | 1/2013 | Kavanagh et al. | |

FOREIGN PATENT DOCUMENTS

| | | | | |
|---|---|---|---|---|
| EP | 2527438 | A1 | 11/2012 | |
| WO | 2010048605 | A1 | 4/2010 | |
| WO | WO-2012061832 | A1 * | 5/2012 | ......... C12N 15/1065 |
| WO | 2015113725 | A1 | 8/2015 | |

OTHER PUBLICATIONS

Vezzi et al. "Life at depth: Photobacterium profundum genome sequence and expression analysis." Science 307.5714 (2005): 1459-1461) (Year: 2005).*
Vezzi 2005 supp (Year: 2005).*
Genbank records for Accession No. CR354532(2004) (Year: 2004).*
Genbank records for Accession No. CR378678(2004). (Year: 2004).*
Mizuuchi et al., "Control of transposase activity within a transpososome by the configuration of the flanking DNA segment of the transposon," PNAS (Sep. 11, 2007; 104(37):14622-14627.
Saariaho et al., "Characteristics of MuA transposase-catalyzed processing of model transposon end DNA hairpin substrates," Nucleic Acids Research (2006); 34(10)3139-3149.
International Search Report and Written Opinion of the International Searching Authority dated Dec. 2, 2014, for Application No. PCT/US2014/054218.
Aung, K.L., et al., "Current status and future potential of somatic mutation testing from circulating free DNA in patients with solid tumours", Hugo J, 2010, vol. 4, pp. 11-21 (11 pages).
Illumina information sheet, "Using Nextera XT DNA Sample Preparation Kits and Enabling Dual Indexing", 2012 (2 pages).
Munoz-Lopez, M. et al., "DNA Transposons: Nature and Applications in Genomics", Current Genomics, 2010, vol. 11, pp. 115-128 (14 pages).
Navin, N., et al., "Future medical applications of single-cell sequencing in cancer", Genome Medicine, 2011, 3:31 (12 pages).
Nesmelova, I.V., et al., "DDE Transposases: Structural Similarity and Diversity", Adv Drug Deliv Rev, Sep. 30, 2010, vol. 62, issue 12, pp. 1187-1195 (17 pages).
Extended European Search Report issued for EP Application No. 14860451.5 dated Sep. 12, 2017.
Pribil et al., "Substrate Recognition and Induced DNA Deformation by Transposase at the Target-capture Stage of Tn10 Transposition," (2000); 303:145-159.
European Communication dated Oct. 4, 2018 issued for European Application No. 14860451.5-1111.

* cited by examiner

*Primary Examiner* — Tracy Vivlemore
*Assistant Examiner* — Sahana S Kaup

(57) ABSTRACT

The present invention relates to transposase adapters and uses thereof, including uses in preparing DNA molecules, in vitro amplification, sequencing of nucleic acids, and screening of DNA libraries for sequences of interest as well as nucleic acid delivery.

18 Claims, 22 Drawing Sheets

Specification includes a Sequence Listing.

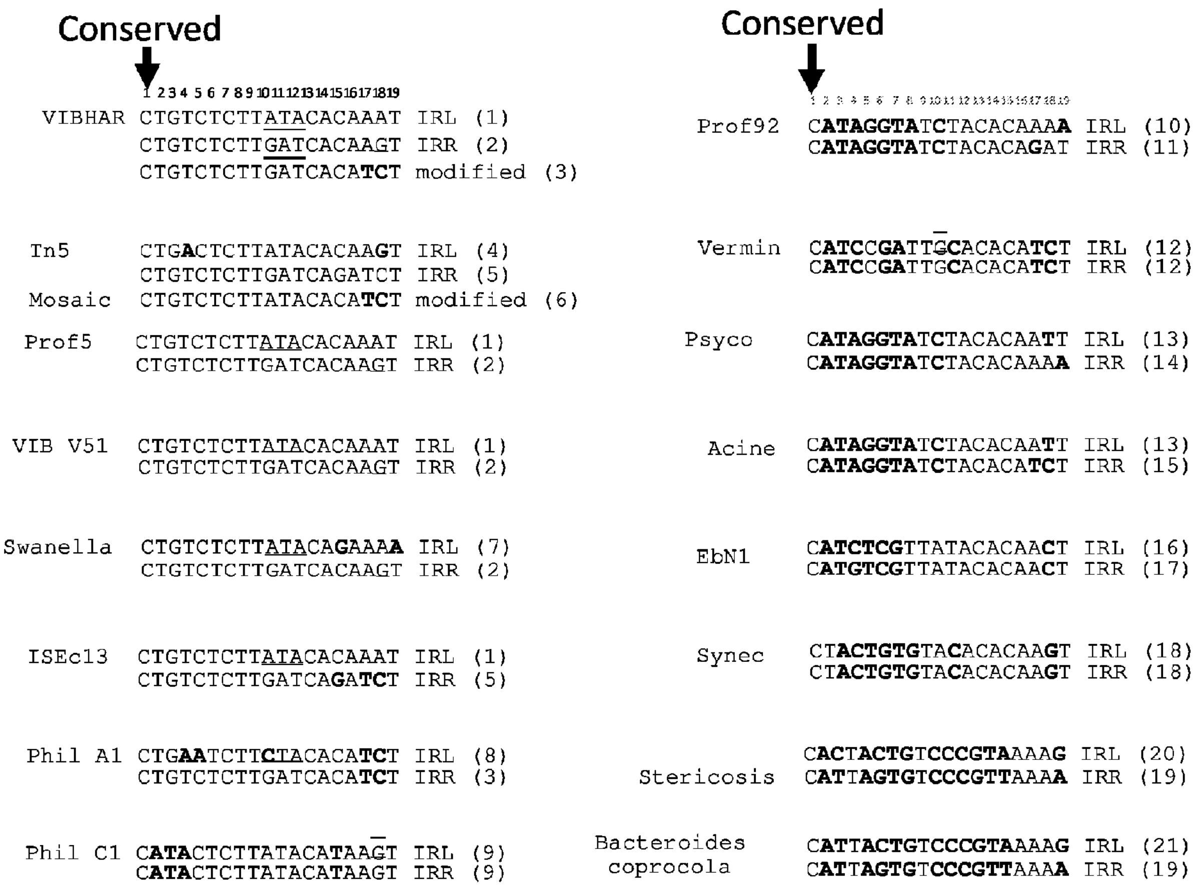

FIG. 1

Conserved

```
         1 2 3 4 5 6 7 8 9 10 11 12 13 14 15 16 17 18 19
VIBHAR   CTGTCTCTTATACACAAAT  IRL (1)
         CTGTCTCTTGATCACAAGT  IRR (2)
         CTGTCTCTTGATCACATCT  modified (3)

Tn5      CTGACTCTTATACACAAGT  IRL (4)
         CTGTCTCTTGATCAGATCT  IRR (5)
Mosaic   CTGTCTCTTATACACATCT  modified (6)

Prof5    CTGTCTCTTATACACAAAT  IRL (1)
         CTGTCTCTTGATCACAAGT  IRR (2)

VIB V51  CTGTCTCTTATACACAAAT  IRL (1)
         CTGTCTCTTGATCACAAGT  IRR (2)

Swanella CTGTCTCTTATACAGAAAA  IRL (7)
         CTGTCTCTTGATCACAAGT  IRR (2)

ISEc13   CTGTCTCTTATACACAAAT  IRL (1)
         CTGTCTCTTGATCAGATCT  IRR (5)

Phil A1  CTGAATCTTCTACACATCT  IRL (8)
         CTGTCTCTTGATCACATCT  IRR (3)

Phil C1  CATACTCTTATACATAAGT  IRL (9)
         CATACTCTTATACATAAGT  IRR (9)
```

Conserved

```
                    1 2 3 4 5 6 7 8 9 10 11 12 13 14 15 16 17 18 19
Prof92              CATAGGTATCTACACAAAA  IRL (10)
                    CATAGGTATCTACACAGAT  IRR (11)

Vermin              CATCCGATTGCACACATCT  IRL (12)
                    CATCCGATTGCACACATCT  IRR (12)

Psyco               CATAGGTATCTACACAATT  IRL (13)
                    CATAGGTATCTACACAAAA  IRR (14)

Acine               CATAGGTATCTACACAATT  IRL (13)
                    CATAGGTATCTACACATCT  IRR (15)

EbN1                CATCTCGTTATACACAACT  IRL (16)
                    CATGTCGTTATACACAACT  IRR (17)

Synec               CTACTGTGTACACACAAGT  IRL (18)
                    CTACTGTGTACACACAAGT  IRR (18)

Stericosis          CACTACTGTCCCGTAAAAG  IRL (20)
                    CATTAGTGTCCCGTTAAAA  IRR (19)

Bacteroides         CATTACTGTCCCGTAAAAG  IRL (21)
coprocola           CATTAGTGTCCCGTTAAAA  IRR (19)
```

Vibhar IRR

1st sequence 5'-CTGTCTCTTGATCACAAGT-3' (2)
2nd sequence 3'-GACAGAGAACTAGTGTTCA-5' (22)

B

| | |
|---|---|
| 5'-CTGTCTCTTGATCACAAGT-3'(2)<br>3'-**H**ACAGAGAACTAGTGTTCA-5'(23) | 5'-**B**TGTCTCTTGATCACAAGT-3'(38)<br>3'-**T**ACAGAGAACTAGTGTTCA-5'(39) |
| 5'-**A**TGTCTCTTGATCACAAGT-3'(24)<br>3'-**V**ACAGAGAACTAGTGTTCA-5'(25) | 5'-**H**TGTCTCTTGATCACAAGT-3'(40)<br>3'-**C**ACAGAGAACTAGTGTTCA-5'(41) |
| 5'-**G**TGTCTCTTGATCACAAGT-3'(26)<br>3'-**D**ACAGAGAACTAGTGTTCA-5'(27) | 5'- TGTCTCTTGATCACAAGT-3'(42)<br>3'-**N**ACAGAGAACTAGTGTTCA-5'(31) |
| 5'-**T**TGTCTCTTGATCACAAGT-3'(28)<br>3'-**B**ACAGAGAACTAGTGTTCA-5'(29) | 5'-**N**TGTCTCTTGATCACAAGT-3'(32)<br>3'- ACAGAGAACTAGTGTTCA-5'(43) |
| 5'-**NN**TGTCTCTTGATCACAAGT-3'(30)<br>3'-**N**ACAGAGAACTAGTGTTCA-5'(31) | 5'- TGTCTCTTGATCACAAGT-3'(44)<br>3'-**NN**ACAGAGAACTAGTGTTCA-5'(33) |
| 5'-**N**TGTCTCTTGATCACAAGT-3'(32)<br>3'-**NN**ACAGAGAACTAGTGTTCA-5'(33) | 5'-**NN**TGTCTCTTGATCACAAGT-3'(30)<br>3'- ACAGAGAACTAGTGTTCA-5'(43) |
| 5'-**N**TGTCTCTTGATCACAAGT-3'(32)<br>3'-**NN**ACAGAGAACTAGTGTTCA-5'(33) | 5'-**M**TGTCTCTTGATCACAAGT-3'(45)<br>3'-**M**ACAGAGAACTAGTGTTCA-5'(46) |
| 5'-**D**TGTCTCTTGATCACAAGT-3'(34)<br>3'-GACAGAGAACTAGTGTTCA-5'(22) | 5'-**M**TGTCTCTTGATCACAAGT-3'(45)<br>3'-**N**ACAGAGAACTAGTGTTCA-5'(31) |
| 5'-**V**TGTCTCTTGATCACAAGT-3'(35)<br>3'-**A**ACAGAGAACTAGTGTTCA-5'(36) | 5'-**N**TGTCTCTTGATCACAAGT-3'(32)<br>3'-**M**ACAGAGAACTAGTGTTCA-5'(46) |
| 5'-**MN**TGTCTCTTGATCACAAGT-3'(37)<br>3'- **N**ACAGAGAACTAGTGTTCA-5'(31) | 5'- **N**TGTCTCTTGATCACAAGT-3'(32)<br>3'-**MN**ACAGAGAACTAGTGTTCA-5'(47) |

D=adenine, guanine, thymine
H=adenine, cytosine, thymine
B=guanine, cytosine, thymine
V=adenine, guanine, cytosine
N=adenine, guanine, cytosine, thymine

M= modified nucleobase, group or spacer, e.g. 2-Aminopurine, 2,6-Diaminopurine, 5-Bromo dU, deoxyUridine, Inverted dT, Inverted Dideoxy-T, Dideoxy-C, 5-Methyl dC, deoxyInosine, Universal base such as 5-Nitroindole, 2'-O-Methyl RNA bases, Iso-dC, Iso-dG, Ribonucleotide, Morpholino, Protein nucleitide analogues, Glycoic nucleotide analogues, Locked nucleotide analogues, Threose nucleotide analogues, Chain terminating nucleotide analogues, Thiouridine, Pseudouridine, Dihydrouridine, Queuosine, Wyosine, abasic site; functional groups, e.g., alkyne functional group, azide functional group such as azide (NHS Ester); nucleobase linked with unnatural bond or spacer, e.g., phosphorothioate bond, 1',2'-Dideoxyribose (dSpacer), Hexanediol, photo-cleavable spacer, different length spacers with different number of carbon atoms, e.g., C3 spacer phosphoramidite, C9 spacer, e.g., a triethylene glycol spacer, C18 an 18-atom hexa-ethyleneglycol spacer.

Mosaic (modified Tn5) → 5'-CTGTCTCTTATACACATCT-3'(6)

First strand → 3'-GACAGAGAATATGTGTAGA-5'(48)

Second strand

B

| | | |
|---|---|---|
| | 5'-**D**TGTCTCTTATACACATCT-3'(60)<br>3'-GACAGAGAATATGTGTAGA-5'(48) | 5'-**M**TGTCTCTTATACACATCT-3'(69)<br>3'-**M**ACAGAGAATATGTGTAGA-5'(70) |
| 5'-CTGTCTCTTATACACATCT-3'(6)<br>3'-**H**ACAGAGAATATGTGTAGA-5'(49) | 5'-**V**TGTCTCTTATACACATCT-3'(61)<br>3'-**A**ACAGAGAATATGTGTAGA-5'(62) | 5'-**M**TGTCTCTTATACACATCT-3'(69)<br>3'-**N**ACAGAGAATATGTGTAGA-5'(57) |
| 5'-**A**TGTCTCTTATACACATCT-3'(50)<br>3'-**V**ACAGAGAATATGTGTAGA-5'(51) | 5'-**B**TGTCTCTTATACACATCT-3'(63)<br>3'-**T**ACAGAGAATATGTGTAGA-5'(64) | 5'-**N**TGTCTCTTATACACATCT-3'(58)<br>3'-**M**ACAGAGAATATGTGTAGA-5'(70) |
| 5'-**G**TGTCTCTTATACACATCT-3'(52)<br>3'-**D**ACAGAGAATATGTGTAGA-5'(53) | 5'-**H**TGTCTCTTATACACATCT-3'(65)<br>3'-**C**ACAGAGAATATGTGTAGA-5'(66) | 5'-**MN**TGTCTCTTATACACATCT-3'(71)<br>3'- **N**ACAGAGAATATGTGTAGA-5'(57) |
| 5'-**T**TGTCTCTTATACACATCT-3'(54)<br>3'-**B**ACAGAGAATATGTGTAGA-5'(55) | 5'- TGTCTCTTATACACATCT-3'(67)<br>3'-**N**ACAGAGAATATGTGTAGA-5'(57) | 5'- **N**TGTCTCTTATACACATCT-3'(58)<br>3'-**MN**ACAGAGAATATGTGTAGA-5'(72) |
| 5'-**NN**TGTCTCTTATACACATCT-3'(56)<br>3'-**N**ACAGAGAATATGTGTAGA-5'(57) | 5'-**N**TGTCTCTTATACACATCT-3'(58)<br>3'- ACAGAGAATATGTGTAGA-5'(68) | |
| 5'-**N**TGTCTCTTATACACATCT-3'(58)<br>3'-**NN**ACAGAGAATATGTGTAGA-5'(59) | 5'- TGTCTCTTATACACATCT-3' (67)<br>3'-**NN**ACAGAGAATATGTGTAGA-5'(59) | |
| 5'-**N**TGTCTCTTATACACATCT-3'(58)<br>3'-**NN**ACAGAGAATATGTGTAGA-5'(59) | 5'-**NN**TGTCTCTTATACACATCT-3'(56)<br>3'- ACAGAGAATATGTGTAGA-5' (68) | |

D=adenine, guanine, thymine
H=adenine, cytosine, thymine
B=guanine, cytosine, thymine
V=adenine, guanine, cytosine
N=adenine, guanine, cytosine, thymine M=modified nucleotide (see Fig. 3)

Adapter 1 (Native Vibhar IRR)
5′-CTGTCTCTTGATCACAAGT-3′(2)
3′-GACAGAGAACTAGTGTTCA-5′(22)

B

| 1 | 4 | 5 | 6 | 7 | 8 | 9 | 10 | 12 | 13 | 14 | 15 | 16 | 17 | 18 | 19 | 20 | 21 | 22 | 23 | 27 | 28 |
|---|---|---|---|---|---|---|---|---|---|---|---|---|---|---|---|---|---|---|---|---|---|
| **C** | **TC** | **AC** | **T** | **T** | **C** | **C** | **C** | **G** | **G** | **G** | **G** | **A** | **A** | **A** | **A** | **T** | **T** | **C** | **C** | **AC** | **TC** |
| **G** | **AG** | **TG** | **A** | **G** | **A** | **AG** | **TG** | **G** | **A** | **T** | **C** | **G** | **A** | **T** | **C** | **T** | **C** | **T** | **C** | **A** | **A** |

C

| | | | | | |
|---|---|---|---|---|---|
| **Ad 4** | 5′-**TC**TGTCTCTTGATCACAAGT-3′(73)<br>3′-**AG**ACAGAGAACTAGTGTTCA-5′(74) | **Ad 12** | 5′-**G**TGTCTCTTGATCACAAGT-3′(26)<br>3′-**G**ACAGAGAACTAGTGTTCA-5′(22) | **Ad 19** | 5′-**A**TGTCTCTTGATCACAAGT-3′(24)<br>3′-**C**ACAGAGAACTAGTGTTCA-5′(41) |
| **Ad 5** | 5′-**AC**TGTCTCTTGATCACAAGT-3′(75)<br>3′-**TG**ACAGAGAACTAGTGTTCA-5′(76) | **Ad 13** | 5′-**G**TGTCTCTTGATCACAAGT-3′(26)<br>3′-**A**ACAGAGAACTAGTGTTCA-5′(36) | **Ad 20** | 5′-**T**TGTCTCTTGATCACAAGT-3′(28)<br>3′-**T**ACAGAGAACTAGTGTTCA-5′(39) |
| **Ad 6** | 5′-**T**TGTCTCTTGATCACAAGT-3′(28)<br>3′-**A**ACAGAGAACTAGTGTTCA-5′(36) | **Ad 14** | 5′-**G**TGTCTCTTGATCACAAGT-3′(26)<br>3′-**T**ACAGAGAACTAGTGTTCA-5′(39) | **Ad 21** | 5′-**T**TGTCTCTTGATCACAAGT-3′(28)<br>3′-**C**ACAGAGAACTAGTGTTCA-5′(41) |
| **Ad 7** | 5′-**T**TGTCTCTTGATCACAAGT-3′(28)<br>3′-**G**ACAGAGAACTAGTGTTCA-5′(22) | **Ad 15** | 5′-**G**TGTCTCTTGATCACAAGT-3′(26)<br>3′-**C**ACAGAGAACTAGTGTTCA-5′(41) | **Ad 22** | 5′-**C**TGTCTCTTGATCACAAGT-3′(2)<br>3′-**T**ACAGAGAACTAGTGTTCA-5′(39) |
| **Ad 8** | 5′-**C**TGTCTCTTGATCACAAGT-3′(2)<br>3′-**A**ACAGAGAACTAGTGTTCA-5′(36) | **Ad 16** | 5′-**A**TGTCTCTTGATCACAAGT-3′(24)<br>3′-**G**ACAGAGAACTAGTGTTCA-5′(22) | **Ad 23** | 5′-**C**TGTCTCTTGATCACAAGT-3′(2)<br>3′-**C**ACAGAGAACTAGTGTTCA-5′(41) |
| **Ad 9** | 5′-**C**TGTCTCTTGATCACAAGT-3′(2)<br>3′-**AG**ACAGAGAACTAGTGTTCA-5′(74) | **Ad 17** | 5′-**A**TGTCTCTTGATCACAAGT-3′(24)<br>3′-**A**ACAGAGAACTAGTGTTCA-5′(36) | **Ad 27** | 5′-**AC**TGTCTCTTGATCACAAGT-3′(75)<br>3′- **A**ACAGAGAACTAGTGTTCA-5′(36) |
| **Ad 10** | 5′-**C**TGTCTCTTGATCACAAGT-3′(2)<br>3′-**TG**ACAGAGAACTAGTGTTCA-5′(76) | **Ad 18** | 5′-**A**TGTCTCTTGATCACAAGT-3′(24)<br>3′-**T**ACAGAGAACTAGTGTTCA-5′(39) | **Ad 28** | 5′-**TC**TGTCTCTTGATCACAAGT-3′(73)<br>3′- **A**ACAGAGAACTAGTGTTCA-5′(36) |

A (20 ng)

B (1ng)

C (68pg)

D (4pg)

1ng *E. coli* DNA template in 20 ul transposase reactions. Loaded transposase concentrations in transposase reactions: A-5 ug/ml, B-1.7ug/ml, C-0.56 ug/ml, D-0.19 ug/ml . Reaction 20' at 45C , then PCR 14 cycles Amplification-26 PCR cycles 1/13 of amount of DNA in Human cell Processing of 0.5 pg DNA in 20 ul of transposase reaction, 45°C 30 min.

| Index | 1 | 2 | 3 | 4 | 5 | 6 | 7 | 8 |
|---|---|---|---|---|---|---|---|---|
| Adapter | 1 (standard) | 9 | 10 | Mix of 1,5-10 | 5 | 6 | 7 | 8 |
| % duplications Normalized to 1.3M reads | 0.4036 | 0.2045 | 0.4104 | 0.0855 | 0.2454 | 0.6864 | 0.4056 | 1.5797 |

FIG. 12

AT dropouts widely with different adapters

Index

| NAME | WINDOW_SIZE | TOTAL_CLUSTERS | | ALIGNED_READS | AT_DROPOUT | ADAPTER |
|---|---|---|---|---|---|---|
| L001_I001_4AL | 100 | 650361 | 1256518 | 4.711141 | 0.009391 | 1 |
| L001_I002_4AL | 100 | 650204 | 1235541 | 2.673559 | 0.093704 | 9 |
| L001_I003_4AL | 100 | 650099 | 1226636 | 3.947259 | 0.001347 | 10 |
| L001_I004_4AL | 100 | 650022 | 1230762 | 4.507024 | 0.002295 | Mixture 1,5-10 |
| L001_I005_4AL | 100 | 649962 | 1239987 | 1.471879 | 1.528892 | 5 |
| L001_I006_4AL | 100 | 364530 | 698717 | 5.070903 | 0.004691 | 6 |
| L001_I007_4AL | 100 | 650284 | 1249440 | 3.387535 | 0.130654 | 7 |
| L001_I008_4AL | 100 | 650005 | 1246407 | 7.528258 | 0.000025 | 8 |

FIG. 19

A. Examples of phosphorothioate derivatives of adapter 78

721 A*G*ATGTGATCAAGAGACA*G (96)
8 T-C-TACACTAGTTCTCTGT-C (97)

791 A*G*A*T*G*T*G*A*T*CAAGAGACA*G (98)
8 T-C-T-A-C-A-C-T-A-GTTCTCTGT-C (97)

721 A*G*ATGTGATCAAGAGACA*G (96)
801 T-C-TACACTAGTTCTCTGT*C (99)

791 A*G*A*T*G*T*G*A*T*CAAGAGACA*G (98)
801 T-C-T-A-C-A-C-T-A-GTTCTCTGT*C (99)

81P A*G*A*T*G*T*G*A*T*CAAGAGACAG (100)
8 T-C-T-A-C-A-C-T-A-GTTCTCTGTC (97)

712 A*G*A*T*G*T*G*A*T*C*AAGAGAC*A*G (101)
8 T-C-T-A-C-A-C-T-A-G-TTCTCTG-T-C (97)

713 A*G*A*T*G*T*G*A*T*C*AAGAGA*C*A*G (102)
8 T-C-T-A-C-A-C-T-A-G-T-TCTCTG-T-C (97)

714 A*G*A*T*G*T*G*A*T*C*A*AGA*GAC*A*G (103)
8 T-C-T-A-C-A-C-T-A-G-T-TCT-CTG-T-C (97)

715 A*G*A*T*G*T*G*A*T*C*A*AG*AG*AC*A*G (104)
8 T-C-T-A-C-A-C-T-A-G-T-TC-TC-TG-T-C (97)

B. Phosphorothioate derivatives of standard adapters

8i15 G*G*A*G*C*T*G*T*G*C*G*T*A*G*ATGTGATCAAGAGACA*G (105)

3i15 G*C*T*G*A*C*G*T*C*G*A*G*A*C*TTGTGATCAAGAGACA*G (106)

8i3 G*G*AGCTGTGCGTAGATGTGATCAAGAGACA*G (107)

3i3 G*C*TGACGTCGAGACTTGTGATCAAGAGACA*G (108)

8i5 G*G*AGCTGTGCGTA*G*ATGTGATCAAGAGACA*G (109)

3i5 G*C*TGACGTCGAGA*C*TTGTGATCAAGAGACA*G (110)

C. Phosphorothioate derivatives combined with mis-pairing, inverted dT and dU bases

81PA A*G*A*T*G*T*G*A*T*CAAGAGACAA (111)
8 T-C-T-A-C-A-C-T-A-GTTCTCTGTC (97)

791A A*G*A*T*G*T*G*A*T*CAAGAGACA*A (112)
8 T-C-T-A-C-A-C-T-A-GTTCTCTGT-C (97)

791 A*G*A*T*G*T*G*A*T*CAAGAGACA*G (113)
/InvdT/*T-C-T-A-C-A-C-T-A-GTTCTCTGT-C (114)

791 A*G*A*T*G*T*G*A*T*CAAGAGACA*A (115)
/InvdT/*T-C-T-A-C-A-C-T-A-GTTCTCTGT-C (114)

791 A*G*A*T*G*T*G*A*T*CAAGAGACA*G (113)
/InvdT/*T-C-T-A-C-A-C-U-A-GUUCUCTGT-C (117)

791 A*G*A*T*G*T*G*A*T*CAAGAGACA*A (115)
8U4 T-C-T-A-C-A-C-U-A-GUUCUCTGT-C (118)

FIG. 20

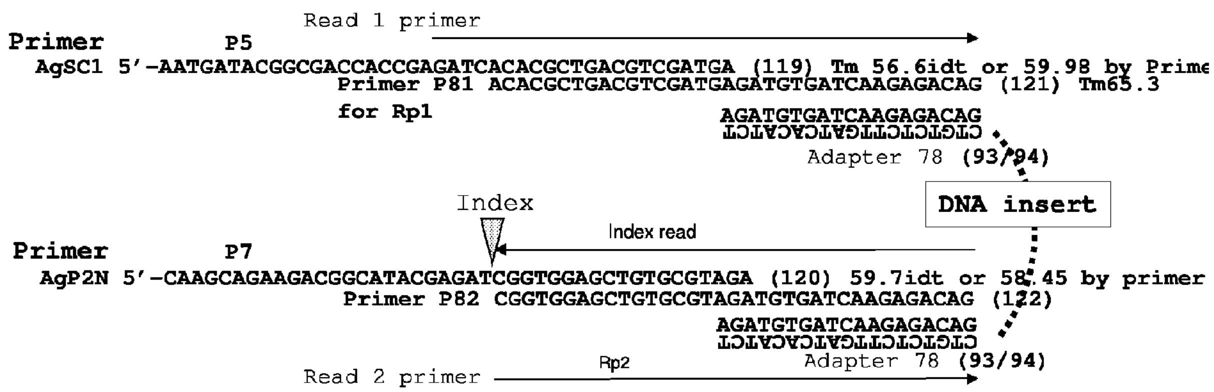

Indexed primers (used instead of Agp2N)

SCAi1 CAAGCAGAAGACGGCATACGAGATCGTGATCGGTGGAGCTGTGCGTAGA (123)

SCAi2 CAAGCAGAAGACGGCATACGAGATACATCGCGGTGGAGCTGTGCGTAGA (124)

SCAi3 CAAGCAGAAGACGGCATACGAGATGCCTAACGGTGGAGCTGTGCGTAGA (125)

SCAi4 CAAGCAGAAGACGGCATACGAGATTGGTCACGGTGGAGCTGTGCGTAGA (126)

SCAi5 CAAGCAGAAGACGGCATACGAGATCACTGTCGGTGGAGCTGTGCGTAGA (127)

SCAi6 CAAGCAGAAGACGGCATACGAGATATTGGCCGGTGGAGCTGTGCGTAGA (128)

SCAi7 CAAGCAGAAGACGGCATACGAGATGATCTGCGGTGGAGCTGTGCGTAGA (129)

SCAi8 CAAGCAGAAGACGGCATACGAGATTCAAGTCGGTGGAGCTGTGCGTAGA (130)

SCAi9 CAAGCAGAAGACGGCATACGAGATCTGATCCGGTGGAGCTGTGCGTAGA (131)

SCAi10 CAAGCAGAAGACGGCATACGAGATAAGCTACGGTGGAGCTGTGCGTAGA (132)

PLURALITY OF TRANSPOSASE ADAPTERS FOR DNA MANIPULATIONS

CROSS REFERENCE TO RELATED APPLICATIONS

This application is a U.S. National Phase of International Application No. PCT/US2014/054218, filed Sep. 5, 2014, which claims priority of U.S. Provisional Application No. 61/901,037 filed on Nov. 7, 2013 and U.S. Provisional Application No. 62/013,833 filed on Jun. 18, 2014. The contents of the applications are incorporated herein by reference in their entireties.

FIELD OF THE INVENTION

The present invention relates to transposase adapters and uses thereof, including uses in preparing DNA molecules, in vitro amplification, sequencing of nucleic acids, and screening of DNA libraries for sequences of interest as well as nucleic acid delivery into living cells.

BACKGROUND OF THE INVENTION

Transposase is a class of enzyme that binds to the ends of a transposon and catalyzes the movement of the transposon to another part of the genome by a cut and paste mechanism or a replicative transposition mechanism. These enzymes have been used in preparation of samples for next generation sequencing (NGS), mutagenesis, nucleic acid delivery (gene therapy), and generating pluripotent cells for regenerative medicine. In these applications, transposases do not act as isolated proteins, but act as nucleoproteins in complex with specific DNA sequences. Such sequences are commonly referred to as transposase recognition sequences, transposon ends, inverted repeat right (IRR), inverted repeat left (IRL), or adapters.

When used for NGS library preparation, transposase-adapter complexes are used to fragment genomic DNA, which is a crucial step to achieve high-throughput sequencing. Compared with other fragmentation techniques, such as sonication and DNAse treatment, transposase-based fragmentation allows many-fold save in time, labor and equipment expenditure taking into account that sample preparation constitutes about 50% of the overall sequencing costs. However, DNA fragmentation by currently available transposase-adapter complexes is less random. That is, it has bias resulting in more reads in some regions and less in others, which often results in 1-3% higher duplication rate and more sequencing effort to achieve the same overall coverage. Also conventional transposase-based NGS sample preparation methods require removal of adapters, which is time consuming, and are not suitable for processing samples with very low amount of DNAs.

Thus, there is also an un-met need for different transposase adapters with suitable activity and different properties so as to increase the randomness and reduce the duplication rate. There is an un-met need for methods that more efficient and/or suitable for direct processing in transposase reaction of samples with very low amount of DNAs.

SUMMARY OF INVENTION

This invention addresses the above-mentioned un-met needs by providing a plurality of transposase adapters.

In one aspect, the invention provides an isolated synthetic nucleic acid adapter that contains a first strand comprising a first sequence and a second strand comprising a second sequence. The first sequence and the second sequence are fully complementary or substantially complementary to each other, and the adapter is recognized by the transposase.

The isolated synthetic nucleic acid adapter comprises a transposase recognition sequence having one or more modifications as compared to a native recognition sequence for a transposase. For example, either the first sequence is a modified version of a parental, native or known recognition sequence for a transposase, or the second sequence is a modified version of the complement of the parental adapter sequence, or both are such modified versions.

The isolated synthetic nucleic acid adapter can have one or more of the following modifications as compared to a native recognition sequence for a transposase: (a) one or more modifications at the 5' terminus (position 1) of the first sequence (on the first strand), or at the 3' terminus of the second sequence (on the second strand), or at both; (b) one or more modified nucleotides in the first strand or the first sequence, wherein said modified nucleotides impede a primer extension of said first stand; and (c) one or more phosphorothioate bonds in the second strand or the second sequence.

In one embodiment, the isolated synthetic nucleic acid adapter has one or more modifications at the 5' terminus (position 1) of the first sequence as compared to a native or known recognition sequence for a transposase (a parental adapter sequence or a parental recognition sequence), or at the 3' terminus of the second sequence as compared to the complement of the native recognition sequence, or at both of said termini. For example, the first sequence can have a different nucleotide, at least one additional nucleotide or lack one nucleotide at its 5' terminus as compared to the parental recognition sequence. Similarly, the second sequence can also have at least one different nucleotide, additional nucleotide or lack one nucleotide at its 3' terminus as compared to the complement. Examples of these adapters are shown at FIGS. 3B, 4B, and 5C.

In another embodiment, the one or more modified nucleotides in part (b) mentioned above are selected from the group consisting of a deoxyuridine, an abasic site, a 2'OMe modified ribonucleic acid (RNA), and an inverted thymidine. The inverted thymidine is preferably at the 3' terminus of the first strand. In some examples, the one or more modified nucleotides are preceded by (i.e., 5' to the modified nucleotides) a phosphorothioate bond or a spacer. The second strand can be free of such one or more modified nucleotides.

In yet another embodiment, at least one phosphorothioate bond is between the 3' ultimate nucleotide and the 3' pen-ultimate nucleotide of the second strand or the second sequence. The second strand or the second sequence can contain about 1 to 18 (e.g., 2-15, 3-14, or 4-10, e.g., 1, 2, 3, 4, 5, 6, 7, 8, 9, 10, 11, 12, 13, 14, 15, 16, 17, or 18) phosphorothioate bonds. The first strand or the first sequence can be free of phosphorothioate bond.

In the above-mentioned adapter, the first strand and the second strand can form a duplex. The duplex can be 15-30 bp in length. In that case, the duplex can have a blunt end or a staggered end at the 3' or 5' terminus/end of the first or second strand (e.g., at the 3' terminus of the second strand or the 5' terminus of the first strand). In the adapter, the one or more modifications in the first or second sequence can result in one or more unpaired nucleotides in the duplex, e.g., unpaired bases or an overhung (such as at one or more end of the first or second strand).

Preferably, the first or second sequence (or strand) is 17-80, 18-60, or 19-50 nucleotides in length, e.g., 17, 18, 19, 20, 21, 22, 23, 24, 25, 30, 40, 50, 60, or 80 nucleotides in length. In more preferred embodiments, the first or second sequence is 19-21 nucleotides in length, i.e., 19 or 20 or 21 nucleotides in length.

In some preferred embodiments, the parental, native or known recognition sequence has a C at position 1. Examples of such a parental recognition sequences including those shown in FIG. 1. In one embodiment, an adapter of this invention has a G to A substitution on the second sequence (i.e., the bottom strand shown in FIGS. 3-5) at position 1 (e.g., adapters 6, 8, 13, 17, and 27 as shown in FIG. 5 and described in example 2 below). In another embodiment, the adapter has both a G to A substitution at position 1 on the second sequence and a mismatched base on the opposite strand, i.e., position 1 in the first sequence (e.g., adapters 8 and 27 with a mismatched C at that position). In yet another embodiment, the adapter has the native G at position 1 of the second sequence, but has a mismatched base on the opposite strand (e.g., adapters 7 and 12 with mismatched T and G at that position, respectively). All of these adapters confer increased activity as compared to the parent adapter.

In a further embodiment, the adapter can have an additional base 5' to the position 1 C of the first sequence or an additional base 3' to the position 1 G of the adapter sequence (e.g., adapters 5, 9, and 10). These adapters have duplication rates lower than or comparable to the parent adapter.

In some embodiments, the first or second strand can contain at least one modified nucleotide selected from the group consisting of 2-Aminopurine, 2,6-Diaminopurine, 5-Bromo dU, deoxyUridine, inverted dT, inverted Dideoxy-T, dideoxy-C, 5-Methyl dC, deoxyInosine, a universal base comprising 5-Nitroindole, a 2'-O-Methyl RNA base, iso-dC, iso-dG, ribonucleotide, morpholino, a protein nucleitide analogue, a glycoic nucleotide analogue, a locked nucleotide analogue, a threose nucleotide analogue, a chain terminating nucleotide analogue, thiouridine, pseudouridine, dihydrouridine, queuosine, and wyosine. In others, at least one nucleotide in the first or second strand can be phosphorylated or ribonucleotide, or have a modified sugar, an unnatural bond, an abasic site, a dideoxy base, a 5-methyl base, or a spacer. In some embodiments, the second strand can further comprise a tag sequence 5' to the second sequence. Similarly, the first strand can further comprise a tag sequence 3' to the first sequence, e.g., beyond position 19 as shown in FIG. 1. The tags to the first and second sequence can be non-complementary to each other based on their uses as will be described below. For the adapter, the transposase can be a "cut and paste" transposase, such as a *Vibrio Harveyi* transposase or a hyperactive Tn5 transposase.

The invention also provides a set of isolated synthetic nucleic acid adapters that have (i) a first isolated synthetic nucleic acid adapter and (ii) second isolated synthetic nucleic acid adapter mentioned above, where the first adapter and/or the second adapter have at least one different modification as compared to their respective parental recognition sequence or the complement thereof. For example, at least one of the two adapters is the isolated synthetic nucleic acid adapter described above. The two adapters can be recognized by the same transposase or by two different transposases.

Examples of the sets include any combinations of the following adapters: adapters 4-10, 12-23 and 27-28 as shown in FIG. 5C, adapters 3U2, 8U2, 3U4, 8U4, 3i0*dT, and 8i0*dT as shown in FIG. 13, adapter E8 (FIG. 18), and those adapters shown in FIG. 19.

The first sequence and the second sequence can comprise, consist essentially of, or consist of, respectively, SEQ ID NOs: 73 and 74, SEQ ID NOs: 75 and 76, SEQ ID NOs: 28 and 36, SEQ ID NOs: 28 and 22, SEQ ID NOs: 2 and 36, SEQ ID NOs: 2 and 74, SEQ ID NOs: 2 and 76, SEQ ID NOs: 26 and 22, SEQ ID NOs: 26 and 36, SEQ ID NOs: 26 and 39, SEQ ID NOs: 26 and 41, SEQ ID NOs: 24 and 22, SEQ ID NOs: 24 and 36, SEQ ID NOs: 24 and 39, SEQ ID NOs: 24 and 41, SEQ ID NOs: 28 and 39, SEQ ID NOs: 28 and 41, SEQ ID NOs: 2 and 39, SEQ ID NOs: 2 and 41, SEQ ID NOs: 75 and 36, or SEQ ID NOs: 73 and 36. Other examples include a set of adapters 1 and 5-10 as shown in FIG. 11, a set of adapters 5-10, a set of adapters 6, 8, 13, 17, and 27, a set of adapters 8 and 27, a set of adapters 7 and 12, and a set of adapters 5 and 9. Additional examples include any combination of adapters 5-10, 12, 13, 17, and 27. Other examples include adapter pairs 2-4 shown in FIG. 13, and any combination of those shown in FIG. 19.

Also provided is a kit having a first transposase and a first adapter mentioned above that has a sequence recognized by the transposase. The kit can further include at least one component selected from the group consisting of a buffer, a polymerization enzyme, an endonuclease, and a restriction enzyme, and instructions for making a DNA library from a target DNA. In some embodiments, the second strand of the adapter further comprises a tag sequence 5' to the second sequence and the kit further comprises a primer complimentary to the tag sequence. In others, the kit can further include a second adapter that is different from the first adapter but can be recognized by the first transposase or a different transposase.

In another aspect, the invention provides an in vitro method for fragmenting a target DNA molecule. The method includes the steps of: obtaining a transposase, obtaining an isolated synthetic nucleic acid adapter described above that can be recognized by the transposase; mixing the adapter, the transposase, and a target DNA molecule; incubating the adapter, the transposase, and the target DNA under conditions for carrying out a transposition reaction, whereby the adapter and the transposase associate with the target DNA molecule and cleave the target DNA molecule via transposase-mediated cleavage to provide a cleaved DNA product.

In other aspects, the invention provides a transposase complex containing a transposase component having at least one transposase and an adapter of this invention. To produce a transposase complex, one can incubate one or more transposases with one or more adapters of this invention, which contains a recognition sequence for the transposase, and allow sufficient time for the adapters to bind to the transposases, thereby creating a transposase complex. This transposase complex can be bound to a solid substrate. In that case, one can use a linker component that contains a specific binding pair. One of the members of the specific binding pair can be bound to the adapter and the other member to the solid substrate. In such solid substrate-bound transposase complexes, at least one of the adapters per complex has bound to it a member of the specific binding pair.

In yet other aspect, the invention provides an in vitro method for fragmenting a target DNA molecule. The method includes contacting a target DNA molecule with a transposase complex mentioned above to form a reaction mixture and incubating the reaction mixture under conditions for carrying out a transposition reaction. The target DNA molecule can be obtained from a sample consisting of a low number of cells, e.g., 1-10 cells, 1-3 cells, or one single cell, or a chromosome.

The invention further provides a method for preparing an assay sample for sequencing or microarray analysis of a target DNA molecule. The method includes contacting a target DNA molecule with a complex having an isolated synthetic nucleic acid adapter described above and a transposase that binds to the adapter to form a reaction mixture; incubating the reaction mixture under conditions for carrying out a transposition reaction to generate a cleaved DNA product, and amplifying the cleaved DNA product. As disclosed herein, due to the superiority of the adapter, there is no need for removing of the adapter before the amplifying step. That is, the amplifying step is conducted without prior removing of the adapter.

Also provided is a method of DNA sample preparation for microarrays. The method includes contacting a sample DNA molecule with a complex having an isolated synthetic nucleic acid adapter disclosed herein and a transposase that binds to the adapter to form a reaction mixture; and incubating the reaction mixture under conditions for carrying out a transposition reaction to generate DNA fragments of the sample DNA molecule. The adapter has an oligonucleotide tag and the DNA fragments are tagged at both ends with the oligonucleotide tag. The method can further include amplifying the DNA fragments using primers complementary to the oligonucleotide tag. The tag can be used as a landing site for a primer complementary to the tag. The primer or primers can be extended in polymerase reaction using dNTP mixture comprising at least one dNTP labeled with a fluorophore.

The details of one or more embodiments of the invention are set forth in the description and drawings below. Other features, objects, and advantages of the invention will be apparent from the description, drawings, and claims.

BRIEF DESCRIPTION OF THE DRAWINGS

FIG. 1 is a list of native IRL and IRR, and modified adapters of transposases with only one strand is shown, where the first position (C) in the adapters is conserved and different colors illustrate similarities and differences in different adapters. The numbers in the parentheses following the sequences refer to their SEQ ID NOs, i.e., SEQ ID NOs: 1-21, respectively.

FIGS. 3A and 3B are lists schematically representing (A) a parental adapter duplex comprising $1^{st}$ and $2^{nd}$ adapter sequences for Vibhar transposase and (B) a plurality of modified adapters, where the top strand and bottom strand correspond to the above-mentioned first and second sequences, respectively. The numbers in the parentheses following the sequences refer to their SEQ ID NOs, i.e., SEQ ID NOs: 2 and 22-47, respectively.

FIGS. 4A and 4B are a list schematically representing (A) a parental adapter for "hyperactive" Tn5 transposase and (B) a plurality of modified adapters, where the top strand and bottom strand correspond to the above-mentioned first and second sequences, respectively. The numbers in the parentheses following the sequences refer to their SEQ ID NOs. i.e., SEQ ID NOs: 6 and 48-72 respectively.

FIGS. 5A, 5B, and 5C are diagrams that represent examples of adapters for Vibhar transposase based on substitutions and additions of nucleotides: (A) parental adapter, (B) adapters numbering based on changes/additions in position 1, and (C) examples of derivative adapters. The numbers in the parentheses following the sequences refer to their SEQ ID NOs, i.e., SEQ ID NOs: 2, 22, 24, 26, 28, 36, 39, 41, and 74-76, respectively.

FIG. 12 is a diagram showing AT dropouts conferred to Vibhar transposase by different adapters.

FIGS. 19A, 19B, and 19C show derivatives of transposase adapters: (A) Examples of phosphorothioate derivatives of adapter 78; (B) Phosphorothioate derivatives of standard adapters (only top strand relative to depicted on FIG. 16 is shown); and (C) Phosphorothioate adapters combined with mis-pairing, inverted dT and dU modifications. The numbers in the parentheses following the sequences refer to their SEQ ID NOs, i.e., SEQ ID NOs: 96-118, respectively.

FIG. 20 illustrates primers for PCR amplification of adapter 78 or its derivatives in a 4-primer PCR reaction for sample preparation suitable for NGS sequencing on Illumina instruments. P5 and P7 designate portions necessary for attachment to Illumina flow cell. The numbers in the parentheses following the sequences refer to their SEQ ID NOs, i.e., SEQ ID NOs: 93, 94, and 119-132, respectively.

DETAILED DESCRIPTION OF THE INVENTION

Figure 2:
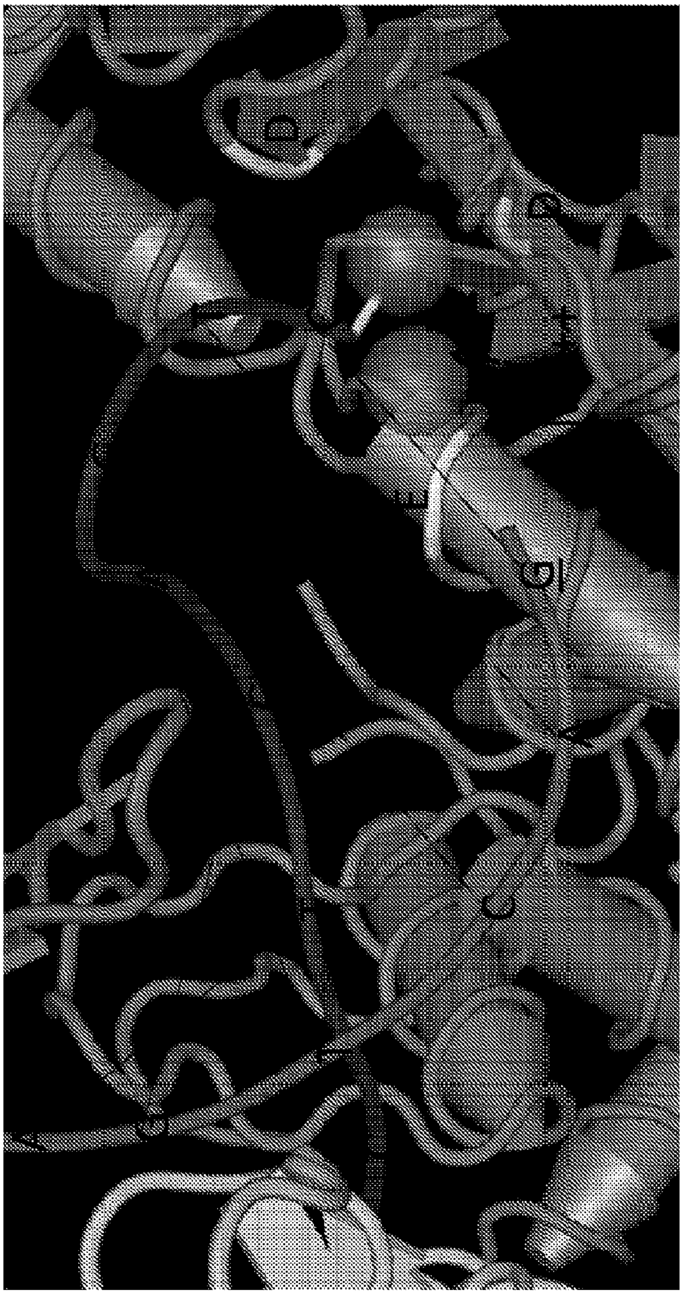
FIG. 2 is a diagram showing catalytic site of Tn5 transposase with the DDE motif and an adapter. Conserved C (at position 1 as illustrated in FIG. 1) and conserved G on the opposite adapter strand are underlined.

This invention is based, at least in part, on an unexpected discovery of a plurality of isolated synthetic nucleic acid transposase adapters. It was surprising that, although these synthetic adapters differ from known functional transposase adapters (both native or modified) at the most conserved sites, the synthetic adapters retain the activities and some of them have even higher activities, resulting in increased randomness, reduced duplication rate, or both when used for NGS. In some embodiments, it was demonstrated that a plurality of useful adapters conferring different properties to a transposase of choice can be generated by modifying conserved position 1 in a native adapter. It was also surprising to find out that some modifications to the adapters allow one to prepare DNA samples for NGS without removal of adapters, which is time consuming, and/or allow one to process samples with a very low amount of DNAs.

Adapters

The invention provides an isolated synthetic nucleic acid adapter that contains a first strand and second strand that comprise, consisting essentially of, or consisting of the above-mentioned first sequence and second sequence, respectively. The first sequence and the second sequence are fully complementary or substantially complementary to each other, and the adapter is recognized by the transposase.

As mentioned above, transposases do not act as isolated proteins, but act in complex with specific DNA sequences or adapters, which can form stable complexes with transposases and thus render them active. The adapters could be transposase recognition sequences found in nature, or they also could be modified native sequences. Conventionally, as a rule, only one such sequence is recommended for use with a specific transposase. For example, "hyperactive" Tn 5 transposase that was mutated to render it more active, more stable, and better expressed, recognizes "mosaic" sequence (adapter), that was also mutated from native sequence and only this sequence is recommended for use with this transposase (Zhou et al., J Mol Biol. 1998, 276(5):913-25; Brouilette et al., Dev Dyn. 2012, 241(10):1584-90).

Transposase DDE amino acid motif is known to be a part of the catalytic site and is necessary for transposase activity (Nesmelova and Hackett, Adv Drug Deliv Rev. 2010, 30; 62(12):1187-95; Steiniger-White et al., Curr Opin Struct Biol. 2004, February; 14(1):50-7). Since both the DDE motif and the presence of adapter in its vicinity are necessary for the activity, the inventor recognized that properties of the complex can be aptly modulated by changing nucleotides in the adapter that are positioned in the catalytic site close to the DDE motif. However, it was known in the art that, similar to the DDE motif, which is strictly conserved, the nucleotides in the adapters that are closest to the catalytic site are also strictly conserved. To that end, FIG. 1 lists a number of known native and modified adapters of transposases with only one strand is shown. As shown in the figure, C at the first position in the adapters is conserved among all of the different adapters.

The term "adapter" as used herein refers to a non-target nucleic acid component, generally DNA, which provides a means of addressing a nucleic acid fragment to which it is subsequently joined. For example, in embodiments, an adapter comprises a nucleotide sequence that permits identification, recognition, and/or molecular or biochemical manipulation of the DNA to which the adapter is attached (e.g., by providing a site for annealing an oligonucleotide, such as a primer for extension by a DNA polymerase, or an oligonucleotide for capture or for a ligation reaction). As disclosed herein, an adapter of this invention has (i) a first strand having a first sequence that is a modified version of a native or known recognition sequence for a transposase, and/or (ii) a second strand having a second sequence that is a modified version of the complement of the recognition sequence. One of the strands of the adapter can be native, and another can contain modification(s).

The terms "recognition sequence for a transposase," "transposase recognition sequence," "transposase binding sequence" and "transposase binding site" are used here interchangeably to refer to the nucleotide sequences that are found within a transposon end sequence where a transposase specifically binds when mediating transposition. The transposase binding sequence may comprise more than one site for binding transposase subunits.

A "transposase" refers to an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated in an in vitro or in vivo transposition reaction.

The term "transposon end" means a double-stranded DNA that exhibits only the nucleotide sequences (the "transposon end sequences") that are necessary to form the complex with the transposase or integrase enzyme that is functional in an in vitro or in vivo transposition reaction. A transposon end forms a "complex," a "synaptic complex" or a "transposome complex." A transposon end exhibits two complementary sequences consisting of (i) a "transferred transposon end sequence" or "transferred strand" and (ii) a "non-transferred transposon end sequence," or "non-transferred strand." For example, a number of transposon ends/adapters for Vibhar transposase are shown in FIG. 3. The top stand in each (e.g., 5'-CTGTCTCTTGATCACAAGT-3' for Vibhar IRR, SEQ ID NO: 2) is a non-transferred strand that exhibits a non-transferred transposon end sequence, while the bottom strand (e.g., 3'-GACAGAGAACTAGTGTTCA-5' or 5'-ACTTGTGATCAAGAGACAG-3' for Vibhar IRR, SEQ ID NO: 22) is a transferred strand that exhibits a transferred transposon end sequence. Similarly, in FIG. 4, the top stand in each (e.g., 5'-CTGTCTCTTATACACATCT-3' for Mosaic (modified Tn5, SEQ ID NO: 6) is a non-transferred strand while the bottom strand (e.g., 5'-AGATGTGTATAAGAGACAG-3' for Mosaic (modified Tn5), SEQ ID NO: 48) is a transferred strand. As used herein, the term "a first strand" refers to a non-transferred strand and in FIGS. 3-5 such a first strand/non-transferred strand is shown as the top strand for each adapter. The term "a second strand" refers to a transferred strand and in FIGS. 3-5, such a second strand/transferred strand is shown as the bottom strand for each adapter. In a wild type transposon end, the non-transferred/first/top strand has a conservative C at its 5' end and the corresponding transferred/second/bottom strand has a conservative G at its 3' end. In FIGS. 13, 16, 18, 19, and 21, the non-transferred/first strand is shown as the bottom stand for each adapter while the corresponding transferred/second strand is shown as the top one for each adapter, In FIG. 1, only the non-transferred/first strands are shown and all of them have the conservative C at the 5' ends or position 1.

As used herein, "position 1" refers to the position corresponding to the 5' end C nucleotide on the non-transferred/first strand of a wild type transposon end as shown in FIG. 1 and to the 3' end G nucleotide on the corresponding transferred/second strand/bottom strand as shown in, e.g., FIGS. 3-5. Also, as shown and underlined in FIG. 2, position 1 (C of the non-transferred/first top strand and G of the transferred/second strand/bottom stand) is at the catalytic site of a transposase.

As mentioned above, in some embodiments, the first and second sequences within the adapter of this invention are complementary or substantially complementary to each other. As used herein, and unless otherwise indicated, the terms "complementary" or "substantially complementary" when used to describe a first nucleotide sequence in relation to a second nucleotide sequence, refers to the ability of an oligonucleotide or polynucleotide comprising a first nucleotide sequence to hybridize and form a duplex structure under conditions with an oligonucleotide or polynucleotide comprising a second nucleotide sequence, as will be understood by the skilled person in the art.

This includes base-pairing of the oligonucleotide or polynucleotide comprising the first nucleotide sequence to the oligonucleotide or polynucleotide comprising the second nucleotide sequence over the entire length of the first nucleotide sequence and second nucleotide sequence. Such sequences can be referred to as "fully complementary" with respect to each other herein. However, in some embodiments, a first nucleotide sequence and a second nucleotide sequence may be substantially complementary to each other, that is at least about 80%, 90%, 95%, 96%, 97%, 98%, or 99% complementary to each other unless otherwise indicated. As used herein, where a first sequence is referred to as "substantially complementary" with respect to a second sequence herein, the two sequences can be fully complementary, or they may form one or more, but generally not more than, for example 4, 3, 2, or 1 mismatched base pair over the length of 19-21 bp, and preferably 2 or 1 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity.

"Complementary" sequences, as used herein, may include, or be formed entirely from, Watson-Crick base pairs, non-Watson-Crick base pairs and/or base pairs formed from non-natural and modified nucleotides, and in as far as the above requirements with respect to their ability to hybridize are fulfilled.

A. Adapters with Modifications at Position 1

In one embodiment, an adapter of this invention has a strand with a sequence that is generally a modified version of a native or known recognition sequence for a transposase. Because of the strictly conserved nature at position 1 of a native or known recognition sequence, the task of modulating transposase complex properties by changing these nucleotides seemed to be daunting. Indeed, it was well understood in the art that changes in strictly conserved nucleotide positions should inevitably result in sharp drop in activity, just as the changes in conserved DDE motif render transposases completely inactive, and therefore should be avoided.

However, the inventor unexpectedly found that some changes at the strictly conserved nucleotide positions could be compatible with the activity, as selection in nature has not been applied to such variations in the adapters as unpaired nucleotides or modified nucleotides in these conserved positions. Even if such changes may infrequently occur in nature, they would be immediately repaired. Therefore, there is no mechanism to preserve them in progeny. These positions are conserved and therefore are very important for modulating transposase activity, but it should be possible to introduce some changes against which there was no selective pressure and thus modulate the activity. To that end, it is not obvious a priori which nucleotide changes would result in which type of modulation, e.g., higher or lower activity, activity in highly diluted state (low input applications), more likely recognition of AT or GC rich nucleotide sequences, complex stability, activity on solid support, activity in semi-purified or crude samples, as well as degree of manifestation of the above at a variety of in vitro reaction conditions (pH, temperature, $Mn^{++}$ or $Mg^{++}$ concentrations, salt (e.g., NaCl and KCl), glycerol etc.) or contingent upon in vivo application (delivery vehicle, cell type, organelle type). However, in view of the disclosure herein, a skilled artisan would immediately recognize benefits of plurality of suitable adapters at his or her disposal and would design experiments for selecting most suitable adapters contingent upon the project and the specific problem that he or she is wishing to solve. Examples of such projects and experimental designs will be demonstrated below.

An adapter of this invention can have various changes as compared to a native or known recognition sequence for a transposase. The nucleotide position which is the closest to the cut at the transposition event (facing inside the transposon in nature) and which is conserved among the same family of transposases is preferred for modification, for example position 1 as represented in FIG. 1. Positions 2 and/or 3 can also be modified but are less preferred as position 1 is most important for modulating transposase properties as it is adjacent to the cut and is positioned in the catalytic site, for example as represented for Tn5 transposase in FIG. 2. As represented in FIG. 3 for Vibhar transposase and in FIG. 4 for "hyperactive" Tn5 transposase, this position 1 can be modified by substituting one nucleotide on either strand or on both strands for native or modified nucleotide, or by adding at least one native or modified nucleotide to one or both strands, or removing at least one nucleotide from one strand, or by combination of the above.

B. Adapters with Modifications Impeding Primer Extension

In another embodiment, an adapter of this invention has one or more modifications that impede primer extension such as that in a PCR reaction. Such adapters are useful for DNA sample preparations for NGS using transposase.

Conventionally, a DNA sample preparation for NGS involves fragmentation and tagging of target DNA using transposase loaded with oligonucleotide adapters, followed by purification of tagged DNA fragments from unused adapters, and PCR amplification of the fragments. So far it was necessary to purify larger size DNA fragments from much smaller adapters using, e.g., Agencourt Ampure XP SPRI magnetic beads (Beckman-Coulter) or RNA-binding nano-spin columns (Agilent Technologies). Attempts to skip the purification step resulted in either practically no amplification of target DNA or in a very poor yield of desired DNA fragments. Instead, small size by-products (typically less than 100 bp) were produced, possibly comprising adapter-primer dimers. In essence, such PCR reaction is "poisoned" by preferential amplification of these by-products, rather than target DNA fragments.

As disclosed herein, adapters with one or more modifications that impede primer extension allow one to simplify NGS sample preparations by abolishing the above-mentioned purification step after transposase reaction. This makes NGS sample preparation faster, less expensive and more amenable to automation.

General methods and compositions for DNA fragmentation and tagging using transposases are known in the art. See e.g., US patent application 20120301925. For example, a 19 b.p. oligonucleotide comprising a *Vibrio harveyi* (Vibhar) transposase recognition sequence can be "loaded" onto the transposase, which can form a complex with such oligonucleotides/adapters. When mixed with target DNA, loaded transposase cleaves target DNA and tags the fragments (DNA inserts) with adapters as shown in FIG. 13A. In addition to double-stranded 19 bp regions, adapters could contain single-stranded regions that could provide landing sites for PCR primers. As shown on FIG. 13A, PCR Primers AgP1 and AgP2 contain DNA sequences for Illumina flow cell sites P5 and P7.

A typical product of transposase reaction is also schematically represented in FIG. 13A. As shown in the figure, adapters (hybridized oligonucleotides 3ilb/3i0 and 8ilb/8i0) are attached to the ends of the target DNA fragment (DNA insert). DNA insert is connected to the adapters at oligonucleotides 3ilb and 8ilb. It is amplified in PCR using primers AgP1 and AgP2. However, there is a gap on both ends of the DNA insert. This gap is repaired at the PCR step (arrow in the gap), resulting in displacement of 3i0 and 8i0 oligonucleotides. The inventor hypothesized that at the PCR step the displaced oligonucleotides may interact with each other and with AgP1 and AgP2 PCR primers, thus forming adapter-primer dimers. The inventor also hypothesized that since 3i0 and 8i0 oligonucleotides are useful only at the transposase reaction step and have no further use, they could be modified to impede generation of the dimers, as far as such modifications do not impede transposase reaction.

As shown in Example 4 below, at least one modification that stalls DNA polymerase was introduced into at least one strand of adapters. Since Pfu DNA polymerase, which is often used for amplification, stalls on dU residues (Hogrefe et al., Proc. Natl. Acad. Sci. USA, 99 (2), 596-601, 2002.), dU modifications were introduced into adapter pairs 2 and 3 (FIG. 13B). Modifications were introduced downstream of the landing sites of PCR primers AgP1 and AgP2 in order to impede copying of the bottom strand of adapters (oligonucleotides 3U2, 8U2, 3U4 and 8U4) in PCR. Therefore, while adapter copying and amplification is stalled, amplification of target DNA fragment proceeds unimpeded, as after the gap repair, tagged DNA fragments do not contain modified nucleotides. Other modifications that stall polymerases, such as abasic sites or 2'OMe modified RNA that stalls Pfu polymerase can be used by those skilled in the art for this purpose (see, e.g., U.S. Pat. No. 7,659,069). Similarly, any modifications that stall polymerase can be used and can be combined with each other as far as they do not impede transposase reaction.

Another approach can be also used for the same purpose. More specifically, a modified nucleotide can be attached to adapter strand. As shown on FIG. 13B and in Example 4 below, with standard adapter pair 1, oligonucleotides AgP1 and AgP2 serve as templates, and while hybridized to them, oligonucleotides 3i0 and 8i0 serve as primers, thereby generating undesirable by-products in PCR reaction. The inventor hypothesized that this could contribute to generation of adapter-primer dimers. Therefore, 3' ends of the bottom strands of adapters were blocked with Inverted dT to impede this process (FIG. 13B, adapter pair 4). In addition, the inverted dT can be preceded by phosphorothioate bond to prevent removal of the inverted dT by DNA polymerase 3' exonuclease activity. Other approaches, for instance, preceding inverted dT or other 3' blocking group with a spacer, can be used for the same purpose. To this end, many 3' blocking groups could be used in view of the disclosure herein.

Application of oligonucleotide modifications disclosed in this invention is not limited to genomic DNA sample preparation using transposase. They can be applied to eliminate adapter/tag/vector purification steps in other technologies that currently require purification of target nucleic acid fragments from synthetic oligonucleotides in order to perform PCR, e.g., SureSelect, HaloPlex, genomic DNA sample prep using sonication, etc. In particular, single-cell applications could benefit from this invention. No purification step, including SPRI purification, is 100% efficient. Therefore, abolishing the purification step before PCR amplification is beneficial as any losses of initial genomic material are detrimental for genome coverage and result in allele drop-out.

C. Adapters with Phosphorothioate Bonds

In yet another embodiment, an adapter of this invention has one or more phosphorothioate bonds. Such adapters are useful for sample preparation for NGS sequencing or microarray analysis from DNA of a very low initial input, such as from a low number of cells, i.e., one single cell or several cells (e.g., 2, 3, 4, 5, 6, 7, 8, 9, or 10 cells).

In a typical NGS sequencing sample preparation using standard Vibhar adapters and transposase, the adapters contain 19-bp double stranded portions that are recognized by the transposase and also contain single stranded portions that are used as landing sites for PCR primers. See e.g., FIG. 16 and US patent application 20120301925. In transposase reaction, input DNA is cleaved and resulting fragments are tagged at both ends with the adapters. Next, DNA fragments are amplified in PCR using primers complementary to the adapter sequences. At the same time, the fragments are provided with DNA sequences essential for attachment to, e.g., Illumina flow cell binding sites P5 and P7. Vibhar transposase, the adapters design, methods and compositions of forming transposase-adapter complexes, the mechanism of input DNA fragmentation and tagging are known in the art. See e.g., US patent application 20120301925

Figure 17:
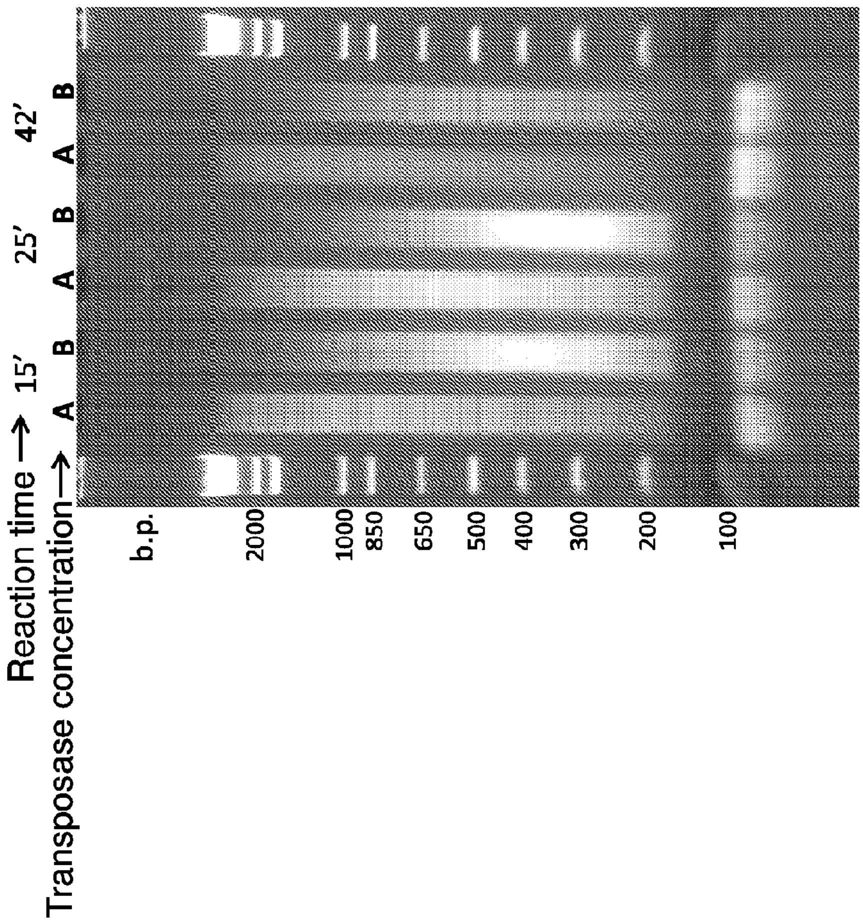
FIG. 17 is a photograph illustrating nuclease activity observed at DNA fragmentation and tagging using standard adapters with 50 ng/ml and 100 ng/ml of transposase ("A" and "B", respectively) for 15, 25, or 42 minutes.

Vibhar transposase preparations contain traces of nuclease activity that could be either originating from the *E. coli* expression host, or (as will be discussed below) weak intrinsic non-specific nuclease activity of the transposase. Although this does not present much of a problem at usual DNA inputs from thousands of human cells, it is unacceptable at a low DNA input. As shown in FIG. 17, with DNA from 3 cells, satisfactory yield of suitable DNA fragments was observed after 25 min of transposase reaction, but the fragments of the desirable size range for NGS (200-500 bp) nearly completely disappeared at 42 min of the reaction. The implication is that even at 25 min of transposase reaction the losses of suitable material could be substantial and may amount to 50% or more, which is unacceptable for NGS sequence with low DNA or cell number input.

It was known in the art that phosphorothioate bonds confer resistance to nuclease attack. See e.g., Stein et al., Nucl. Acids Res., 16:8, 3209-3221, 1988, which is incorporated herein by reference. Including such bonds into adapters could be useful for protection against exonuclease attack as adapters are attached to both ends of the fragments. Yet, a priori, it was not clear if unnatural bonds in the adapters would render adapters inactive in transposase reaction. Indeed, phosphorothioate bonds are not natural and it was observed that DNA containing such bonds is a less efficient substrate for enzymes than DNA containing only natural phosphodiester bonds (Ciafre et al., Nucl. Acids Res., 23:20, 4134-4142).

Figure 18:
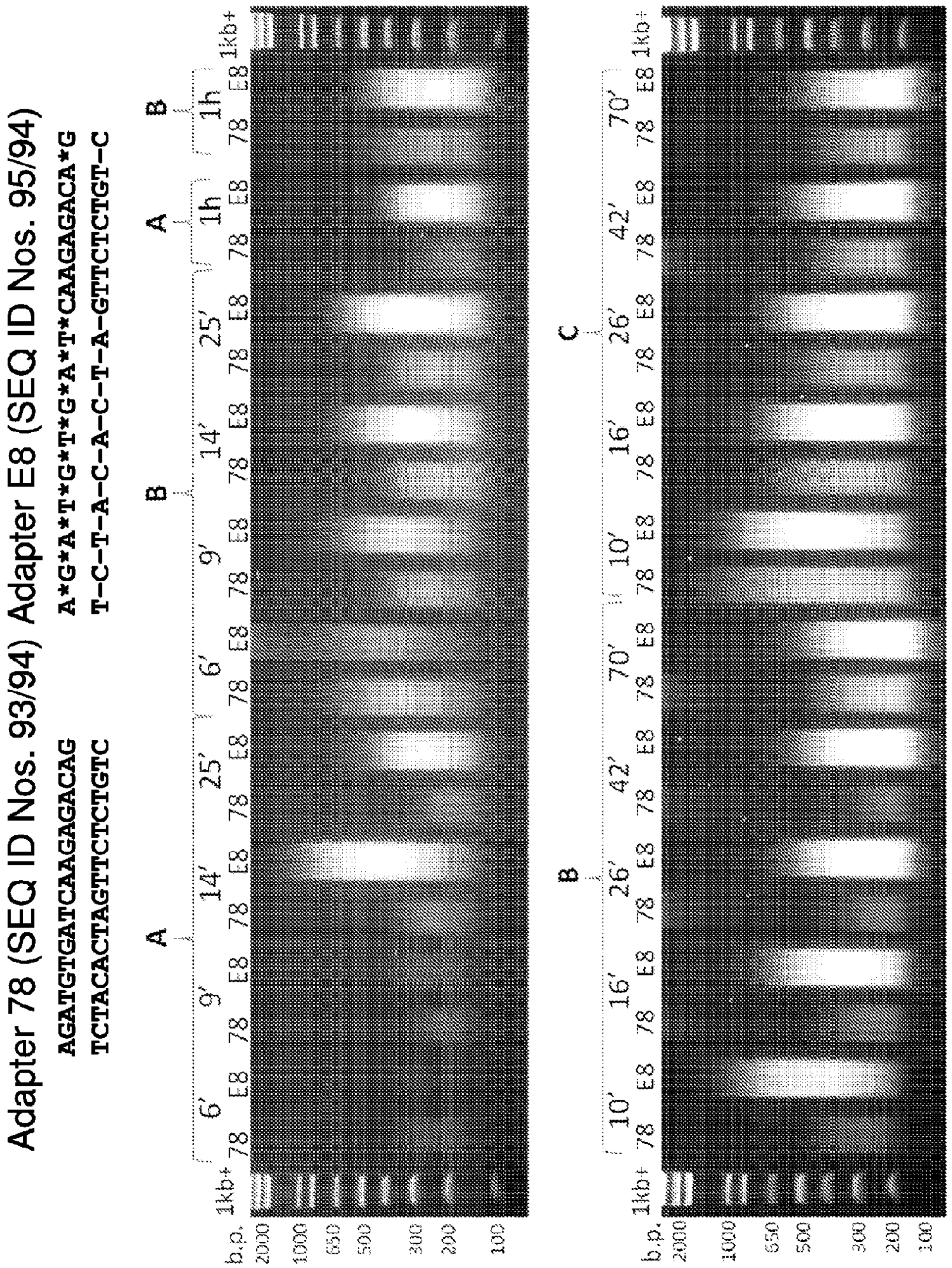
FIG. 18 are photographs showing absence of nuclease activity at transposase DNA fragmentation and tagging using adapter 78, as well as increased transposase activity conferred by its phosphorothioate derivative (adapter E8) at different transposase concentrations, i.e., A-180 ng/ml, B-120 ng/ml, C-80 ng/ml with 20 pg human DNA input (corresponding to ~3 diploid cells).
Figure 21:
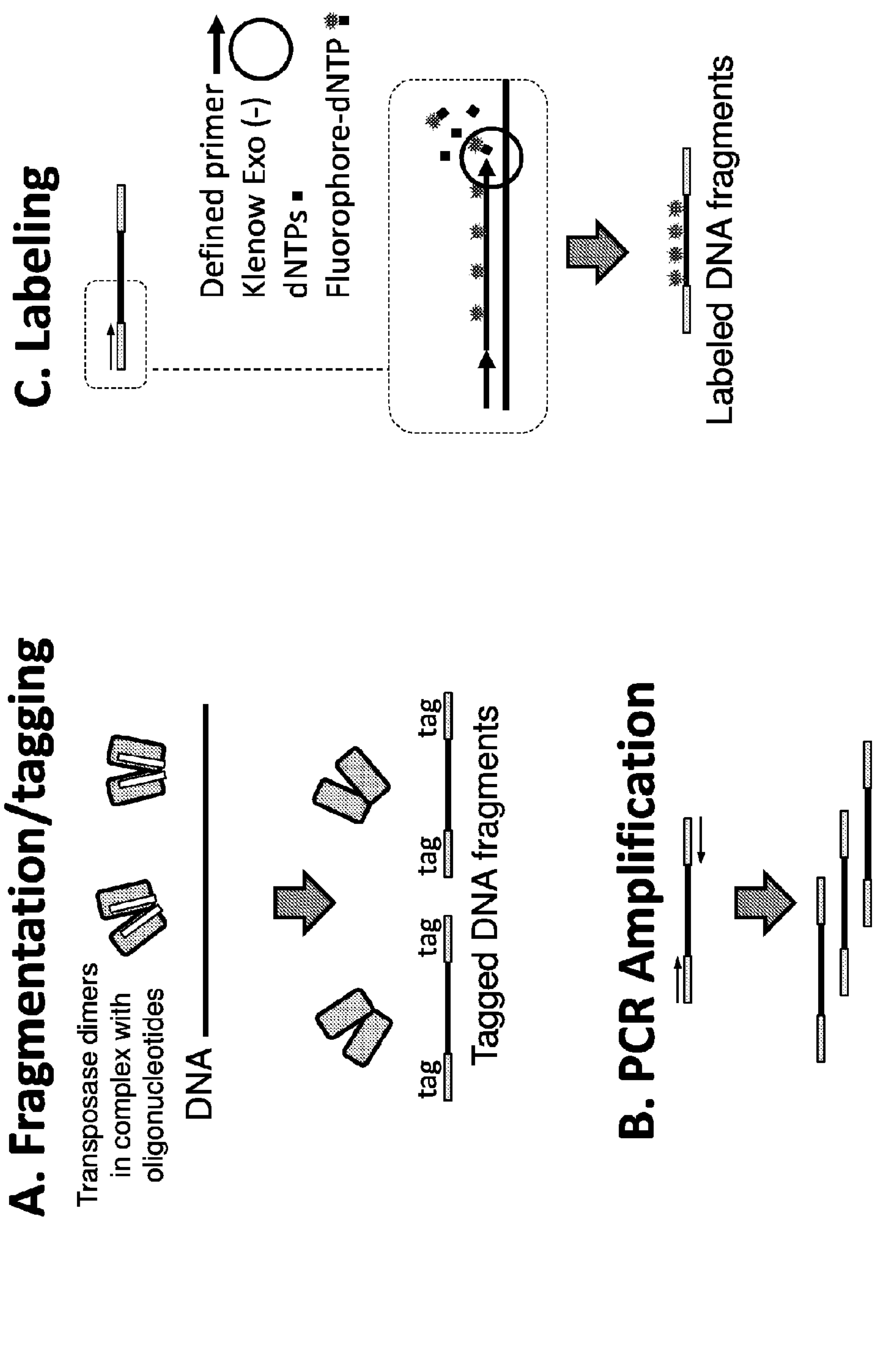
FIGS. 21 A, 21B, and 21C are a set of diagrams showing DNA fragmentation/tagging (A), amplification (B), and labeling (C) in sample preparation for microarrays.

As shown in Example 5 below, phosphorothioate bonds were introduced sparingly into only one strand of the adapters (the transferred strand) in order to confer protection against nuclease without unnecessarily distressing transposase activity. Unexpectedly, it was found that a combination of phosphorothioate bonds (e.g., adapter E8) conferred large improvement in transposase reaction efficiency (FIG. 18).

Since only the transferred strand of an adapter is attached to the DNA fragment, phosphorothioate bonds are introduced into that strand, and the complementary adapter strand that is separated by a gap from the target DNA fragment does not contain phosphorothioate bonds. Those strands without phosphorothioate bond will not be protected because as disclosed herein it is beneficial to render these strands unsuitable for PCR amplification.

Improvement was consistently observed in several experiments at different transposase concentrations as well as at different incubation times. However, for the most part this improvement was not related to protection against nucleases. Indeed, practically no nuclease degradation was observed with short adapter 78 that has the same nucleotide sequence, but does not contain phosphorothioate bonds (FIG. 18). Unlike the standard adapter, adapter 78 and its phosphorothioate derivative E8 consist only of 19 bp duplex that is recognized by the transposase, bound by the transposase and is likely to be largely hidden and protected from the nuclease attack. It is possible that the nuclease activity recognizes single-strand portion of standard adapters and flips over to the interior of the DNA fragment which it digests. Protein of a substantial size, e.g., transposase dimer (MW~102 KD), would be required for such maneuver. It seems unlikely that indigenous nucleases from *E. coli* are responsible for the DNA degradation since they are small in size, *E. coli* is well studied and no such activity was described in *E. coli*. Whatever the mechanism, from a practical standpoint it is important that efficiency of transposase reaction can be largely improved by adding phosphorothioate bonds to the adapters.

As discussed herein, a several-fold improvement in efficiency of transposase reaction is necessary for nearly complete genome coverage of a single cell genome. The modified adapters of this invention allow one to achieve this improvement. To further improve the efficiency, one can adopt additional means including re-shuffling, adding or removing phosphorothioate bonds, as well as other modifications to the adapters as disclosed herein. The procedure can be also adapted for microarray applications and provide tags necessary for sequencing on Illumina or other types of instruments by either adding such tags in PCR or in DNA-ligase reaction. By the way of example and not a limitation some of such adapters and PCR primers for providing Illumina tags are represented on FIGS. 19 and 20.

The above-disclosed adapters address the need in the art for sequencing nucleic acids from a low number of cells, such as a single cell. Single-cell sequencing holds promise for better understanding, diagnosis and treatment of several forms of cancer. However, despite rapid progress in this field, there was a consensus that there are high error rates in all the methods and none of them are good enough. One of the problems is that small amount of DNA that is obtained from single cells is not directly processed (fragmented and tagged) for sequencing or microarrays. First, it is amplified in whole genome amplification (WGA) in which highly processive polymerase is used in combination with degenerate primers to generate more DNA and only then the amplified DNA is processed (Zheng et al., J Zhejiang Univ Sci B. 2011 January; 12(1):1-11; Hou et al. Cell. 2013 Dec. 19; 155(7):1492-506).

It is generally accepted that most of the errors are generated at the WGA step. First, mistakes are generated at polymerase reading, but even more importantly some regions of the genome are amplified more efficiently than others and some are not amplified at all. This generates bias that complicates analysis of gene copy numbers. Even worse, it results in allele dropout. For this reason single-cancer cell genome sequencing is rarely attempted from chromosomal DNA. Instead, sequencing or microarray analysis of transcriptomes of cancer cells is performed. Concentrating on the transcriptomes alleviates the allele dropout problem since genes are often represented by multiple mRNA copies (Lawrence et al. Nature. 2013 Jul. 11; 499(7457):214-8). However, this yields information mostly on protein coding regions of cancer cells, but not on the gene regulatory regions, e.g., promoters, enhancers and silencers. And, this does not address the need in the art since large portion of genetic and epigenetic variations responsible for complex traits such as predisposition to most forms of cancer and other wide spread complex diseases are localized in the non-coding, regulatory regions (Mitchison A. Immunogenetics. 1997; 46(1):46-52; Gaffney et al., Genome Biology, 2012, 13:R7, 1-15; Knight J C. Clin Sci (Lond). 2003 May; 104(5):493-501; Savinkova et al., Biochemistry (Mosc). 2009 February; 74(2):117-29; Wang et al., Carcinogenesis. 2013 May; 34(5):1012-7; Elahi et al., Biochim Biophys Acta. 2009 March; 1792(3):163-72; Ruiz-Narváez E A. Med Hypotheses. 2011 May; 76(5):638-42; Zabaleta J. Methods Mol Biol. 2012; 863:411-35; Susantitaphong et al., Nephron Clin Pract. 2012; 122(3-4):107-13; Itzykson R, Fenaux P. Leukemia. 2013 Nov. 19. doi: 10.1038/leu.2013.343]; Vezzoli et al. J Transl Med. 2011 Nov. 22; 9:201; Martini et al., Diabetes. 2013 July; 62(7):2605-12; and Clark S J. Hum Mol Genet. 2007 Apr. 15; 16 Spec No 1:R88-95).

Due to technical limitations of conventional approaches, wealth of gene regulatory information that is most pertinent both to cancer development and predisposition to other wide spread complex diseases remains inaccessible with the focus on transcriptomes because gene promoters are not sequenced. Sequencing transcriptomes provides information on abundance of transcripts which can be correlated with a disease, a.k.a. expression quantitative trait loci (eQLTs). However, in the same individual gene expression profiles widely differ from one cell type to another, and expression profiles of cells that are easily available, e.g., lymphocytes are often not useful. For instance, more than 50% of all gene expression traits in adipose tissue strongly correlated with clinical traits related to obesity, compared to less than 10% in blood (Emillson et al., Nature, 2008, 452:423-430). Furthermore, biopsies of most pertinent cells, e.g., brain cells at Alzheimer's may not be available. Though it is understood that direct sequencing of genomic DNA would address these problems, currently it is not practical because of the state of the conventional single-cell genomes sequencing technologies.

In addition to sequencing genomes of individual cancer cells, another application of single-cell sequencing is in non-invasive pre-natal diagnostic (NIPD). Analysis of single nucleated erythrocytes of the fetus isolated from mother's blood holds promise for over a billion dollars NIPD market (Kantak et al., Lab Chip. 2014 Mar. 7; 14(5):841-54). Presently the largest commercial application of "small cell number" technologies is in rapid preimplantation genetic diagnosis (PGD) (Harper et al., Eur J Hum Genet. 2013).

PGD is most commonly performed either from 1-2 cells at the $3^{rd}$ day of embryo development or from about 5 cells at the $5^{th}$ day (blastocyst). Lately the blastocyst approach was gaining more popularity as it is more reliable, i.e., less allele dropout problem with material from more cells, less mosaicism at the blastocyst stage, and less damage to the embryos since trofectoderm cells (predecessors of placenta cells), rather than embryo cells are taken (Harper and Sengupta. Hum Genet. 2012 February; 131(2):175-86). In the past the analysis was performed exclusively using PCR and FISH technologies (ibid), with the current switch to microarray and further to NGS technologies (Yin et al., Biol Reprod. 2013 Mar. 21, 88(3):69; and Zhang et al., PLoS One. 2013, 8(1):e54236.). Both microarray and NGS methods require WGA since there is not enough material from 1-5 cells to perform the analyses. However, WGA is not only the main source of bias that complicates copy number variation (CNV) estimates, it is also the major allocation of time in PGD workflow. Given the timeliness nature and challenge of PGD, there is a need for a technique that is faster and provides comparable or better performance as compared to WGA.

A tempting solution to these problems is direct processing (fragmentation and tagging) of DNA from single cells thus avoiding WGA methods altogether. However, widely used fragmentation by sonication is unsuitable for this purpose because of the difficulty of subsequent ligation of oligonucleotide tags to the fragments at extremely low DNA concentrations. To the contrary, fragmentation and tagging of DNA in a transposase method occurs simultaneously, in one step, which seems to offer a solution. In addition to having one step instead of two, transposase reaction is essentially a 2-component reaction, and is inherently much more efficient than a 3-component ligation process as in WGA. Libraries from single cells suitable for sequencing on Illumina instruments can be generated within minutes using Vibhar transposase. Though prospectively offering faster and more economical processing of the samples, so far this approach was plagued with the same problems as WGA methods because of insufficient efficiency of transposase reaction at low DNA inputs. Indeed, as shown in the examples below, with DNA inputs from single to several cells, only minority of input DNA material was processed in a standard transposase reaction. Therefore, improved efficiency (i.e., improved output/input ratio) of the transposase reaction is needed for developing a "WGA-less" single cell method of sample preparation for NGS and microarrays.

DNA sample preparation for NGS involves fragmentation and tagging of target DNA in transposase reaction, followed by PCR amplification of the fragments. Similarly, transposase can be used in preparation of DNA samples for microarray analysis of genomic aberrations. At most widely used DNA inputs from thousands of human cells (10-50 ng DNA) a single HiSeq run provides adequate genome coverage and relatively low duplication rate (over 90% and below 6% respectively). However, genome coverage is dramatically reduced if DNA from single cells or from several cells is processed directly in transposase reaction without WGA, and the duplication rate rises accordingly. For instance, DNA input from 3 human cells genome generally gives rise to only 42% coverage, but a duplication rate of 72%.

The adapters of disclosed herein allows one to improve performance of transposase-based DNA preparation at low DNA input by several folds so that he or she can achieve comparable or better sequencing coverage at even a single cell input. This improvement in efficiency allows WGA-less processing of genomic DNA at very low input (e.g., samples from single to several cells or individual chromosomes) for NGS and microarray analysis. In addition it also leads to better genome coverage and reduced bias at higher genomic DNA and cDNA inputs.

The adapters disclosed herein can also be used in sample preparation for microarray application. Despite the fact that sample preparation for NGS and for microarrays has common steps that can be facilitated with transposase technology, so far transposases were not used in sample preparation for microarrays. Apart from NGS and microarray, the transposon adapters of this invention can be also used for mutagenesis, in gene therapy and in generating pluripotent cells for regenerative medicine (Palazzoli et al. Geneteca, 2010, 138(3):285-99).

D. Additional Adapter Modifications

By the way of example and not a limitation, examples of modified nucleotides comprise 2-Aminopurine, 2,6-Diaminopurine, 5-Bromo dU, deoxyUridine, Inverted dT, Inverted Dideoxy-T, Dideoxy-C, 5-Methyl dC, deoxyInosine, Universal base such as 5-Nitroindole, 2'-O-Methyl RNA bases, Iso-dC, Iso-dG, Ribonucleotide, Morpholino, Protein nucleitide analogues, Glycoic nucleotide analogues, Locked nucleotide analogues, Threose nucleotide analogues, Chain terminating nucleotide analogues, Thiouridine, Pseudouridine, Dihydrouridine, Queuosine, Wyosine nucleotides. These can be incorporated or added to the native adapter sequence, to a modified adapter sequence, e.g., "mosaic" or to the above modifications.

Furthermore, useful modifications do not necessarily comprise modified bases. For example, they can comprise abasic sites; functional groups, e.g., alkyne functional group, azide functional group such as azide (NHS Ester); unnatural bonds, e.g., phosphorothioate bonds; spacers, e.g., 1',2'-Dideoxyribose (dSpacer), Hexanediol, photo-cleavable spacer, different length spacers with different number of carbon atoms, e.g., C3 spacer phosphoramidite, C9 spacer, e.g., a triethylene glycol spacer, C18 an 18-atom hexaethyleneglycol spacer, etc. Such spacers can be incorporated at the 5'-end or 3'-end of an adapter or internally. Furthermore, at least one strand of an adapter of this invention could be modified by phosphorylation, i.e., comprising either 5' phosphate at position 1 as represented in FIG. 1, or 3' phosphate in the same position, but on the complementary strand, or both. Oligonucleotides with or without the above modifications can be custom-made by several suppliers, e.g., Integrated DNA Technologies (Coralville, Iowa), TriLink (San Diego, Calif.), Eurofins MWG Operon (Huntsville, Ala.), GenScript (Piscataway, N.J.). As used herein, a "spacer" refers to a molecule or group of molecules that connects two moieties. A typical spacer may include bonds such as those selected from alkylene (carbon-carbon), ether, amino, amide, ester, carbamate, urea, and keto, and combinations thereof. A spacer may include short alkylene moieties alternating with, or flanked by, one or more types of heteroatom-containing linkages. Non-limiting examples include but are not limited to $-CH_2OCH_2CH_2CH_2-$, $-CH_2C(O)NHCH_2-$, $-C(O)OCH_2-$, $-OC(O)NHCH_2CH_2-$, $-CH_2CH_2NHCH_2$, $-CH_2CH_2C(O)CH_2CH_2-$, $-CH_2CH_2CH_2C(O)NHCH_2CH_2NH-$, and $-CH_2CH_2CH_2C(O)NHCH_2CH_2NHC(O)CH_2CH_2-$ and the like. The spacer moieties may be hydrolytically stable or may include a physiologically hydrolyzable or enzymatically degradable linkage (e.g., an ester linkage).

Modifications on the bottom strand of adapter (FIGS. 3 and 4) do not need to be necessarily suitable for recognition by DNA repair enzymes, e.g., polymerases, kinases and ligases as transposase leaves a gap after cleaving target DNA and modified adapter can be displaced, for example during gap repair step, resulting in double-stranded unmodified DNA suitable for in vitro and in vivo applications. In view of the disclosure herein, skilled artisan would immediately recognize that contingent upon the application, different oligonucleotide sequences can be attached to such adapters, e.g., the sequences that are necessary for attachment to Illumina chips (US Application 20120301925). Furthermore, in view of the disclosure herein, skilled artisan would immediately recognize a potential for modifying transposase properties by modifying adapter sequences at the transposase active site and for selecting adapters with improved properties for a particular need.

In addition to the recognition sequence regions, typically an adapter of this invention comprises at least one other region, which can be designed for primer binding for amplification or other polymerization reactions. The primer binding regions can be double-stranded or single-stranded and can be designed to include any suitable primer binding sequence. It is a routine task for the skilled artisan to design a primer binding sequence and corresponding primer, and it is left to the practitioner to devise suitable sequences for use in primer binding, extension and amplification, e.g., PCR, multiple displacement amplification (Lasken R S. Biochem Soc Trans. 2009 April; 37(Pt 2):450-3), multiple annealing and looping-based amplification cycles (Zong et al., Science. 2012 Dec. 21; 338(6114):1622-6.), etc.

The adapter can further comprise one or more double-stranded DNA (dsDNA) or single-stranded DNA (ssDNA) sequences (also referred to herein as "tags"). The tags can be included to allow attachment of generated DNA fragments to sequencing chips, such as Illumina chips, and allow identification of the source of the target DNA library, such as Index sequences.

In one aspect, the adapter has a tag containing a degenerate base region (DBR), which can be subsequently sequenced (e.g., after certain process steps are performed, e.g., amplification and/or enrichment). The number of different DBR sequences present in a sequencing run can be used to determine/estimate the number of individual polynucleotide molecules originating from the same genomic region of the same original sample that have been sequenced in a particular sequence analysis configuration or process. DBRs can be used to improve the analysis of many different nucleic acid sequencing applications. For example, DBRs enable the determination of a statistical value for an allele call in genotyping assays that cannot be derived from the read number alone.

A DBR is a region that can have a variable base composition or sequence (which may be considered as "random") as compared to other tagged polynucleotides in the sample. The number of different DBRs in a population of polynucleotides in a sample will be dependent on the number of bases in the DBR as well as the potential number of different bases that can be present at each position. For example, a population of polynucleotides having attached DBRs with two base positions, where each position can be any one of A, C, G and T, will have potentially $2^4$ or 16 different DBRs (AA, AC, AG, etc.). DBR may thus include 1, 2, 3, 4, 5, 6, 7, 8, 9, 10 or more bases, including 15 or more, 20 or more, etc so as to give rise $2^1$ to $2^{20}$ or more different permutations. In certain embodiments the DBR is from 3 to 10 bases in length. Moreover, each position in a DBR may have a different base composition. For example, a 4 base DBR may have any of the following compositions: NNNN; NRSN; SWSW; BDHV. It is further noted that in certain embodiments, a base in a DBR may vary by virtue of having a detectable modification or other moiety attached thereto. For example, certain next generation sequencing platforms (e.g., Pacific Biosciences™) can be used to detect methylation differences in bases during the sequencing process. As such, a non-methylated base in a DBR could be distinguished from a methylated base in a DBR. No limitation with regard to the length or base composition of a DBR is therefore intended.

A DBR may be a single region (i.e., having all nucleotide bases adjacent to one another) or may be present in different locations on a polynucleotide (i.e., the bases of the DBR are separated by non-DBR sequences, also called a split DBR). For example, a DBR may have one or more bases in a first adapter at a first location on a polynucleotide and one or more bases in a second adapter at a second location on the same polynucleotide (e.g., the DBR may have bases present at both ends of an asymmetrically tagged polynucleotide, i.e., a polynucleotide having asymmetric adapters). No limitation in this regard is intended.

Generating adapters having a DBR may be achieved in any convenient manner, e.g., using DNA synthesis methods well known in the art. Once attached to the polynucleotides in the parent sample, the polynucleotides may be subjected to further processing and ultimately sequenced. Processing steps that may be performed include any process steps that are desired by a user, e.g., enrichment, amplification, and the like. In the sequencing step, the sequence of the DBR as well as a portion of the polynucleotide (e.g., containing a region of interest) is obtained. Once the sequences are obtained, the number of different DBRs attached to a polynucleotide of interest is determined. This number can be employed to determine, or estimate, the number of different polynucleotides of interest from the starting parent sample that are represented in the sequencing results, where in some embodiments, the determined number is the minimum number of different polynucleotides of interest from the starting parent sample that are represented in the sequencing results.

As mentioned above, the adapters of this invention are particularly suitable for fragmenting DNA from samples having very low amounts of DNA for NGS or microarray analysis. Conventional approaches for this early stage of sample preparation can result in a high coverage of reads all corresponding to one allele, and that this can occur many more times than should be expected according to the binomial distribution. This is due to amplification of a few molecules of DNA (or even a single molecule) that results in a large number of reads derived from a genetic locus on a single chromosome (i.e., only one of the two diploid chromosomes actually present in the sample of interest). The result of this is that the error as a function of coverage deviates wildly from the predicted binomial error. Using a DBR can increase the confidence in making allele calls from samples having limited amounts of DNA. For example, if 16 sequencing reads of one allele from a genetic locus all contain the same DBR sequence, it is likely that all these reads are from the same parent polynucleotide molecule (and thus a homozygous allele call is not justified). However, if the 16 sequencing reads each have a different DBR sequence, a homozygous call can be made with more confidence, as each read came from a different parent polynucleotide molecule.

DBR domains in genetic analysis are powerful when combined with NGS platforms, many of which provide sequence data for each individual polynucleotide present in the sample to be sequenced. In contrast to conventional sequencing approaches in which individual clones of polynucleotides are sequenced independently, NGS platforms provide sequences for multiple different polynucleotides in a sample simultaneously. This difference allows for sample-specific statistical analyses to be done which are not constrained by having to clone and independently sequence each polynucleotide. Thus, the DBR domain analyses described herein synergize with the modified adapters of this invention and NGS platforms, providing improved statistical approaches to analyze the very large amounts of sequence data from pooled samples. In addition, DBR sequences can be used in other analyses, such as statistical validation of sequence variants in a heterogeneous sample, including complex genomes or pools. For example, DBRs find use in the analysis of complex genomes in tumor samples, microbial samples, environmental samples, etc. See, e.g., U.S. Pat. No. 8,481,292, the content of which is incorporated by reference.

For the purpose of applicability to next generation sequencing, it is preferred that about a half of the adapter ends are tagged with one type of tag and another half with a different tag, such that after transposase-mediated fragmentation of a target DNA, one kind of tag is attached to one end of the target DNA fragment, and another type to the opposite end to allow reading of a DNA fragment in both directions. The inventor has recognized that improved DNA fragmentation for preparation of fragments for further analysis (i.e., improved randomization of fragmentation) can be achieved by combining two different transposase recognition sequences, i.e., that some (e.g., about 50%) of the adapters in a particular composition comprise a first recognition sequence for a transposase and the remaining adapters comprise a second, different recognition sequence. The recognition sequence can be a naturally occurring sequence for the transposase, or can be an engineered sequence that provides additional or alternative functions for the adapter.

In exemplary embodiments, the recognition sequence differs for each end of the target DNA to be fragmented. In some embodiments, the two sequences at the ends of a target DNA fragment can be identical or substantially identical, having at least 90% (i.e., 90%-100%) sequence identity with each other. In some other embodiments, the two sequences are different, having less than 90% (i.e., 89% or less, a minimum being about 30%) identity with each other. However, it is preferred that both recognition sequences are recognizable by the transposase being used in conjunction with them to about the same degree. To this end, the efficiency of transposase fragmentation can be assessed separately for several recognition sequence and recognition sequences with practically the same efficiency are selected for use together. Alternatively, less efficient adapters can be mixed with more efficient adapters, whereas the latter are used in smaller amounts than the former. In exemplary embodiments, the recognition sequences comprise both natural and modified sequences such as those shown in FIGS. 1 and 3-5. Furthermore, a single type of natural or modified recognition sequence can be used, or simultaneously two or more types of natural or modified recognition sequences, in any combination, can be used. One of skill in the art can use any transposase and easily discern its recognition sequence, as recognition sequences are known to be present as IRR and IRL repeats flanking transposase genes.

One skilled in the art will recognize that any nucleotide sequences can easily be attached to the recognition sequences during oligonucleotide synthesis or by other methods, e.g., using DNA ligase. Such sequences can provide landing sites for sequencing primers and for PCR primers in order to amplify DNA fragments and also serve the purpose of attaching the DNA fragments to DNA sequencing chips, such as Illumina chips. Additional nucleotide sequences are preferably single-stranded or mostly single-stranded; otherwise the transposase might be inhibited, as it would recognize excessive dsDNA as a substrate. Though to a much smaller degree, attachment of single-stranded extensions can also reduce transposase activity, therefore it is preferable to keep the size of the attachments to a minimum. To this end, use of two different recognition sequences is advantageous by allowing landing sites for primers can be extended into the part of the recognition sequences that differs between the two (see, e.g., US Patent Application 20120301925, the content of which is incorporated by reference). This design allows for the use of only two primers for PCR amplification of DNA fragments as compared to four primers in the NEXTERA™ system, which uses the same transposase recognition sequence for both adapters. The use of two, rather than four, primers is an advantage of the prior system in that it is simpler and more efficient in PCR amplification.

To make the adapters, the adapters are designed to specifically bind to the transposase(s) being produced. As such, the recognition sequence that must be present on each adapter is known before synthesizing the adapters. Natural recognition sequences often constitute inverted repeats that can be found 50-200 nucleotides upstream and immediately downstream of a transposase open reading frame and can be identified in the genome sequences by those skilled in the art. The adapters can be made using any suitable technique, including chemical synthesis. The adapters include at least a portion that is double stranded. As such, prior to use it is preferred that the two complementary portions be exposed to each other under conditions whereby hybridization occurs to produce the double-stranded portions.

In some embodiments, an adapter of this invention includes a member of a specific binding pair. The member can be covalently attached to the nucleic acid of the adapter and allows for specific binding to the other member of the specific binding pair. In exemplary embodiments, the other member of the specific binding pair can be attached to a solid substrate. In this way, the adapter can be specifically bound to the solid substrate, which facilitates, for example, purification of a corresponding transposase and use of the adapter-transposase complex to produce solid-substrate bound transposase cleavage products (e.g., DNA fragments for amplification/characterization). In generally, attachment of a binding pair member, e.g., biotin, via the 5' end of one strand of an adapter is preferred. However, binding pair member(s) can also be attached to the 3' end or to both 3' and 5' ends that are distant from the DNA insert so as to avoid inhibiting activity of transposase complexes.

As mentioned above and exemplified below, the synthetic adapters of this invention differ from known functional transposase adapters (native or modified) at the most conserved sites, but unexpectedly retain the activities. Even more surprisingly, some of them have even higher activities, resulting in increased randomness or reduced duplication rate or both when used for NGS.

In some embodiments, it was demonstrated that a plurality of useful adapters conferring different properties to a transposase of choice can be generated by modifying conserved position 1 in native adapter. Skilled artisan can use this for creating a plurality of adapters for a transposase of choice and applying a plurality of adapters for optimization of transposase properties contingent upon the transposase application, as well as contingent upon impurities that may be present in the samples, e.g., selecting the best adapters for unpurified serum or semi-purified blood samples, for single-cell genome sequencing, for sequencing DNA from formalin fixed paraffin-embedded slides, . . . etc.

Increased activity is useful for numerous applications, especially for low DNA input reaction conditions, e.g., when there is a need to analyze samples with low DNA concentrations. For example, single-cell genome sequencing is of particular interest for understanding mechanisms of cancer development and anti-cancer drug discovery. It is widely recognized that ability to sequence miniscule amounts of DNA, starting from as little as an equivalent of DNA from a single human cell, and with as few amplification cycles as possible, would be highly advantageous for development of personalized medicines, companion diagnostics and overall understanding of cancer (Navin and Hicks, Genome Medicine 2011, 3:31). Furthermore, DNA input of less than an equivalent of a human cell is desirable for some applications, e.g., for sequencing isolated chromosomes or small genomes (Giorgi et al., PLoS One. 2013; 8(2):e57994. doi: 10.1371/journal.pone.0057994).

One of the major applications for low DNA input is genome sequencing of single isolated cancer cells that are responsible for metastatic activity, rather than their mixture with "passenger cells" in the tumor. This should enable better understanding of cancer and lead to improved cancer treatments and diagnostics. Sequencing individual cell genomes is necessary because relatively few tumor cells are responsible for cancer development and its spread (metastasis) in a patient. Majority of cancer cells are just "passenger cells", and often analysis of a tumor sample does not give an answer about mutations that are causative to cancer because predominantly background, "passenger cells" genomes are sequenced in a library generated from a mixture of tumor cells. Current methods of single-cell genome sequencing typically require whole genome amplification with subsequent sample preparation from the amplified DNA. Using this approach large (microgram) amounts of DNA can be generated from a single cell and processed for NGS. However, this results in only partial sequence coverage of single-cell genome due to selective amplification. Therefore, there is a need to generate libraries for NGS directly from single-cell DNA, and higher activity transposases that can process (fragment and tag) extremely small amounts of DNA at low DNA concentration are desirable.

Another application is analysis of free DNA from human blood. Cancer cells that are responsible for metastasis are detached from tumor, they are fragile and their DNA is often present in blood, though often at low concentrations. A separate application is analysis of free DNA in blood of pregnant women. Such DNA could be originated from fetus and its analysis would be valuable for the diagnosis of inherited diseases or predisposition to complex diseases (Papageorgiou and Patsalis, BMC Med. 2013, 11(1):56). Furthermore, low input methods could be applied for detection of infectious agents in human blood, food or in environmental samples. Yet another application relates to understanding complex ecological systems. Without single-cell NGS technologies only partial analysis of microbes in human microbiome or in environmental samples is feasible because many microbes currently can't be cultivated outside their environment (Fodor et al., PLoS One. 2012; 7(7): e41294. doi: 10.1371).

Transposase-Adapter Complexes and Related Compositions

The invention further provides complexes of the above-described adapter and transposase and compositions comprising the complexes.

Various transposases can be used to make the complexes. They can be any protein having transposase activity in vitro, such as a naturally occurring transposase or a recombinant transposase. The transposase can be isolated or purified from its natural environment (i.e., cell nucleus or cytosol) at least to some extent. Preferably, the transposase is recombinantly produced, and preferably is isolated or purified from the recombinant host environment (i.e., cell nucleus or cytosol). Most preferably, the transposase is purified away from other cellular components to a level of 90% or greater prior to inclusion in compositions of the present invention. Preferably, the transposase is at a level of about 95% or greater, such as about 98% pure, about 99% pure, or greater than 99% pure. Purity is determined based on common techniques for determining purity, such as by Coomassie blue staining, silver staining, HPLC, mass spectrometry, or other sensitive techniques for detecting impurities in protein samples. DNA impurities can also be assessed, e.g., using PCR. In exemplary embodiments, the transposase is a transposase with a "cut and paste" mechanism of transposition (Yuan and Wessler, Proc Natl Acad Sci USA. 2011 May 10; 108(19):7884-9), and is a member of the IS4 family of transposases, such as one that is naturally found in *Vibrio* species, including, but not limited to, *Vibrio harveyi*. In embodiments, the transposase is not the Tn5 transposase or a transposase derived from the Tn5 transposase, for example by mutagenesis of the wild-type Tn5 transposase.

Transposases are considered isolated or purified when they are found in an environment that is different than the environment in which they exist in nature or in which they were produced. For example, they can be in an environment in which some or all of the other biomolecules of the cell in which they are produced are removed. The transposases are recombinant if they are produced in a cell that is not the cell in which they are naturally found, and are modified if they have amino acid sequences that differ from the naturally-occurring sequence(s) of the transposase(s) from which they derive or originate. For example, a transposase according to the invention can have the amino acid sequence of a naturally-occurring transposase (wild-type), or of a modified transposase that has one or more naturally-occurring amino acids deleted or replaced with a different amino acid, or a modified transposase can have amino-acid sequences added to the wild-type sequence. In addition, the naturally-occurring amino acid sequence can be disrupted by addition of one or more amino acids at one or more sites in the sequence. In some embodiments, the transposases are chimeric proteins, i.e., they are proteins that include a mixture of amino acid sequences from two or more different transposases.

The complexes may comprise one or more transposase molecules and one or more adapters. In complexes that comprise at least two transposases, at least two of the transposases are bound to a nucleic acid or oligonucleotide adapter. In embodiments where the complex comprises two transposases, the complex can represent a form similar to a synaptic complex. Higher order complexes are also possible, for example complexes comprising four transposases, eight transposases, or a mixture of different numbers of sizes of complexes. In complexes comprising more than two transposases, not all transposases need be bound by an oligonucleotide. Rather, it is sufficient that two of the transposases are bound, although additional oligonucleotides may be bound. Usually, where two or more transposase molecules are present in a complex, the same transposase is employed in the complex. However, in some embodiments, it is preferred that two or more different transposases are employed in a single complex. For example, one or more of the transposase molecules in the complex could be rendered partially or wholly inactive via modification of their amino acid sequences, and a mixture of active and partially or wholly inactive transposase molecules could be used to modulate the distance between active subunits, and consequently the average size of DNA fragments produced by the complex. Likewise, different complexes having different recognition sequences can be used, such as, for example a complex comprising a transposase with a recognition sequence for high GC sequences and another transposase with a recognition sequence for a sequence having lower GC content. Mixing of transposases having different GC and AT content in recognition sequences allows for tailoring of fragmentation patterns for target DNA sequences. Although one type of oligonucleotide adapter can be used to fragment DNA, in embodiments where fragmentation is followed by amplification and sequencing of the fragmented DNA, use of at least two kinds of oligonucleotide adapters is preferred to facilitate PCR amplification of the DNA fragments and to provide different landing sites for different DNA sequencing primers that are used to sequence the DNA fragments in both directions. One or more transposase recognition sequences can be used to design adapters, as unlike some restriction endonucleases transposases are not necessarily limited to one exact recognition sequence.

The transposases can be present in compositions, which comprise at least one other substance in addition to the transposase. The compositions are not particularly limited in the number and type of substances present. In general, liquid compositions comprise water and the complexes. Typically, one or more other substance is present, such as a salt, an ion, a buffering compound, a metal, or one or more biomolecules. In general, any number of substances can be included in the compositions. The identity, number, and amount of the various additional components will typically be dictated by the application for the composition or the specific requirements for a particular transposase complex for optimal activity.

In certain embodiments, the compositions comprise two or more different transposases. The nature and number of other substances is not particularly limited. In many embodiments, the compositions comprise at least water, although certain embodiments are directed to frozen compositions or dried (e.g., freeze-dried) compositions. In exemplary embodiments, the compositions comprise a transposase in cell lysates or in DNA fragmentation reaction mixtures, which, in embodiments are supplemented with EDTA and/or oligonucleotides. EDTA chelates divalent cations, thus inhibiting host cell nucleases, which typically require $Mg^{2+}$ ions for their activity and otherwise would degrade the oligonucleotides. The fact that formation of the transposase-oligonucleotide complex does not require divalent cations allows for the addition of EDTA or other nuclease inhibitors to crude cell lysates without disruption of the formation of, or maintenance of, the complex.

In some embodiments, a composition of this aspect of the invention comprises adapters bound to purified transposases or transposases in cell lysates of cells in which the transposases are produced (and to which adapters have been added before or after cell lysis). Purified transposase-adapter complex compositions, whether the complex is free in solution or bound to a solid substrate, can also be included in enzymatic reaction compositions, such as DNA cleavage/fragmenting reactions. Non-limiting exemplary substances that can be present in such compositions include: target DNA to be cleaved by the transposase complexes, oligonucleotide primers for polymerization of target DNA fragments; one or more DNA polymerases; restriction endonucleases; DNA modifying enzymes; polysaccharides; lipid membranes; nanoparticles; beads, including magnetic beads; transfection reagents; and detergents.

A transposase-adapter complex of this invention can be attached to a solid substrate or support. The terms "solid substrate" and "solid support" are used in accordance with their meaning in the art. They are thus any material known in the art as suitable for binding and retaining nucleic acids under conditions of purification and/or enzymatic reaction. Those of skill in the art are well aware of suitable materials to use as solid substrates. Non-limiting examples of solid substrates useful in the present invention include: nylon, yttrium silicate (YSi), and polyvinyltoluene (PVT) beads, including magnetic beads (see, e.g., Dorgan et al., Journal of Magnetism and Magnetic Materials, Vol. 194: p. 69-75, 1999); nylon, nitrocellulose, or PVDF membranes; and plastic surfaces, such as those comprising polystyrene or polypropylene, the latter found on plates or wells for PCR amplification of nucleic acids, e.g., streptavidin-coated STREP Thermo-Fast PCR plates (Abgene, Surrey, UK). Solid supports can be chemically modified, e.g., aminated (primary or secondary amine) or carboxylated to facilitate attachment of a particular binding pair.

Attachment of the complexes to solid supports can be achieved via either the adapter or the transposase moiety of the complexes. In the latter case, the transposase moiety can carry a tag which allows attachment to solid supports. For, instance a biotin tag can be attached to a recombinant transposase via C-terminal or N-terminal streptavidin-binding peptide (Keefe et al., Protein Expr Purif., Vol. 23, No. 3, p. 440-446, 2001; Duffy et al., Anal Biochem., Vol. 262, No. 2, p. 122-128, 1998) and the complex can be attached to streptavidin-coated beads or plates. However, direct transposase attachment to solid support could sterically impede transposase molecule movement that is important for its enzymatic activity. Furthermore, fusion proteins with peptide tags often have inferior activity as compared to native proteins since such tags may interfere with protein folding. Therefore, the inventor came up with an elegant solution of attachment of transposase-adapter complex through its adapter moiety while using native transposase protein. There are many such tags that can be used by those skilled in the art. Any suitable specific binding pairs can be used in accordance with the invention, wherein at least one member of the pair is immobilized on a solid support, and the skilled artisan is free to choose an appropriate pair based on any number of considerations. A non-exclusive listing of binding pairs includes: avidin or streptavidin and biotin; a nano-tag and streptavidin (see, for example, Lamla and Erdmann, Protein Expr Purif. Vol. 33, No. 1, p. 39-47, 2004), an antibody (or antigen-binding portion thereof) and the antigen/epitope to which it specifically binds, e.g., Myc of FLAG tag; an enzyme-substrate pair, e.g., glutathione transferase and reduced glutathione; poly-histidine and a nickel-based resin; aptamers and their specific target molecules, and Si-tag and silica particles (see, for example, Motomura et al., Protein Expr Purif., Vol 77, No. 2, p. 173-177, 2011).

The specific binding pair member can be covalently linked to the adapter, preferably at its 5' end. Linking can be by way of any suitable technique known for chemically linking substances to nucleic acids. The only limitations are that the specific binding pair member should not interfere with binding of the adapter to the transposase, abolish the activity of the transposase when bound to the solid substrate, or impede amplification of a solid substrate-bound DNA fragments in PCR. To this end, linkers can be provided between a specific binding pair member and the recognition sequence. See, e.g., US20120301925 and co-pending U.S. patent application Ser. No. 13/960,837, the contents of which are incorporated by reference.

One advantage of using solid support-bound transposase complexes derives from the fact that one adapter is bound to the solid support. As such, when the transposase complex cleaves the target DNA, the target DNA becomes captured on the solid support via the adapter. Replacement of the enzyme with the target as a result of the reaction is an elegant way to produce DNA fragments that can easily be purified from reaction components. It is also an elegant way to produce DNA fragments that can be subjected to various reactions without the need for multi-step purification of the DNA fragments, as they can be purified easily by simply washing.

The invention further provides a method of making the above-mentioned adapter-transposase complexes. In general, the method comprises mixing one or more transposases with adapter oligonucleotides that contain recognition sequence(s) for the transposase(s), and allowing the adapters to bind to the transposases to form complexes. The steps of "allowing" comprise providing conditions under which the recited actions occur. Such conditions can be any suitable conditions, including, but not limited to incubation of the transposases and adapter oligonucleotides at from about 0° C. to about room temperature (i.e., about 21° C.-25° C.) for several hours (e.g., 5-14 hours). Higher temperatures and shorter incubation times can be used, but are less preferred due to a possibility of loss of transposase activity. The method can further include producing the transposases, the adapters, or both. Where the method comprises producing the transposases, the method includes expressing the transposase in a host cell prior to lysing the cell. The transposase can be expressed in the cell in which it is naturally found, or can be expressed recombinantly in a host cell that is not its native host cell. Numerous host cells for recombinant production of proteins are known in the art, e.g., bacterial, yeast, plant, insect, or mammalian cells, and the practitioner is free to select any suitable host cell. In exemplary embodiments, *E. coli* cells are used as host cells for recombinant production of transposases.

Uses

The adapters and adapter-transposase complexes described above have numerous uses. Among those uses, the present document exemplifies use of the transposase complexes for preparation of fragmented DNA to be used in further analytical procedures (e.g., high-throughput sequencing) and for gene delivery into plant and animal cells.

A. DNA Fragmentation and Related Uses

The adapters and adapter-transposase complexes described above can be used in fragmenting DNA molecules, such as genomic DNA. The fragmented DNA can be used for a number of purposes including acellular amplification (e.g., PCR) or high-throughput sequencing.

In one aspect, a method of fragmenting DNA and preferably tagging it with adapters is provided. In general, the method comprises combining target DNA to be fragmented with a transposase complex, which can be bound to a solid substrate, and incubating the combination under conditions that are suitable for DNA cleavage by the transposase complex to yield fragmented target DNA bound to the solid substrate. The solid substrate-bound DNA fragments can then be used in any number of analytical reactions. In some embodiments, the components of the reaction mixture that are not bound to the solid substrate are removed, such as by any suitable washing procedure known in the art. In some embodiments, the solid substrate-bound DNA fragments are created and immediately used, without additional purification or preparation. For example, a one-mix DNA fragmentation and amplification mixture can be provided, in which the target DNA is combined with the solid substrate-bound transposase complex under conditions that permit DNA fragmentation to produce solid substrate bound DNA fragments, then the mixture is subjected to conditions that permit acellular amplification of the bound DNA fragments, for example by PCR.

In one embodiment, an in vitro method for generating a DNA fragment library is provided. The method includes incubating a transposon complex comprising an adapter of this invention and a corresponding transposase with a target DNA of interest under conditions for carrying out a transposition reaction. The transposition reaction results in fragmentation of the target DNA, and incorporates the transposon end into the 5' end of the fragmented target DNA.

In one embodiment, the method further comprises the step of amplifying the fragmented target DNA in an amplification reaction using a first and second oligonucleotide primer complementary to the transposon end/in the 5' ends of the fragmented target DNA. The first and second primer optionally comprises 5' tags, which will be further described below. In another embodiment, the method further comprises the step of contacting the fragments of target DNA comprising the transposon end at the 5' ends of the fragmented target DNA with DNA polymerase having 5'-3' exonuclease or strand displacement activity, so that fully double-stranded DNA molecules are produced from the fragments of target DNA. This step is used to fill the gaps generated in the transposition products in the transposition reaction. The length of the gap is characteristic to a certain transposition enzyme. To prepare the transposition products for downstream steps, such as PCR, the method may further comprise the step of de-naturating the fully double-stranded DNA molecules to produce single stranded DNA for use in the amplification reaction.

In case the transposon end sequence comprises an engineered cleavage site, the method can comprise a further step of incubating the fragmented target DNA with an enzyme specific to the cleavage site so that the transposon ends incorporated to the fragmented target DNA are cleaved at the cleavage site. The cleaving enzyme may be an N-glycosylase or a restriction enzyme, such as uracil-N-glycosylase or a methylation specific restriction enzyme, respectively.

In one embodiment, the 5' tags of the first and/or second PCR primer(s) used in the method comprise one or more of the following groups: an amplification tag, a sequencing tag, and/or a detection tag. An amplification tag is a nucleic acid sequence providing specific sequence complementary to an oligonucleotide primer to be used in the subsequent rounds of amplification. For example, the sequence may be used for facilitating amplification of the nucleic acid obtained. A sequencing tag provides a nucleic acid sequence permitting the use of the amplified DNA fragments obtained from an amplification reaction as templates for next-generation sequencing. For example, the sequencing tag may provide annealing sites for sequencing by hybridization on a solid phase. Such sequencing tag may be Life Technologies ION TORRENT sequencing tags, Roche 454A and 454B sequencing tags, Applied Biosystems SOLiD™ sequencing tags, ILLUMINA™ SOLEXA™ sequencing tags, the Pacific Biosciences' SMRT™ sequencing tags, Pollonator Polony sequencing tags, and the Complete Genomics sequencing tags. A detection tag on the other hand allows one to detect and monitor an intermediate product. The detection tag can contain a sequence or a detectable chemical or biochemical moiety for facilitating detection of the nucleic acid obtained from the amplification step. Examples of detection tags include specific nucleic acid sequence, fluorescent and chemiluminescent dyes, a green fluorescent protein, and enzymes that are detectable in the presence of a substrate, e.g., an alkaline phosphatase with NBT plus BCIP, or a peroxidase with a suitable substrate. By using different detection tags, e.g., barcodes, sequences from multiple samples can be sequenced in the same instrument run and identified by the sequence of the detection tag. Examples are Illumina's index sequences in TruSeq DNA Sample Prep Kits, or Molecular barcodes in Life Technologies' SOLiD™ DNA Barcoding Kits.

The adapters according to the invention, when used to fragment DNA, are preferably present in complexes comprised of at least two transposase molecules, where at least two of the transposases of each complex are associated, by way of chemical bonding, to DNA oligonucleotides having the adapters, which are at least partially double stranded. In preferred embodiments, the complexes comprise two transposase molecules, each bound by an adapter. Within the transposase complexes, each transposase can be the same, or have the same recognition sequence for DNA. Alternatively, if the transposases can recognize sequences that differ in several nucleotides, the recognition sequences can differ (see, e.g., US20120301925 and U.S. application Ser. No. 13/960,837). Yet again, the two can differ in identity and/or recognition sequences. Where the two transposases have different recognition sequences, the adapters are suitably designed such that each transposase can bind an adapter. In one embodiment, the transposition system used is based on transposase of *Vibrio* species, such as *Vibrio harveyi*. For the method, one can assemble in vitro stable but catalytically inactive *Vibrio harveyi* transposition complexes in conditions as described in US20120301925.

The adapters can be chemically bound to the transposases of the complex at dsDNA regions of the adapters, which comprise recognition sequences for the transposases. The adapters in a particular complex can, but do not necessarily, comprise a single recognition sequence for a particular transposase. In embodiments, the adapters can comprise two or more recognition sequences for the same transposase. Alternatively, where two different transposases are in a complex, and each has a different recognition sequence, one adapter of the complex will have the recognition sequence for one of the transposases and the other adapter will have the recognition sequence for the other transposase.

When used for fragmenting DNA molecules, selecting a transposase load for a certain range of DNA input is important. For instance, free DNA concentration in human blood or leukocyte count may significantly vary in different patients. Therefore, selecting a transposase-adapter load that would cover a range of specified concentrations would allow automated sample processing for NGS without prior DNA concentration measurement and adjustment. Selecting better suited adapters is not limited to just different DNA inputs. There are many parameters for which the selection/screening could be done, contingent upon a specific need. For instance, selection could be done for ability to process crude, semi-purified or unpurified DNA samples, e.g., from soil, from blood or other bodily liquids or tissues. In another aspect, selection could be done towards ability to process samples which could have been compromised, i.e., partially degraded due to exposure to elements, i.e., ancient and forensic samples, or sample preparation techniques and storage as is the case with FFPE slides (Fortes et al., Bioessays. 2013 August, 35(8):690-5; Sah et al., Genome Med. 2013 Aug. 30; 5(8):77). For instance, with the degraded samples selections towards smaller size of transposase-generated fragments, adapter 8 described in the examples below can be useful.

Paired end sequencing (Illumina) and Ion Torrent (Life Sciences) are the most widely used in the NGS platforms. Samples for either platform could be prepared either by DNA fragmentation using sonication followed by attachment of adapters, or by a transposase method which simultaneously performs DNA fragmentation and attachment of adapters in the same reaction mixture in a few minutes. These methods have pros and cons; sonication achieves more random DNA fragmentation, but it is much more laborious, time-consuming and expensive than transposase methods. Transposase methods are much faster and by far less expensive. However, DNA fragmentation is less random, i.e., it has bias, resulting in more reads and better genome coverage in some regions, and less in others, which often manifests in 1-3% higher duplication rate and correspondingly more sequencing effort to achieve the same overall coverage. This seems a small price to pay, considering many-fold gain with the transposase method in time, labor and equipment expenditure and taking into account that sample preparation constitutes about 50% of the overall sequencing costs. Nevertheless, reducing the duplication rate is highly desirable.

Figure 11:
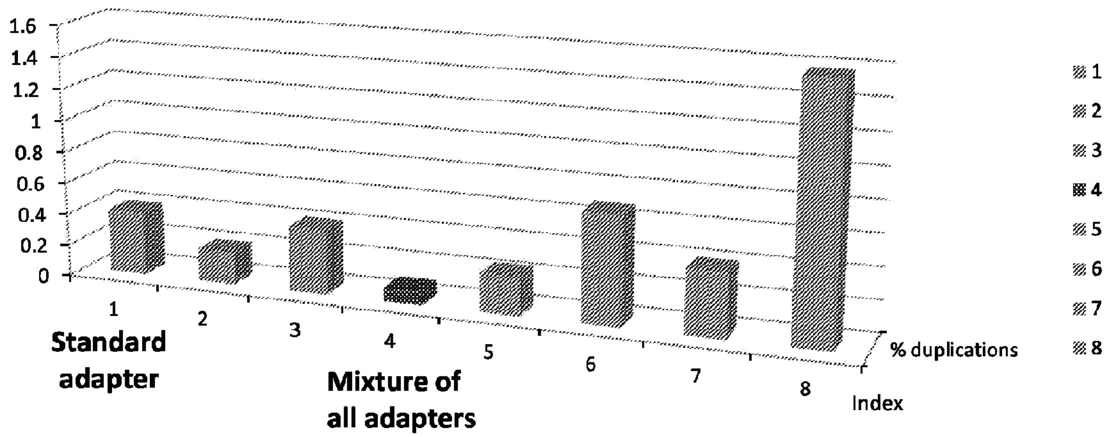
FIG. 11 is a diagram showing duplication rates conferred to Vibhar transposase by different adapters and by their mixture.
Figure 13:
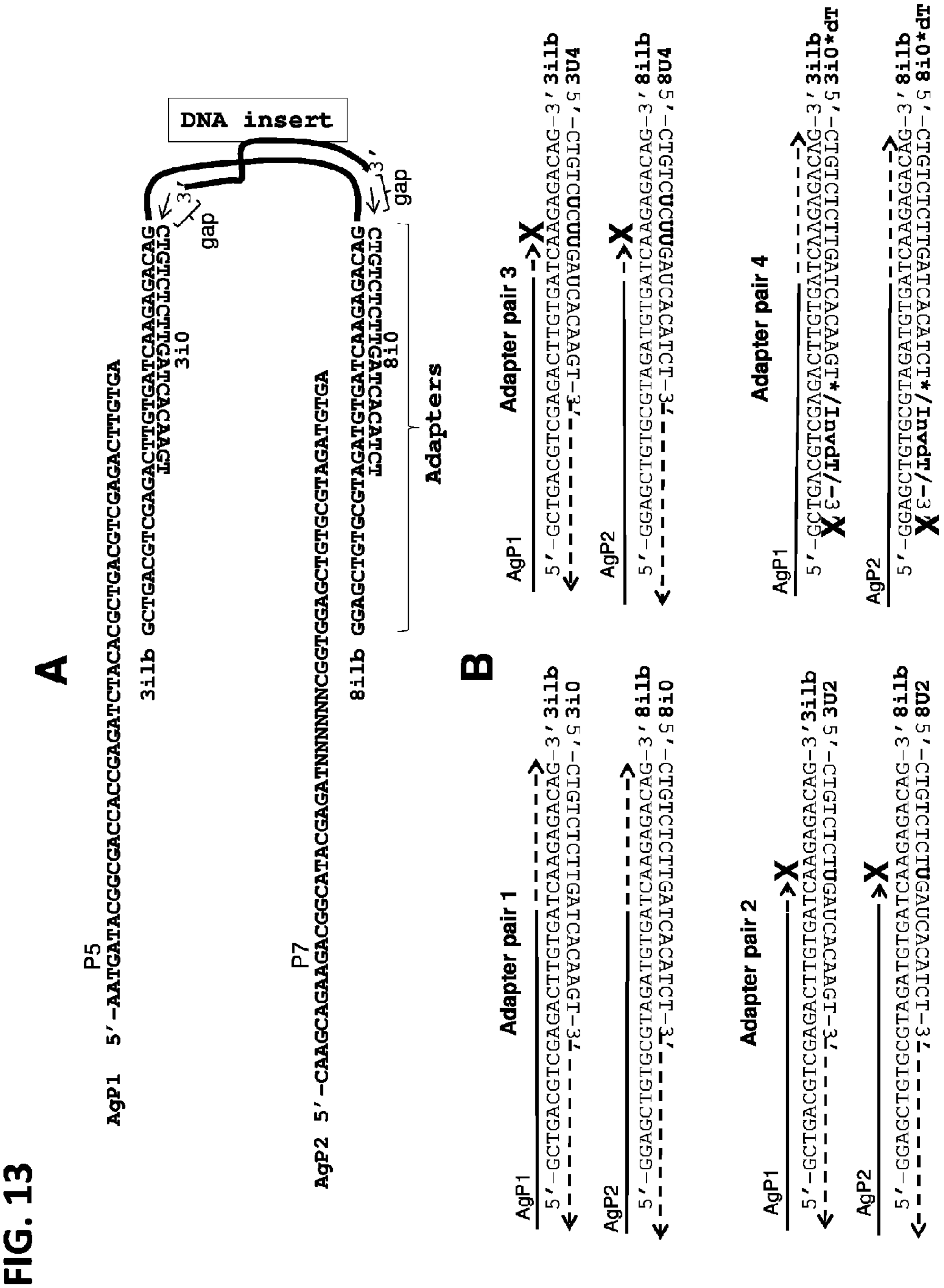
FIGS. 13A and 13B illustrate some prior art oligonucleotides and some exemplary modified oligonucleotides of this invention, including AgP1, AgP2, 3ilb, 8ilb, 3i0, 8i0, 3U2, 8U2, 3U4, 8U4, 3i0*dT, and 8i0*dT (SEQ ID NOs: 79-90, respectively): (A) Example of typical product of transposase reaction comprising a DNA insert, i.e., DNA fragment tagged with 3ilb/3i0 and 8ilb/8i0 adapters, as well as AgP1 and AgP2 primers for amplification of the DNA fragment in PCR. Gaps on both sides of the DNA insert are shown; arrows in the gaps indicate direction of DNA polymerase repair of the gaps. (B) Prior art adapters and modified adapters. Solid parts of the arrows indicate hybridized oligonucleotides; dashed parts indicate extended parts, i.e., copied by DNA polymerase. Bold X represents impeded or blocked DNA polymerase extension. dU: deoxyuridine; InvdT: inverted thymidine; and asterisk: phosphorothioate bond.

As disclosed herein, different adapters confer different duplication rates. As represented in FIG. 11, adapters 9 and 5 conferred significantly less duplication rate than a standard adapter 1 with native CG pair in the first position; adapters 6 and 8 conferred a higher duplication rate and adapters 7 and 10 conferred about the same duplication rate as the adapter 1. Surprisingly, a mixture of adapters conferred a much lower duplication rate than any of the adapters (FIG. 11). A possible explanation is that transposase loaded with different adapters is biased to different places on target DNA. These places that are more eagerly recognized by a transposase are called "hot spots" (Berg et al., Genetics. 1983, 105(4):813-28). These hot spots are largely responsible for the duplications as the hot spot areas are sequenced more frequently. However, different adapters confer different hot spots. Since the hot spots differ with different adapters, applying a transposase mixture loaded with different adapters randomizes hot spots and reduces the duplication rate. Furthermore, selecting for the mixture of adapters which individually confer low duplication rate could reduce the duplication rate even further. Transposase loads loaded with different adapters also differ in other properties, e.g., different AT dropout rates (FIG. 12).

B. Uses Related to Low-Cell-Number Sequencing and Microarray

As mentioned above, the adapters disclosed herein can be used for preparing samples used in microarray. Microarray technology is used for large scale genotyping, gene expression profiling, comparative genomic hybridization, DNA sequencing, gene discovery, pathways reconstruction and disease diagnostic (Dufva M. Methods Mol Biol. 2009; 529:1-22; Gibriel A A. Brief Funct Genomics. 2012 July; 11(4):311-8). Despite undeniable advantages in this field, applications in clinical settings are still limited by the use of traditional microarray technology at a few highly specialized laboratories (Guarnaccia et al., Genomics. 2014 pii: S0888-7543(14)). The main reason is complexity of microarray technology, which is suitable to research laboratories but not to diagnostic ones, ibid.

DNA sample preparation for microarrays generally comprises (i) DNA fragmentation, (ii) DNA amplification (optional and contingent upon amount of the starting material), and (iii) DNA labeling with fluorophores to allow detection of hybridized samples to DNA probes immobilized on solid support. Reference and subject samples can be processed separately and labeled with different fluorophores to allow comparison between the samples (Agilent Oligonucleotide Array-Based CGH for Genomic DNA analysis. Protocol version 7.2 July 2012). Generally, DNA samples for microarray can be fragmented using restriction endonuclease digestion, or thermal DNA fragmentation. Among these conventional approaches, endonuclease digestion provides better performance, but it takes about 2 h 20 min to perform. In contrast, DNA fragmentation at 95° C. is achieved within only 4 min. However, it is often not as robust as the restriction nuclease digestion and is unsuitable for SNP analysis applications, e.g., SurePrint G3 CGH+SNP.

As disclosed herein, this invention offers significant improvements at all three stages. More specifically, at the first stage transposase simultaneously fragments DNA to the specified size (200-500 bp, i.e., ideal for Agilent arrays) and provides defined 19 bp tags (FIG. 21A). At the amplification stage, unlike in current Agilent protocol and in other WGA methods, defined 19 bp primer, rather than far less reliable random primer is used (FIG. 21B). Finally, at the labeling step much faster labeling is achieved as the same defined primer rather than random primer is used (FIG. 21C).

As shown in Example 6 below, sample DNA can be fragmented using transposase-oligonucleotide complex and the DNA fragments can then be tagged at both ends with oligonucleotide tags. The oligonucleotide tags can be used to amplify the DNA fragments with primers complementary to the tag, or can be used as a landing site for a primer complementary to the tag and the primer is extended in polymerase reaction using dNTP mixture comprising at least one dNTP labeled with a fluorophore.

Figure 22:
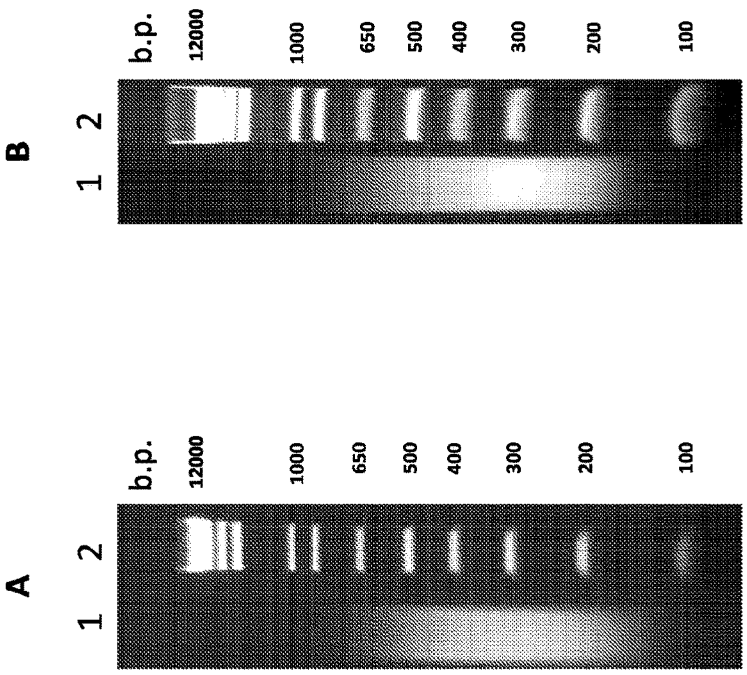
FIGS. 22A and 22B are photographs showing human DNA fragmented and tagged in transposase reaction and amplified in PCR with primers complementary to the tags for microarrays. A: 16 pg DNA input and B: 200 ng DNA input.

Contingent on the DNA input the reaction can take as short as only 5-20 min. More importantly, oligonucleotide tags are attached to each end of the produced DNA fragments (FIG. 21A). As shown in Example 6, no DNA damage was observed as reaction was performed at about neutral pH, at 45° C. and for a short time. With the transposase method DNA fragments of ideal size were created for Agilent microarrays (Agilent Oligonucleotide Array-Based CGH for Genomic DNA analysis. Protocol version 7.2 July 2012). As shown in FIG. 22, ideal fragment length between 200 and 500 b.p. were routinely produced at DNA inputs ranging from 16 pg to 200 ng.

The fragmented DNA can be subject to amplification, which is optional. That is, it is required if amount of gDNA is less than 0.5 ug for 1-, 2-, or 4-pack Agilent microarrays or 0.2 ug 8-pack microarrays. In Example 6 below, DNA amplification was carried out with PCR using primer that is complementary to the tag attached to the ends of DNA fragments in the transposase reaction (FIG. 21B). By way of example and not a limitation, if fragments are tagged with phosphorothioate containing oligonucleotide 5'-A*G*A*T*G*T*G*A*T*CAAGAGACA*G-3' (SEQ ID NO.: 95) in duplex with its phosphodiester complement, then fragments are amplified with primer 7 5'-AGATGTGATCAAGAGACAG-3' (SEQ ID NO.: 93, FIG. 21B). Number of PCR cycles depends on the amount of starting DNA.

Many thermostable DNA polymerases and polymerase compositions can be used for this purpose and examples include Taq, Taq2000, Pfu, PfuUltra, PicoMaxx and Herculase. Alternatively, a highly processive polymerase, such as Bst or Phi29 can be used for amplification. Using defined primer of this invention, such as primer 7, instead of a random primer of prior art, one can achieve much faster and better quality amplification. Better quality (less bias) is achieved with defined primer, as random primer is the major reason for bias generated in whole genome amplification (WGA) methods. Furthermore, priming from random primer is inefficient because relative concentration of 6-mer primer to landing sites is low as there are 4096 hexamer combinations. Another reason for its inefficiency is that reaction temperature is ~30° C. above the random primer Tm (Agilent Oligonucleotide Array-Based CGH for Genomic DNA analysis. Protocol version 7.2 July 2012). Seemingly the latter problem could be resolved by lowering the reaction temperature, but then the temperature becomes suboptimal for the enzymatic reaction. Therefore, using defined primer of this invention allows not only reduction of the amplification bias, but also faster processing of the samples as the reaction conditions are optimal.

The third step in microarray sample preparation is DNA labeling. The rationale for improving the DNA labeling step is the same as for improving the DNA amplification step, which is that a defined primer is used in this invention as opposed to the random primer in prior art. Generally, labeling is achieved with cyanine 3-dUTP for reference sample and cyanine 5-dUTP for test sample (Agilent Oligonucleotide Array-Based CGH for Genomic DNA analysis. Protocol version 7.2 July 2012). Exo (−) Klenow fragment of *E. coli* DNA polymerase is used in combination with a random primer. Labeling reaction requires about 2 hours incubation largely because of inefficiency of random primer. Utilizing defined primer as disclosed herein would cut the reaction time to several minutes since the rate of base pair synthesis by Polymerase I averages between 10 and 20 nucleotides/second. With the defined primer firmly annealed to the 3' end of a 200-500 nucleotide DNA fragment (FIG. 21C) about 10 minutes would be sufficient for the labeling reaction. Since Polymerase I rate is relatively slow and off-rate is high, faster enzymes with better processivity can be selected by those skilled in the art to further reduce the time (Anderson et al., Incorporation of reporter-labeled nucleotides by DNA polymerases. 2005, BioTechniques 38:257-264). Labeling in PCR reaction is also an option, for example using Taq, Vent exo- or Pfu exo-polymerases.

In short, the adapters and methods disclosed herein allow one to achieve significant performance improvement of microarray sample preparation Improved quality at DNA fragmentation step is achieved especially for low DNA input as typically preferred conventional method, using restriction endonucleases, is impractical at the low input. Thermal DNA fragmentation, although more suitable for low input than restriction endonucleases, damages DNA and is not suitable for SNP applications. In addition, significant gain in quality (less library bias) is achieved at the amplification stage because random primer is not used Improved efficiency and reduction in time are also achieved at all three steps. As mentioned above, at the DNA fragmentation step, conventional restriction endonuclease digestion generally takes about 2 hours while transposase approach takes about 5-20 min (contingent upon DNA input); at the DNA amplification step with a 50 ng DNA input, conventional WGA/PCR takes about 3 hours while the transposase-PCR approach takes about one hour; at the labeling step, convention current-random primer approach takes 2 hours while the transposase-defined primer approach takes about 10 min. Overall time saving can be up to about 4-5 hours or more.

Adapters of this invention allow one to reduce complexity of DNA sample preparation for microarrays combined with much faster processing of the samples and improved performance Using this approach, one can improve the efficiency, reduce the time for sample preparation by several hours, and reduce bias as compared to standard protocols (e.g., Agilent Oligonucleotide Array-Based CGH for Genomic DNA analysis sample preparation protocol). As mentioned above, these are also important for single-cell or low-cell-number applications in pre-implantation diagnosis, copy number variation, and SNP analyses.

C. Nucleic Acid Delivery

Transposases are well established as tools for gene delivery into eukaryotic cells, e.g., mammalian (Suganuma et al., Biol Reprod. 2005 December; 73(6):1157-63), insect (Rowan et al., Insect Biochem Mol Biol. 2004 July; 34(7): 695-705.) and plant (Wu et al., Plant J. 2011 ct; 68(1):186-200; Wu et al., Plant Mol Biol. 2011 September; 77(1-2): 117-27). See also U.S. Pat. Nos. 8,283,518 and 8,227,432. The adapters and adapter-transposase complexes of this invention can be included in a nucleic acid delivery vehicle to deliver nucleic acid (e.g., a gene) into plant and animal cells for treatment of diseases, production of useful proteins, and generation of genetically modified plants and animals.

A typical transposase gene delivery system does not comprise a transposome, but instead comprises two plasmids, one donor plasmid encoding a gene of interest that is operably linked to a promoter, and another encoding a transposase. See, e.g., Meir and Wu, MChang Gung Med J. 2011 November-December; 34(6):565-79; Yusa et al., Proc. Natl. Acad. Sci. USA, Vol. 108, No. 4, 1531-1536, 2011; Germon et W., Genetic, Vol. 173, No. 3: 265-276, 2009; De Silva et al., Human Gene Therapy, 21: 1603-1613, 2010). In the donor plasmid, the gene of interest and the promoter are flanked by transposase recognition sequences that are inverted with respect to each other. In the helper plasmid, a sequence encoding a transposase is operably linked to a promoter. Upon co-transfection into the cytoplasm of eukaryotic host cells, some of the helper plasmid reach the nucleus where the transposase gene can be transcribed into mRNA, which can then be transported into the cytoplasm and translated into transposase protein. The transposase binds to its recognition sequences in the donor plasmid DNA, excises extra plasmid DNA sequences, and forms a complex with a gene of interest flanked by the recognition sequences, i.e., transposome. Next, the complex is transported into the nucleus where it can act on genomic DNA and become integrated into it.

An alternative transposase-based gene delivery system is described in U.S. application 61/779,623 filed on Mar. 13, 2013, the content of which is incorporated herein in its entirety. This alternative greatly improves gene delivery into plant and animal cells. At its core, the alternative system includes complexes comprising a transposome (i.e., at least one transposase bound to a nucleic acid having two binding sites for the transposase(s)) reversibly or releasably linked to a targeting element that targets the transposome to a pre-selected DNA-containing organelle of a target (e.g., nucleus or mitochondria) or host cell of interest. In use, the complex is delivered to cells of interest, taken up by the cells, and transported within the cells to the pre-selected DNA-containing organelle. Once inside the pre-selected DNA-containing organelle, the transposome and targeting elements are typically separated, and the transposome inserts the nucleic acid into the DNA of the host cell.

The adapters and adapter-transposase complexes of this invention can be used in both the conventional system and the alternative system. These systems and related gene delivery methods can be used to insert a nucleic acid into the genomic DNA or DNA of a pre-selected DNA-containing organelle in the manner described in, e.g., U.S. application 61/779,623 filed on Mar. 13, 2013.

In view of these uses, the adapters and adapter-transposase complexes of this invention can be used in methods of treating a subject suffering from, or at a high likelihood of developing a disease or disorder. The method may be a therapeutic method of treating a subject suffering from a disease or disorder. Alternatively, the method may be a prophylactic method of treating a subject suspected of having a high likelihood of developing a disease or disorder in the future. In yet other embodiments, the method is method of preventing a disease or disorder in a subject, such as through a DNA vaccine. By delivering nucleic acids encoding desired genes, and under certain control elements, into the cells of a subject, certain proteins or nucleic acids can be expressed in the cells, or expression of certain proteins or nucleic acids can be reduced or abolished, thus effecting treatment of the subject.

The ability to deliver a nucleic acid having a sequence of interest can also be used for creating transgenic non-human animals and plants. Such transgenic non-human animals and plants can have one or more desired phenotypic characteristics, including immunity to certain viruses or bacteria, resistance to certain drugs or toxins, drought resistance, increased protein-to-fat ratio, increased production of a nutrient, expression of a pharmaceutically active substance, and reduced production of a harmful substance.

Kits

Another aspect of the invention provides kits. In general, kits according to the present invention comprise at least one of the adapters of the invention described above and additional reagents that are useful in, e.g., for fragmenting DNA, for fragmenting and sequencing, or for nucleic acid delivery.

In one embodiment of the kit of the invention, one or more oligonucleotide adapters are provided in one or more containers. The adapter can be provided as a liquid solution (e.g., an aqueous or alcohol solution) in one or more containers. Alternatively, the adapter can be provided as a dried composition in one or more containers. In embodiments, two or more different adapters can be provided in a single container or in two or more containers. Where two or more containers are provided, each container can comprise a single adapter, or one, some, or all of the containers can comprise a mixture of one, some, or all of the adapters.

The kit can further comprise one or more purified transposases. The transposase can be provided as a liquid solution or as a dried composition in one or more containers. In some embodiments, two or more different purified transposases are provided in a single container or in two or more containers. Where two or more containers are provided, each container can comprise a single transposase, or one, some, or all of the containers can comprise a mixture of one, some, or all of the transposases.

Preferably, at least one of the adapters comprises a recognition sequence for at least one of the transposases. More preferably, at least one adapter that has a recognition sequence for at least one transposase of the kit is provided. In this embodiment, it is to be noted that, because a particular transposase might recognize multiple related sequences, there does not need to be a one-to-one matching of transposases and adapters in the kit. As with other embodiments, in this embodiment of the kit, the transposases and adapters can be provided singly in different containers or any mixture of transposases and adapters can be provided in any number of containers.

In yet another embodiment, the kit can comprise one or more transposase complexes. As with other embodiments, the complexes can be provided in a liquid composition or as a dried material. Furthermore, any number of different complexes can be provided in a kit. As above, the complexes can be provided singly in or on different containers or any mixture of complexes can be provided in or on any number of containers.

In an exemplary embodiment, the kit comprises one or more transposase complexes bound to a solid support such as beads or nanoparticles. In this embodiment, the solid support is considered to be a container for the complexes. The complexes are bound to the solid support by way of linkers, such as by a specific binding pair. In one exemplary embodiment, the complexes are provided bound to the surface of the wells of a PCR plate. In this embodiment, each well can comprise a single type of complex, or it can comprise two or more different complexes. In another exemplary embodiment of the kit, the complexes are provided bound to the surface of a nylon membrane, such as a nylon strip. In this embodiment, the complexes can be distributed about the membrane in any desired order and geometric shape and in any combination. For example, the membrane can have a single complex disposed on the membrane in a series of lines or dots. Alternatively, a series of lines or dots of different complexes can be provided (e.g., complex 1 is disposed on dot 1, complex 2 is disposed on dot 2, etc.). Yet again, mixtures of two or more complexes can be disposed on dots, lines, etc.

As noted above, in certain embodiments, it is preferable to provide two or more different transposase complexes having different recognition sequences in order to reduce GC vs. AT bias and thus to provide superior control of fragmentation of genomic DNA. In the context of kits comprising mixtures of transposase complexes, prior to creating the kit, one or more mixture can be optimized to minimize the bias for a particular target DNA by varying the ratios of complexes in the mixture. One skilled in the art can easily recognize how to create different mixtures of transposase-adapter complexes, how to immobilize them on solid supports, and how to apply them for target DNA fragmentation. The skilled artisan also knows how to amplify and sequence the fragments, analyze the sequencing data, select the mixture combination (ratio) with the least bias, and produce a kit based on that combination. It should be noted that different ratios can be recommended for different DNA targets and different kits can be manufactured for different types of targets. For instance, one skilled in the art can recognize that more transposase-adapter complexes with AT bias should be used for AT-rich targets.

In certain embodiments of kits where two different transposases are present, the kits preferably comprise four different oligonucleotide adapters. Two of the adapters comprise a recognition sequence(s) for one transposase, but only one of which comprises a specific binding pair member. The other two adapters comprise a recognition sequence(s) for the other transposase, but only one of which comprises a specific binding pair member. Through use of a combination of the adapters, transposase complexes can be formed and bound to a solid substrate via the specific binding pair members.

The kits of the invention can comprise any number of additional reagents or substances that are useful for practicing a method of the invention. Such substances include, but are not limited to: reagents (including buffers) for lysis of host cells, divalent cation chelating agents or other agents that inhibit nucleases, control DNA for use in ensuring that the transposase complexes and other components of reactions are functioning properly, DNA fragmenting reagents (including buffers), PCR reaction reagents (including buffers), and wash solutions. The kits of the invention can be provided at any temperature. For example, for storage of kits containing transposases, adapters, or complexes in a liquid, it is preferred that they are provided and maintained below 0° C., preferably at or below −20° C., or otherwise in a frozen state.

Components of the kits can be provided in containers or on solid substrates. The containers and solid substrates are provided in packaged combination in a suitable package, such as a box made of cardboard, plastic, metal, or a combination thereof. Suitable packaging materials for biotechnology reagents are known and widely used in the art, and thus need not be specified herein.

The term "nucleic acid" as used herein refers to a DNA molecule (e.g., a genomic DNA or cDNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. A nucleic acid adapter of this invention can include canonical and/or non-canonical nucleic acid bases. The term "canonical" is used to refer to the four common nucleic acid bases adenine, cytosine, guanine and thymine that are commonly found in DNA or to the respective deoxyribonucleosides, deoxyribonucleotides or 2'-deoxyribonucleoside-5'-triphosphates that contain a canonical base. The term "non-canonical" is used to refer to nucleic acid bases in DNA other than the four canonical bases, or to the respective deoxyribonucleosides, deoxyribonucleotides, or 2'-deoxyribonucleoside-5'-triphosphates that contain a non-canonical base. For example, although uracil is a common nucleic acid base in RNA, uracil is a non-canonical base in DNA. "Non-canonical bases" are found in nucleic acids as a result of incorporation of non-canonical nucleotides (e.g., by synthesis using an oligonucleotide synthesizer or by synthesis using a DNA polymerase) or as a result of modification of existing bases (canonical or non-canonical).

The term "oligonucleotide" refers to a short polymer of nucleotides and/or nucleotide analogs. An oligonucleotide is preferably at least 4 nucleotides, e.g., at least about 10-15, 10-20, 15-25, or 15 to 200 nucleotides. The exact size will depend on many factors, which in turn depend on the ultimate function or use of the oligonucleotide. The oligonucleotide may be generated in any manner, including chemical synthesis, DNA replication, reverse transcription, PCR, ligation, or a combination thereof.

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in "enrichment," i.e., an increase in the amount of a desirable protein and/or nucleic acid sequence in the sample.

As used herein, a "tag" refers to a non-target nucleic acid component, generally DNA, that provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA"). A "tag portion" or a "tag domain" means a portion or domain of a tag that exhibits a sequence for a desired intended purpose or application.

As used herein, a "sequencing tag" or a "sequencing tag domain" means a tag or tag domain that exhibits a sequence for the purposes of facilitating sequencing of the ssDNA fragment to which the tag is joined using the method to synthesize tagged circular ssDNA fragments (e.g., to provide a priming site for sequencing by synthesis, or to provide annealing sites for sequencing by ligation, or to provide annealing sites for sequencing by hybridization). For example, in some embodiments, the sequencing tag domain provides a site for priming DNA synthesis of said ssDNA fragment or the complement of said ssDNA fragment.

As used herein, an "amplification tag" or "amplification tag domain" means a tag or a tag domain that exhibits a sequence for the purpose of facilitating amplification of a nucleic acid to which said tag is appended. For example, in some embodiments, the amplification tag or domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction).

As used herein, a "detection tag" or a "detection tag domain" means a tag or tag domain that exhibits a sequence or a detectable chemical or biochemical moiety for the purpose of facilitating detection of the tagged ssDNA fragment (e.g., wherein the sequence or chemical moiety comprises or is joined to a detectable molecule; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate); a detectable protein, e.g., a green fluorescent protein; and an affinity-binding molecule that is bound to a detectable moiety or that can form an affinity binding pair or a specific binding pair with another detectable affinity-binding molecule; or any of the many other detectable molecules or systems known in the art).

As used herein, an "address tag" or an "address tag domain" means a tag or a tag domain that exhibits a sequence that permits identification of a specific sample (e.g., wherein the transferred strand has a different address tag domain that exhibits a different sequence for each sample).

As used herein, a "DNA fragment library" or a "library of DNA fragments" means a collection or population of tagged DNA fragments generated from target DNA, wherein the combination of the tagged DNA fragments in the collection or population exhibits sequences that are qualitatively and/or quantitatively representative of the sequence of the target DNA from which the tagged DNA fragments were generated, and wherein the tagged DNA fragments that are in the collection or population have not been selected for or selected against by intentionally using a method that either includes or excludes tagged DNA fragments based on the nucleotide or sequence composition of the target DNA. For a variety of reasons, it is possible that a DNA fragment library may not contain a tagged DNA fragment representing every sequence which is exhibited by the target DNA.

As used herein, "target DNA" refers to any dsDNA of interest that is subjected to transposition, e.g., for generating a library of tagged DNA fragments. Target DNA can be derived from any in vivo or in vitro source, including from one or multiple cells, tissues, organs, or organisms, whether living or dead, or from any biological or environmental source (e.g., water, air, soil). For example, in some embodiments, the target DNA comprises or consists of eukaryotic and/or prokaryotic dsDNA that originates or that is derived from humans, animals, plants, fungi, (e.g., molds or yeasts), bacteria, viruses, viroids, mycoplasma, or other microorganisms. In some embodiments, the target DNA comprises or consists of genomic DNA, subgenomic DNA, chromosomal DNA (e.g., from an isolated chromosome or a portion of a chromosome, e.g., from one or more genes or loci from a chromosome), mitochondrial DNA, chloroplast DNA, plasmid or other episomal-derived DNA (or recombinant DNA contained therein), or double-stranded cDNA made by reverse transcription of RNA using an RNA-dependent DNA polymerase or reverse transcriptase to generate first-strand cDNA and then extending a primer annealed to the first-strand cDNA to generate dsDNA. In some embodiments, the target DNA comprises multiple dsDNA molecules in or prepared from nucleic acid molecules (e.g., multiple dsDNA molecules in or prepared from genomic DNA or cDNA prepared from RNA in or from a biological (e.g., cell, tissue, organ, organism) or environmental (e.g., water, air, soil, saliva, sputum, urine, feces) source. In some embodiments, the target DNA is from an in vitro source. For example, in some embodiments, the target DNA comprises or consists of dsDNA that is prepared in vitro from single-stranded DNA or from single-stranded or double-stranded RNA (e.g., using methods that are well-known in the art, such as primer extension using a suitable DNA-dependent and/or RNA-dependent DNA polymerase (reverse transcriptase). In some embodiments, the target DNA comprises or consists of dsDNA that is prepared from all or a portion of one or more double-stranded or single-stranded DNA or RNA molecules using any methods known in the art, including methods for: DNA or RNA amplification (e.g., PCR or reverse-transcriptase-PCR (RT-PCR), transcription-mediated amplification methods, with amplification of all or a portion of one or more nucleic acid molecules); molecular cloning of all or a portion of one or more nucleic acid molecules in a plasmid, fosmid, BAC or other vector that subsequently is replicated in a suitable host cell; or capture of one or more nucleic acid molecules by hybridization, such as by hybridization to DNA probes on an array or microarray (e.g., by "sequence capture"; e.g., using kits and/or arrays from ROCHE NIMBLEGEN, AGILENT, or FEBIT).

A "primer" is an oligonucleotide ("oligo"), generally with a free 3'-OH group that can be extended by a nucleic acid polymerase. For a template-dependent polymerase, generally at least the 3'-portion of the primer oligo is complementary to a portion of a template nucleic acid, to which the oligo "binds" (or "complexes," "anneals," or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Template-dependent DNA polymerases (including reverse transcriptases) generally require complexing of an oligonucleotide primer to a single-stranded template to initiate DNA synthesis ("priming"), but RNA polymerases generally do not require a primer for synthesis of RNA that is complementary to a DNA template (transcription).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

EXAMPLES

Example 1 Designing Plurality of Adapters for Specific Transposases

This example describes designing and generating transposase adapters based on native or known transposase recognition sequences.

Native or known transposase recognition (adapter) sequences were either obtained from publications, e.g., "mosaic" for "hyperactive" Tn5 transposase (Zhou et al., J Mol Biol. 1998; 276(5):913-25), or using bioinformatics methods as for Vibhar transposase (US Application 20120301925), FIG. 1. Briefly, microbial nucleotide blast was performed against known transposase recognition sequences on NCBI Microbial Nucleotide BLAST web site (blast.ncbi.nlm.nih.gov/Blast.cgi?PAGE_TYPE=Blast Search&PROG_DEF=blastn&BLAST_PROG_DEF=megaBlast&SHOW_DEFAULTS=on&BLAST_SPEC=MicrobialGenomes) using blastn algorithm (Megablast optimized for highly similar sequences, representative genomes only, max target sequences 250, expect threshold 10, gap costs linear, filter low complexity regions). Validity of discovered transposase recognition sequences (adapters) was confirmed by finding transposase genes in vicinity of the sequences.

Next, plurality of adapters was designed based on a native transposase adapter, or on a modified adapter which was already developed for a particular transposase, e.g., "mosaic" for Tn5 transposase or adapters 3il and 8il for Vibhar transposase (United States Patent Application 20120301925). The nucleotide position which is the closest to the cut at the transposition event (facing inside the transposon in nature) and is conserved among the same family of transposases was chosen for modification. Position 1 as represented in FIG. 1 was preferred while positions 2 and/or 3 are less preferred as position 1 is most important for modulating transposase properties as it is adjacent to the cut and is positioned in the catalytic site, for example as represented for Tn5 transposase in FIG. 2.

As represented in FIG. 3 for Vibhar transposase and in FIG. 4 for "hyperactive" Tn5 transposase, this position can be modified by substituting one nucleotide on either strand or on both strands for native or modified nucleotide, or by adding at least one native or modified nucleotide to one or both strands, or removing at least one nucleotide from one strand, or by combination of the above. Examples of the modified nucleotides have been described above.

Example 2 Selecting Adapters for High, Medium and Low Input NGS

In this example, a number of transposase adapters generated in Example 1 above were examined for their activities in fragmenting genomic DNA for NGS at different DNA input levels.

For the simplicity of description, adapters used in this example were numbered as indicated in FIG. 5B, where only the bases at position 1 on both strands and the bases further 5' on the top strand and further 3' on the bottom strand are shown. Vibhar transposase was loaded with 3il and 8il adapters that were provided with additional nucleotide sequences that are necessary for sequencing on Illumina instruments as described previously (US Patent Application 20120301925) and applied for fragmentation of *E. coli* DNA (ATCC Cat#8739D-5).

For high DNA input, fragmentation was performed in 20 μl reaction mixtures containing 200 ng of *E. coli* DNA *Escherichia coli* (Migula) Castellani and Chalmers (ATCC, Manassas, Va.), 10 mM Bicine-NH4 pH 7.5, 5 mM MnCl2, 12 mM potassium glutamate and 50 ug Vibhar transposase. The reaction mixture was incubated at 46 or 56° C. for 15 min and stopped by addition of EDTA up to 20 mM. Fragmented and tagged DNA was purified from unincorporated adapters using Agencourt AMPure XP system, aka SPRI beads (Beckmam Coulter, Indianapolis, Ind.) according to the manufacturer's instruction. DNA from one PCR reaction was eluted from beads into 20 μl of water.

Next, fragmented and tagged DNA was amplified in PCR. 20 μl PCR reaction mixtures contained 2 μl of a SPRI beads-purified template, 4 μl of 5× Herculase II Rxn buffer, 0.5 μl Herculase® II (Agilent Technologies, Santa Clara, Calif.), 1 mM dNTPs, 5% DMSO, forward primer AgP1 5'-AATGATACGGCGACCACCGAGATCTACACGCTGAC GTCGAGACTTG TGA-3' (SEQ ID No.: 77) and reverse primer AgP2 5'-CAAGCAGAAGACGGCATACGAGA TCGGTGGAG CTGTGCGTAGATGTGA-3' (SEQ ID No.: 78) both at 1 uM concentrations. Amplification was started with incubation at 72° C. for 2 min in order to fill the adapter gaps and to displace bottom adapter strand, followed by DNA melting step at 95° C. for 3 min, and 11 cycles of: i) denaturation at 95° C. for 40 sec, ii) annealing at 61° C. for 1.5 min and, iii) elongation at 72° C. for 3 min. The cycles were followed by incubation at 72° C. for 10 min in order to ensure that the PCR fragments are completely double-stranded. PCR fragments were separated in 2% agarose gels and stained with ethidium bromide. The gels were photographed at 302 nM wavelength using MultiImage™ multiimage light cabinet (Alpha Innotech, San Leandro, Calif.).

Figure 6:
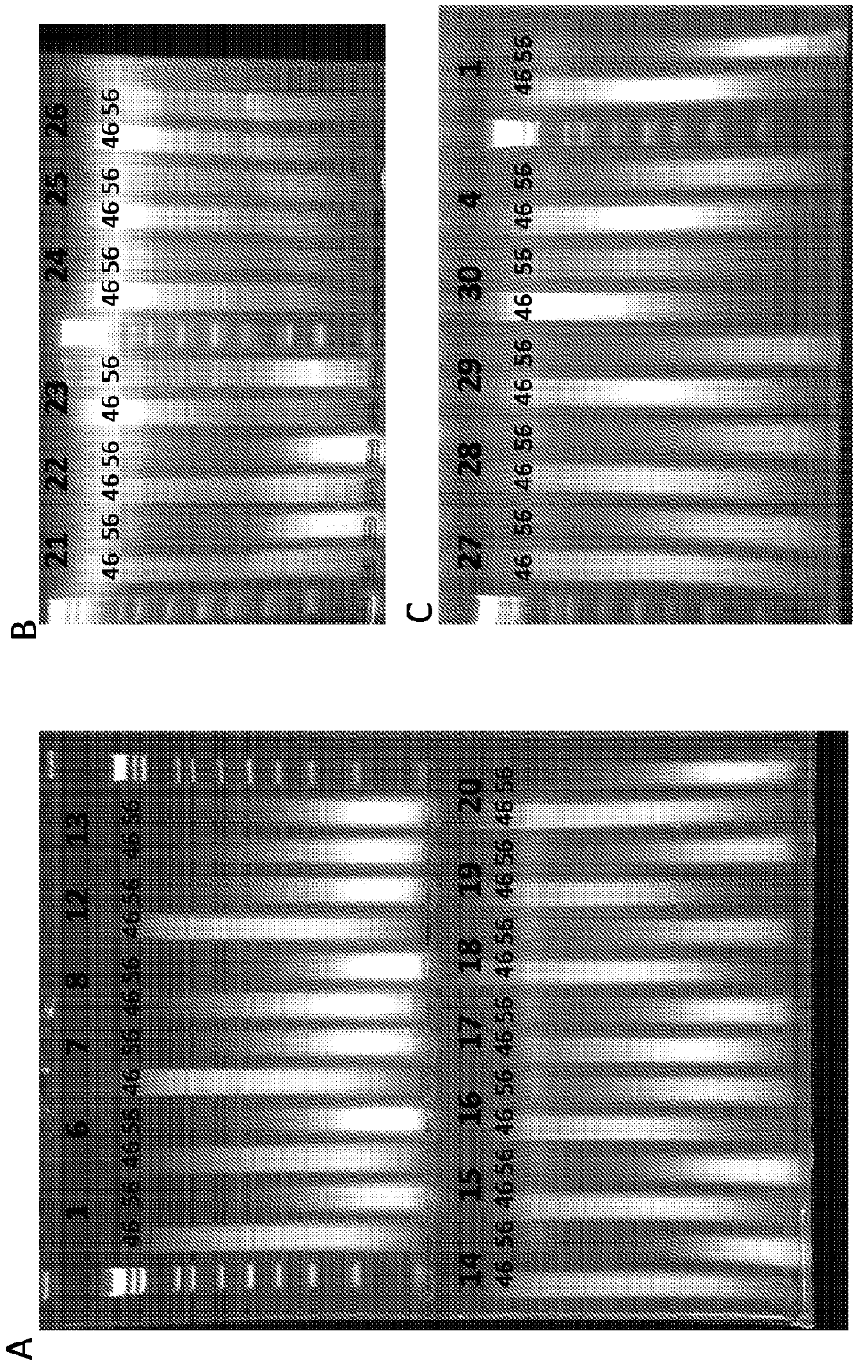
FIGS. 6A, 6B, and 6C are diagrams showing assessment of activity of plurality of adapters in sample preparation for NGS at high DNA input. NGS samples generated using Vibhar transposase loaded with different adapters were separated in 2% agarose gels and stained with ethidium bromide.
Figure 7:
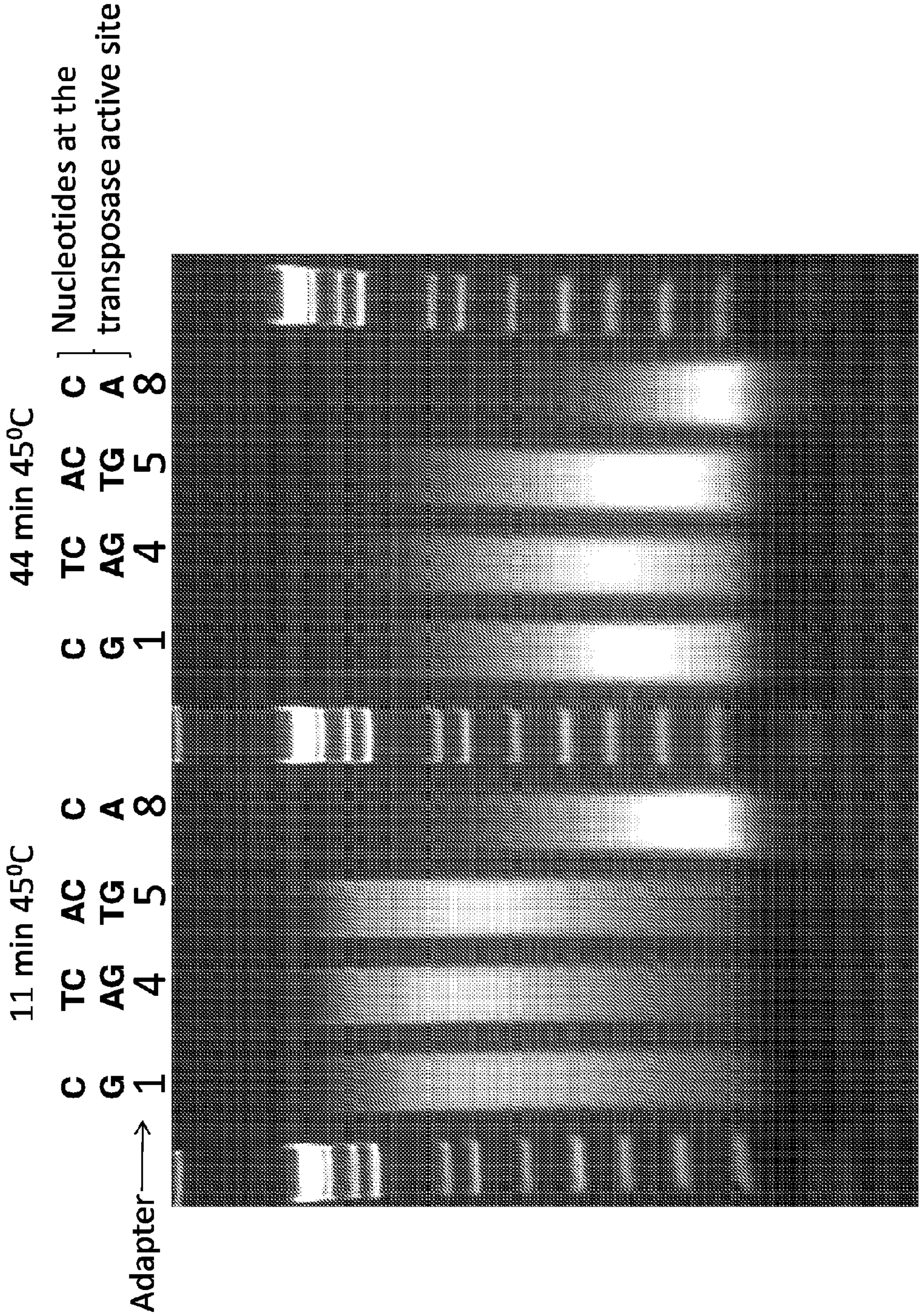
FIG. 7 is a diagram showing confirmation of higher activity of adapter 8 at high DNA input as compared to other derivative adapters and to parental adapter 1. NGS samples generated using Vibhar transposase loaded with different adapters were separated in 2% agarose gels and stained with ethidium bromide.

As follows from the gels represented in FIG. 6, at high DNA input most of the adapters exhibited suitable activity in DNA fragmentation and tagging for NGS on Illumina Instruments, indicating that most of the changes at conserved position 1 were well tolerated. Therefore, plurality of adapters with suitable activity was created despite changing conservative CG pair in position 1 of Vibhar native adapter. Moreover, adapters conferred different properties to the transposase, e.g., adapter 8 appeared to confer higher activity, which manifested in smaller fragment size, and which was confirmed in additional experiments (FIG. 7).

Increased activity is useful for numerous applications, especially when there is a need to analyze samples with low DNA concentrations. Examples of these uses include single-cell genome sequencing, sequencing isolated chromosomes or small genomes, analysis of free DNA from blood, and understanding complex ecological systems. See, e.g., Giorgi et al., PLoS One. 2013; 8(2):e57994. doi: 10.1371/journal.pone.0057994, Fodor et al., PLoS One. 2012; 7(7):e41294. doi: 10.1371). Therefore, a number of adapters were assessed for medium and low DNA inputs.

Experiments were done similarly for the high DNA input except less DNA and less transposase was used in these studies and more PCR amplification cycles were applied. As follows from data represented in FIG. 8A, the best activity with 20 ng input, 11 PCR cycles was obtained with adapter 12. At 1 ng input (B), 15 PCR cycles, the same adapter 12, alongside with adapters 6, 7, 8, and 27, also exhibited significantly higher activity than the parental adapter 1 and other derivative adapters.

Figure 8:
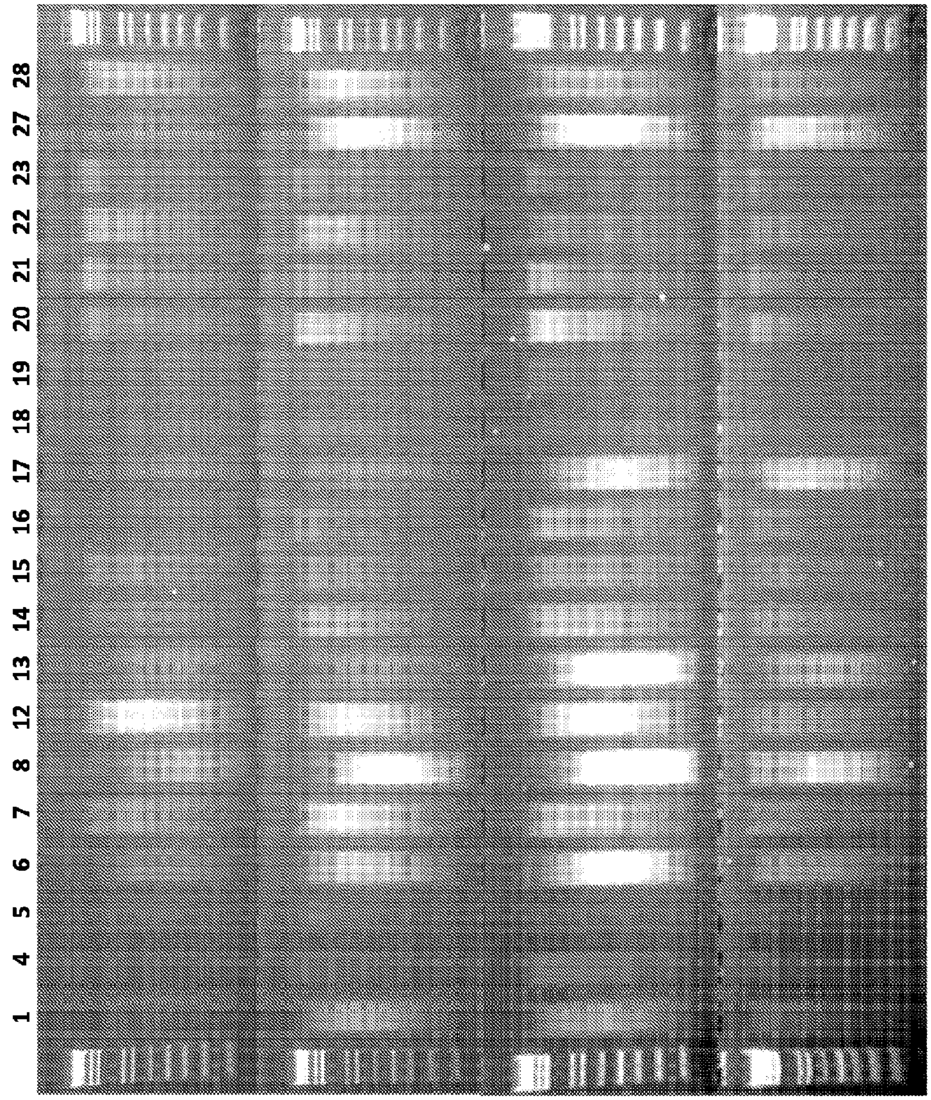
FIGS. 8A, 8B, 8C, and 8D are a set of diagrams showing assessment of activity of plurality of adapters in sample preparation for NGS at medium (A and B) and low (C and D) DNA input. NGS samples generated using Vibhar transposase loaded with different adapters were separated in 2% agarose gels and stained with ethidium bromide.
Figure 9:
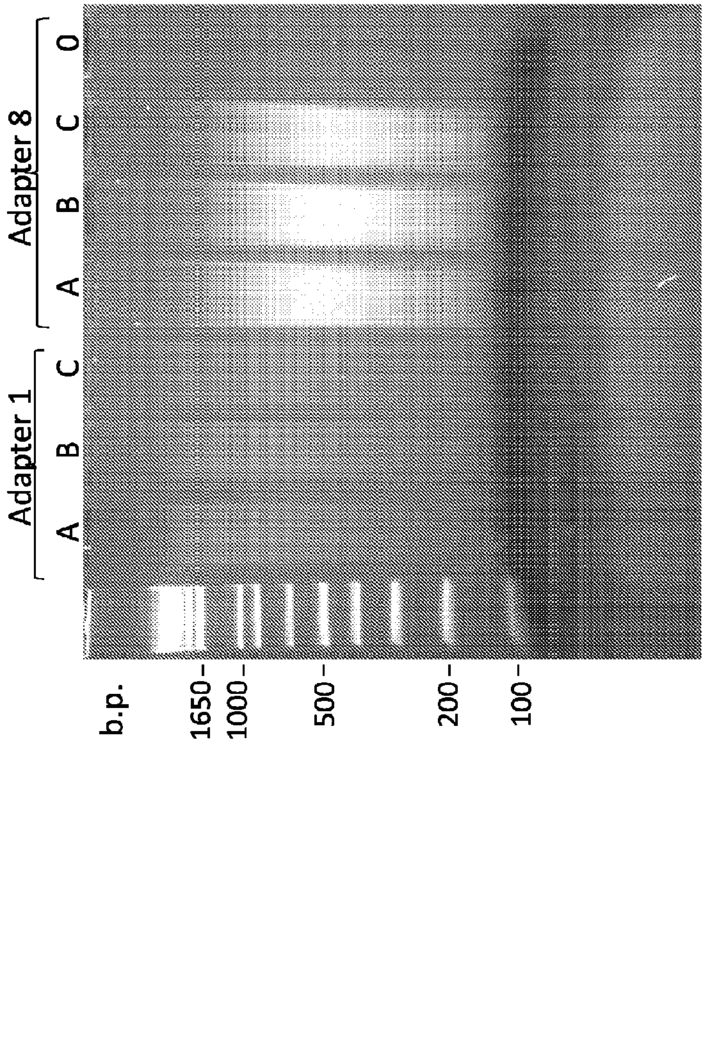
FIG. 9 is a diagram showing confirmation of higher activity conferred to transposase by adapter 8 as compared to the parental adapter 1 at different transposase concentrations (A-5 ug/ml, B-1.7 ug/ml, C-0.56 ug/ml). 0-no transposase negative control. NGS samples generated using Vibhar transposase loaded with different adapters were separated in 2% agarose gels and stained with ethidium bromide.
Figure 10:
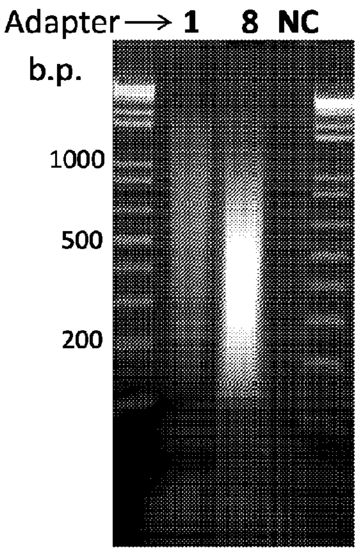
FIG. 10 is a diagram showing confirmation of higher activity conferred to transposase by adapter 8 at low DNA input as compared to the parental adapter 1, as well as no background if DNA was not added (NC). NGS samples generated using Vibhar transposase loaded with different adapters were separated in 2% agarose gels and stained with ethidium bromide.

Similarly, adapters 6, 8, 12, and 27, and in addition adapters 13 and 17 exhibited higher activity at 68 pg DNA input (C), amplification for 19 cycles. Finally, adapters 8, 17 and 27 exhibited the best activity at 4 pg DNA input (D), i.e., less than DNA content of a single human cell. Amplification was performed for 23 cycles. Adapter 8 consistently conferred better yield of DNA fragments than adapter 1 at wide range of loaded transposase concentrations (FIG. 9). Importantly, there was no background from any reagents even at low DNA input of 0.5 pg (about 1/13 DNA content of a diploid human cell) which required 26 PCR cycles (FIG. 10). For comparison, the smallest amount of DNA that is recommended for processing using commercially available kits (Nextera XT DNA Sample Preparation Kits, Illumina, San Diego, Calif.) is 1 ng, or ~150 times more than the DNA content of a human cell. Overall, G to A substitution in position 1 conferred higher activity (adapters 6, 8, 13, 17, and 27), and a combination of G to A substitution and a mismatch in this position further increased the activity in adapters 8 and 27 that comprise C on the opposite strand. Adapters 7 and 12, with native G in position 1, but with a mismatch on the opposite strand also conferred increased activity. Another important aspect is that transposase amount loaded with different adapters work in a certain range of transposase load and target DNA concentrations. For instance, at the conditions of the experiment Vibhar transposase loaded with adapter 12 worked well in the DNA input range 68 ng-20 ng, whereas transposase loaded with adapter 17 worked well at the range 4-68 pg, possessed little activity at 1 ng and was practically inactive at a higher DNA input of 20 ng per 20 μl transposase reaction (FIG. 8). Adapter 13 conferred narrow activity range and worked the best only at 68 pg DNA input.

Example 3 Minimizing Bias in Sample Preparation for NGS

Paired end sequencing (Illumina) and Ion Torrent (Life Sciences) are the most widely used in the NGS platforms. Samples for either platform could be prepared using a transposase method which simultaneously performs DNA fragmentation and attachment of adapters in the same reaction mixture in a few minutes. Yet, as mentioned above, conventional transposase-mediated DNA fragmentation is less random and there is a need for increasing the randomness and decreasing duplication rate.

In this example, it was discovered that different adapters confer different duplication rates. As represented in FIG. 11, adapters 9 and 5 conferred significantly less duplication rate than a standard adapter 1 with native CG pair in the first position; adapters 6 and 8 conferred a higher duplication rate and adapters 7 and 10 conferred about the same duplication rate as the adapter 1. Surprisingly, a mixture of adapters conferred a much lower duplication rate than any of the adapters (FIG. 11).

A possible explanation is that transposase loaded with different adapters is biased to different places on target DNA. These places that are more eagerly recognized by a transposase are called "hot spots" (Berg et al., Genetics. 1983, 105(4):813-28). These hot spots are largely responsible for the duplications as the hot spot areas are sequenced more frequently. However, different adapters confer different hot spots. Since the hot spots differ with different adapters, applying a transposase mixture loaded with different adapters randomizes hot spots and reduces the duplication rate. Furthermore, selecting for the mixture of adapters which individually confer low duplication rate could reduce the duplication rate even further. Transposase loads loaded with different adapters also differ in other properties, e.g., different AT dropout rates (FIG. 12).

Example 4 Impeding Primer Extension for NGS Sample Preparations

In this example, assays were carried out to examine transposase adapters with modifications that impede primer extension for NGS sample preparations.

In one approach, dU modifications, where the Pfu DNA polymerase stalls, were introduced into adapter pairs 2 and 3 as shown in FIG. 13B downstream of the landing sites of PCR primers AgP1 and AgP2 to impede copying of the bottom strand of adapters (oligonucleotides 3U2, 8U2, 3U4 and 8U4) in PCR. While adapter copying and amplification were stalled, amplification of target DNA fragment proceeded unimpeded, as after the gap repair, tagged DNA fragments do not contain modified nucleotides. In another approach, 3' ends of the bottom strands of adapters were blocked with inverted dT so as to impede the primer extension process (see FIG. 13B, adapter pair 4). The inverted dT was preceded by phosphorothioate bond to prevent removal of the inverted dT by DNA polymerase 3' exonuclease activity.

Transposase reactions were carried out in the manner described above and transposase reaction products were directly amplified in PCR using Pfu DNA polymerase (HerculaseII, Agilent Technologies) with AgP1 and AgP2 primers, separated in 2% agarose gels and stained with ethidium bromide, where 1 kb+ DNA ladder (Life Technologies) was run alongside with tested DNA samples.

Figure 14:
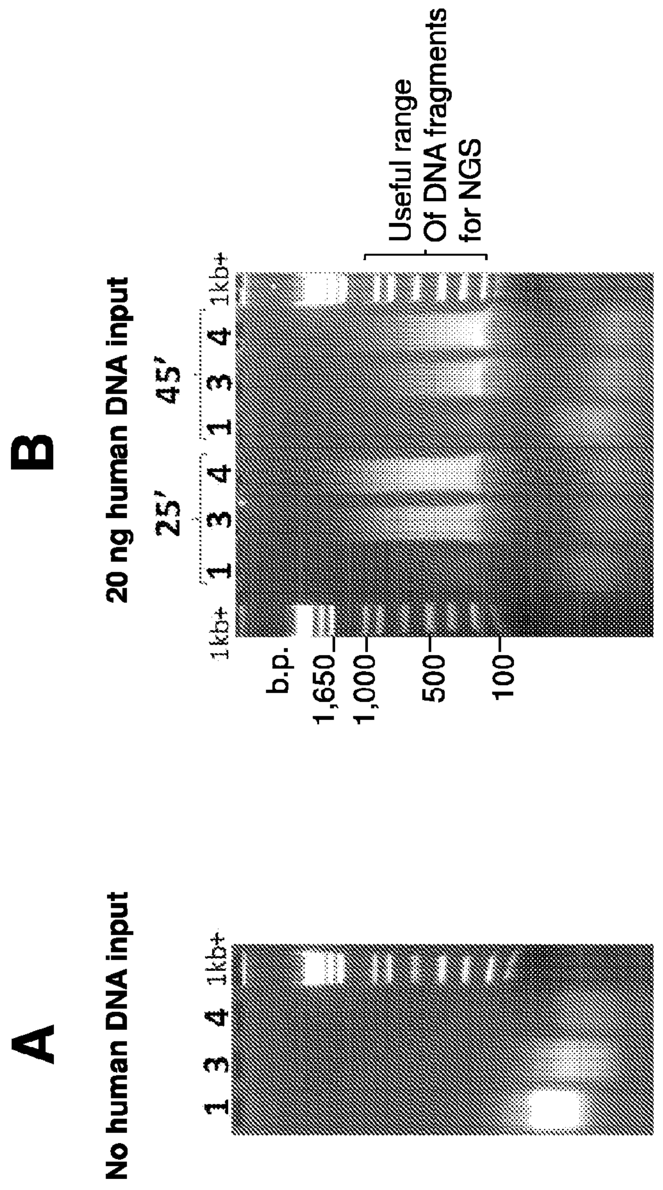
FIGS. 14A and 14B are photographs illustrating amplification of transposase reaction products directly from transposase reaction without SPRI purification: (A) Transposase reaction was performed for 25 min without target DNA, but with Vibhar transposase loaded with adapter pairs 1, 3 or 4; (B) Human DNA (20 ng per 20 ul) was fragmented and tagged in transposase reactions for 20 or 45 min with Vibhar transposase loaded with adapter pairs 1, 3 or 4.

As shown in FIG. 14A, when amplified in PCR using AgP1 and AgP2 primers without target DNA input, transposase reaction with Vibhar transposase loaded with standard adapter pair 1 generated large amounts of small size byproducts. In contrast, generation of these small size byproducts was impeded when adapter pairs 3 and 4 were used. When a medium DNA input (i.e. 20 ng target human DNA and 5 ug of loaded transposase per 20 μl transposase reaction) was used in the transposase reactions, PCR amplification of the reactions using standard transposase adapter pair 1 resulted in practically no useful products. See FIG. 14B. In contrast, adapter pairs 3 or 4 resulted in satisfactory yield of tagged DNA products.

The above results indicate that impeding with either dU or inverted dT reduced production of adapter-primer dimers substantially and led to satisfactory yield of tagged DNA PCR products at a medium DNA input.

Figure 15:
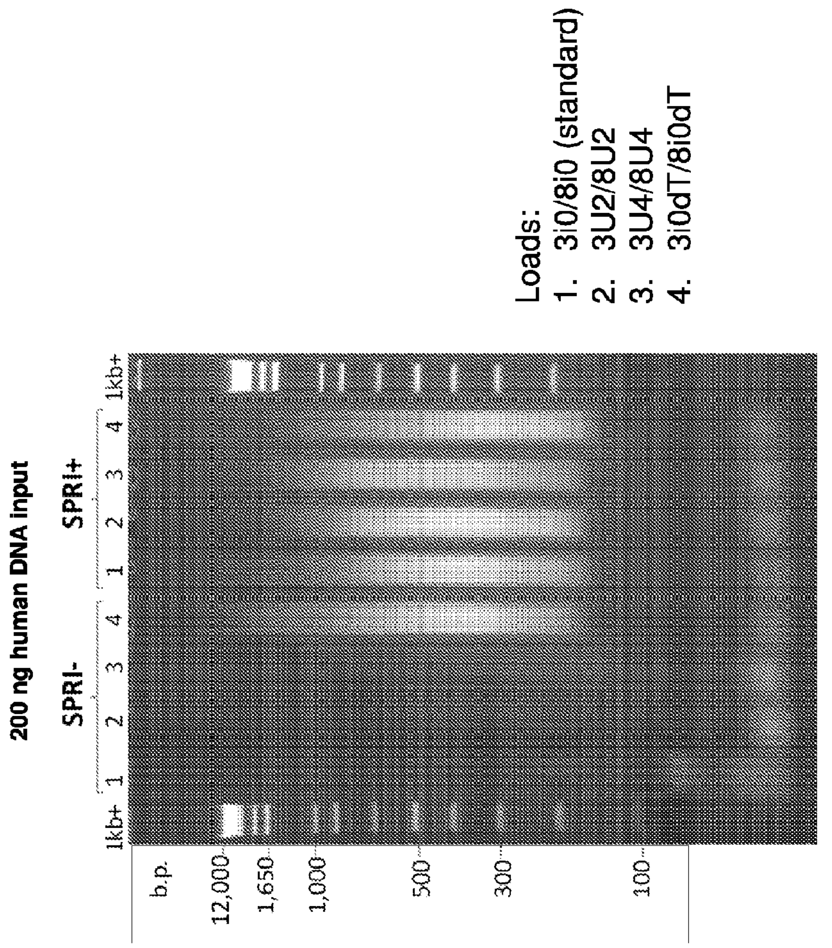
FIG. 15 is a photograph illustrating comparison of PCR products obtained with or without SPRI purification after high target DNA input (200 ng per 20 ul) transposase reactions.
Figure 16:
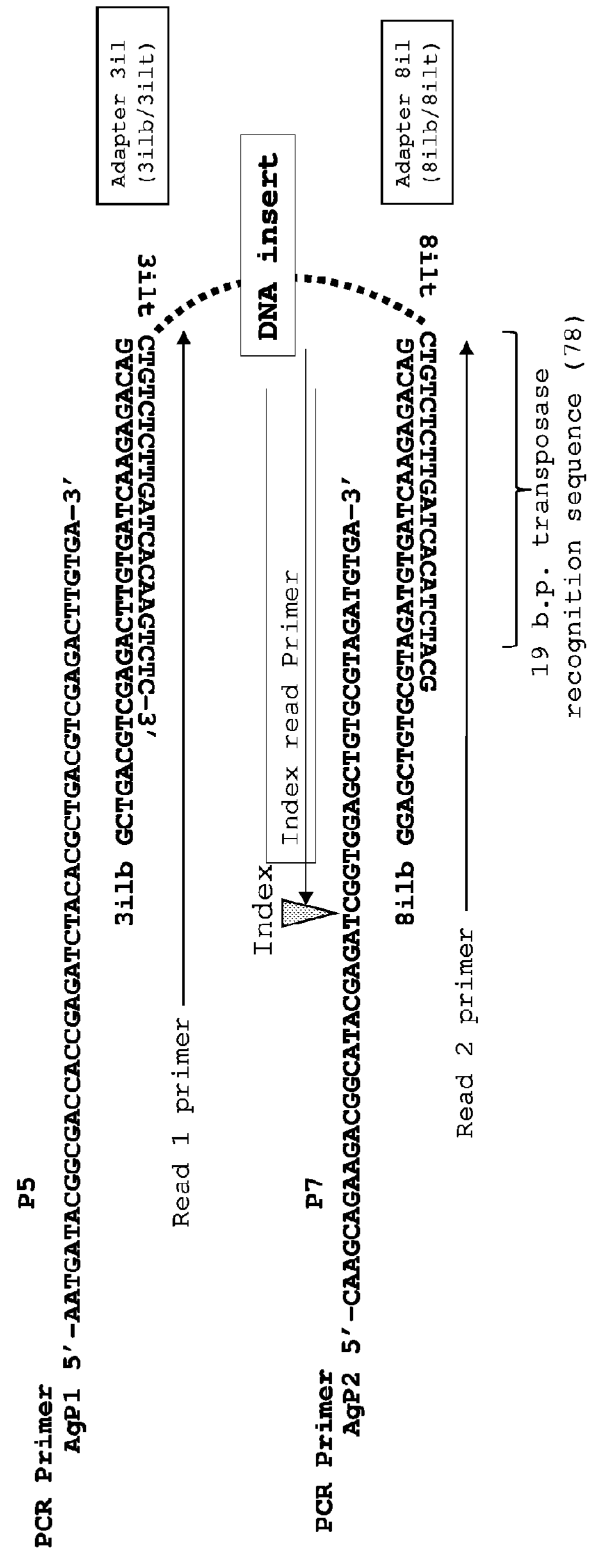
FIG. 16 is a diagram illustrating standard adapters and schematics of sample preparation for NGS, including AgP1, AgP2, 3i1b, 8i1b, 3ilt, and Silt (SEQ ID NOs: 79, 116, 81, 82 and 91-92, respectively). The number 78 in the parenthesis refers to SEQ ID NO: 78. P5 and P7 designate portions necessary for attachment to Illumina flow cell.

The assays were also conducted using a high DNA input (i.e., 200 ng target human DNA and 50 ug of loaded transposase per 20 ul transposase reaction). As shown in FIG. 15, with a high DNA input, amplification of transposase reaction with the same primers again resulted in practically no useful product if standard transposase adapter 1, or adapter pairs 2 or 3 were used. However, the yield of tagged DNA fragments was satisfactory if transposase loaded with adapter pair 4 was used. These results indicate that, at a high DNA input, the impeding capacity of adapter pairs 2 and 3 is less efficient than that of adapter pair 4, and blocking the 3' ends as in adapter pair 4 represents a preferred embodiment.

Importantly, all adapter modifications of this invention are compatible with the transposase reaction. Either modified adapter pairs 2, 3, 4 or unmodified adapter pair 1 generated comparable amounts of target DNA fragments if PCR amplification was performed after the SPRI purification (FIG. 15, SPRI+). Furthermore, with adapter pair 4, yields of these fragments were practically the same with or without SPRI purification (FIG. 15).

In sum, both adapter pairs 3 and 4 were efficient in preventing PCR reaction "poisoning" when less adapters were used in transposase reactions, and consequently less added into PCR (FIG. 14B), but only adapter pair 4 was efficient in preventing PCR "poisoning" with increased target DNA and adapter input (FIG. 15). Given these results, it would be immediately obvious to those skilled in the art how to optimize amounts of loaded transposase contingent upon target DNA input, amount of loaded transposase used in the transposase reaction and on particular adapter modifications.

Example 5 Preparation of DNA Samples for NGS from a Low Number of Cells

In this example, transposase adapters with or without phosphorothioate bonds were used to prepare DNA samples for NGS from a low number of cells.

Briefly, DNA was prepared from 20 pg of human DNA corresponding to DNA material from 3 human cells. The DNA was fragmented and tagged in a transposase reaction with different concentrations of transposase (50 or 100 ng/ml) using standard adapters 3il/8il, which do not have phosphorothioate bonds, and amplified in PCR cycles using AgP1 and AgP2 primers. The PCR fragments were then separated in 2% agarose gels and stained with ethidium bromide. The results are shown in FIG. 17. As shown in the figure, satisfactory yield of suitable DNA fragments was observed after 25 min of transposase reaction with DNA from 3 cells, but the fragments of the desirable size range for NGS (200-500 b.p.) nearly completely disappeared at 42 min of the reaction. The results indicate that even at 25 min of transposase reaction the losses of suitable material could be substantial and may amount to 50% or more, which is unacceptable for NGS application.

The above assays were repeated with Adapter E8 and Adapter 78. These two adapters are identical except that Adapter E8 has phosphorothioate bonds in positions as shown at the top of FIG. 18. The results are shown in FIG. 18.

As shown in the figure, it was unexpected that a combination of phosphorothioate bonds (adapter E8) conferred large improvement in transposase reaction efficiency. Improvement was consistently observed in several experiments at different transposase concentrations (180 ng/ml, 120 ng/ml, and 80 ng/ml with 20 pg human DNA input) as well as at different incubation times (6-70 minutes). It was also found that for the most part this improvement was not due to protection against nucleases. Indeed, practically no nuclease degradation was observed with short adapter 78 that has the same nucleotide sequence, but does not contain phosphorothioate bonds (FIG. 18).

Unlike the standard adapters 3il and 8il (FIG. 16), adapter 78 and its phosphorothioate derivative E8 consist only of 19 b.p. duplex that is recognized by the transposase, bound by the transposase and is likely to be largely hidden and protected from the nuclease attack. It is possible that the nuclease activity recognizes single-strand portion of standard adapters and flips over to the interior of the DNA fragment which it digests. Protein of a substantial size, e.g., transposase dimer (MW~102 KD), would be required for such maneuver. It seems unlikely that indigenous nucleases from *E. coli* are responsible for the DNA degradation as they are small in size; *E. coli* is well studied; and no such activity was described in *E. coli.*

In short, the results indicate that efficiency of transposase reaction was largely improved by adding phosphorothioate bonds to the adapters.

Example 6 Preparation of DNA Samples for Microarray Applications

In this example, transposase adapters with or without phosphorothioate bonds were used to prepare DNA samples for microarray applications. To that end, 16 pg and 200 ng DNAs were subject to the process as shown in FIG. 21A-C.

Initially, the sample DNAs were fragmented using transposase-oligonucleotide complex and tagged at both ends with oligonucleotide tags having phosphorothioate-containing oligonucleotide 5'-A*G*A*T*G*T*G*A*T*CAAGAGACA*G-3' (SEQ ID NO.: 95) in duplex with its phosphodiester complement. Then, at the amplification stage, the fragmented DNA were PCR amplified using primer 7 (5'-AGATGTGATCAAGAGACAG-3', SEQ ID NO.: 93), which was complementary to the tag attached to the ends of DNA fragments in the transposase reaction (FIG. 21B). Here, unlike in conventional protocols and WGA methods, a defined 19 bp primer rather than far less reliable random primer were used (FIG. 21B). Number of PCR cycles depends on the amount of starting DNA. Finally, at the labeling step, the oligonucleotide tags and the primers were used to amplify the DNA fragments in the presence of dNTP mixture comprising at least one dNTP labeled with a fluorophore. This step was carried out in about 10 minutes, which was much faster than random primer-based convention methods.

The resulting DNA fragments along with 1 kb+ DNA ladder (Life Technologies) were separated in 2% agarose gels and stained with ethidium bromide. The results are shown in FIGS. 22A-B. As shown in the figures, fragments with lengths between 200 and 500 bp were routinely produced at DNA inputs ranging from 16 pg to 200 ng, indicating that at the DNA fragmentation stage transposase simultaneously fragmented DNA to the specified size (200-500 bp, which were ideal for arrays) and provided defined 19 bp tags (FIG. 21A). No DNA damage was observed as reaction was performed at about neutral pH, at 45° C. and for a short time. With the transposase method DNA fragments of ideal size were created for Agilent microarrays (Agilent Oligonucleotide Array-Based CGH for Genomic DNA analysis. Protocol version 7.2 July 2012).

It was found that using defined primers, such as primer 7, instead of a random primer of prior art, faster and better quality amplification were achieved. The results indicate that using defined primers allows not only reduction of the amplification bias, but also faster processing of the samples as the reaction conditions are optimal.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. An isolated synthetic nucleic acid adapter comprising a first strand comprising a first sequence; and a second strand comprising a second sequence that is complementary or substantially complementary to the first sequence;

wherein the first sequence or second sequence comprises one or more modifications as compared to a parental recognition sequence for a transposase or the complement thereof, said one or more modifications being selected from the group consisting of the following:

(a) one or more modified nucleotides in the first strand or the first sequence, wherein said one or more modified nucleotides impede a primer extension of said first strand; and (b) one or more phosphorothioate bonds in the second strand or the second sequence, wherein the adapter is recognized by the transposase and the parental recognition sequence is selected from the group consisting of SEQ ID NOs: 1-21, wherein the first strand or the second strand is 17-80 nucleotide in length, and wherein the first sequence and the second sequence comprise, respectively, SEQ ID NOs: 73 and 74, SEQ ID NOs: 75 and 76, SEQ ID NOs: 28 and 36, SEQ ID NOs: 28 and 22, SEQ ID NOs: 2 and 36, SEQ ID NOs: 2 and 74, SEQ ID NOs: 2 and 76, SEQ ID NOs: 26 and 22, SEQ ID NOs: 26 and 36, SEQ ID NOs: 26 and 39, SEQ ID NOs: 26 and 41, SEQ ID NOs: 24 and 22, SEQ ID NOs: 24 and 36, SEQ ID NOs: 24 and 39, SEQ ID NOs: 24 and 41, SEQ ID NOs: 28 and 39, SEQ ID NOs: 28 and 41, SEQ ID NOs: 2 and 39, SEQ ID NOs: 2 and 41, SEQ ID NOs: 75 and 36, or SEQ ID NOs: 73 and 36.

2. The adapter of claim 1, wherein the first sequence has at least one additional nucleotide at its 5' terminus as compared to the parental recognition sequence, or the second sequence has at least one additional nucleotide at its 3' terminus as compared to the complement of the parental recognition sequence.

3. The adapter of claim 1, wherein the first sequence lacks at least one nucleotide at its 5' terminus as compared to the parental recognition sequence, or the second sequence lacks at least one nucleotide at its 3' terminus as compared to the complement of the parental recognition sequence.

4. The adapter of claim 1, wherein said one or more modified nucleotides is selected from the group consisting of a deoxyuridine, an abasic site, a 2'OMe modified ribonucleic acid (RNA), and an inverted thymidine.

5. The adapter of claim 4, wherein the adapter has one or more of the following features:

(i) the inverted thymidine is at the 3' terminus of the first strand, (ii) said one or more modified nucleotides are preceded by a phosphorothioate bond or a spacer, and (iii) the second strand is free of said one or more modified nucleotides.

6. The adapter of claim 1, wherein the adapter has one or more of the following features:

one phosphorothioate bond is between the 3' ultimate nucleotide and the 3' pen-ultimate nucleotide of the second strand or the second sequence, the second strand or the second sequence comprises about 1 to 18, about 2 to 15, or 9 phosphorothioate bonds, and the first strand or the first adaptor sequence is free of phosphorothioate bond.

7. The adapter of claim 1, wherein the adapter further has one or more of the following features:

(a) the first and second strand are 17-80 nucleotides in length, (b) the first strand and the second strand form a duplex that is 15-30 bp in length, (c) the duplex has a blunt end or a staggered end at the 3' terminus of the second strand or the 5' terminus of the first strand, (d) the one or more modifications in the first or second sequence result in one or more unpaired nucleotides in the duplex, (e) the first or second strand comprise at least one modified nucleotide selected from the group consisting of 2-Aminopurine, 2,6-Diaminopurine, 5-Bromo dU, deoxyUridine, inverted dT, inverted Dideoxy-T, dideoxy-C, 5-Methyl dC, deoxyInosine, a universal base comprising 5-Nitroindole, a 2'-O-Methyl RNA base, iso-dC, iso-dG, ribonucleotide, morpholino, a protein nucleitide analogue, a glycoic nucleotide analogue, a locked nucleotide analogue, a threose nucleotide analogue, a chain terminating nucleotide analogue, thiouridine, pseudouridine, dihydrouridine, queuosine, and wyosine, (f) at least one nucleotide in the first or second strand is phosphorylated, (g) at least one nucleotide in the first or second strand comprises one or more selected from the group consisting of a modified sugar, a unnatural bond, an abasic site, a dideoxy base, a 5-methyl base, and a spacer, (h) at least one nucleotide in the first or second strand is a ribonucleotide, (i) the transposase is a “cut and paste” transposase, (j) the transposase is *Vibrio Harveyi* transposase or hyperactive Tn5 transposase, (k) the second strand further comprises a tag sequence 5' to the second sequence or the first strand further comprises a tag sequence 3' to the first sequence, and (l) the tag sequence comprises a degenerate base region.

8. A set of isolated synthetic nucleic acid adapters, comprising (i) a first adapter, and (ii) a second adapter, each being an adapter of claim 1, wherein the first adapter and the second adapter have at least one different modification as compared to the parental recognition sequence or the complement thereof.

9. A transposase complex comprising one or more transposase molecules and one or more adapters according to claim 1.

10. An in vitro method for fragmenting a target DNA molecule, comprising: contacting a target DNA molecule with a transposase complex of claim 9 to form a reaction mixture; and incubating the reaction mixture under conditions for carrying out a transposition reaction.

11. The method of claim 10, wherein the target DNA molecule is obtained from a sample consisting of 1-10 cells.

12. The method of claim 11, wherein the target DNA molecule is obtained from a sample consisting of 1-3 cells.

13. A method for preparing an assay sample for sequencing or microarray analysis of a target DNA molecule, comprising:

contacting a target DNA molecule with a complex having an isolated synthetic nucleic acid adapter of claim 1 and a transposase that binds to the adapter to form a reaction mixture;

incubating the reaction mixture under conditions for carrying out a transposition reaction to generate a cleaved DNA product, and amplifying the cleaved DNA product.

14. The method of claim 13, wherein the amplifying step is conducted without prior removing of the adaptor or separating the cleaved DNA product from the reaction mixture.

15. A method of DNA sample preparation for microarrays, comprising contacting a sample DNA molecule with a complex having an isolated synthetic nucleic acid adapter of claim 1 and a transposase that binds to the adapter to form a reaction mixture; and incubating the reaction mixture under conditions for carrying out a transposition reaction to generate DNA fragments of the sample DNA molecule, wherein said adapter comprises an oligonucleotide tag and the DNA fragments are tagged at both ends with the oligonucleotide tag.

16. The method of claim 15, further comprising amplifying the DNA fragments using primers complementary to the oligonucleotide tag.

17. The method of claim 15, wherein said tag is used as a landing site for a primer complementary to the tag.

18. The method of claim 16, wherein the primer or primers are extended in polymerase reaction using dNTP mixture comprising at least one dNTP labeled with a fluorophore.

* * * * *

SEQUENCE LISTING

```
<160> NUMBER OF SEQ ID NOS: 132

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ctgtctctta tacacaaat                                                  19


<210> SEQ ID NO 2
<211> LENGTH: 19
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 2
ctgtctcttg atcacaagt 19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
ctgtctcttg atcacatct 19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
ctgactctta tacacaagt 19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
ctgtctcttg atcagatct 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
ctgtctctta tacacatct 19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
ctgtctctta tacagaaaa 19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 8
ctgaatcttc tacacatct 19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
catactctta tacataagt 19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
cataggtatc tacacaaaa 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
cataggtatc tacacagat 19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
catccgattg cacacatct 19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
cataggtatc tacacaatt 19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
cataggtatc tacacaaaa 19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
cataggtatc tacacatct 19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
catctcgtta tacacaact 19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
catgtcgtta tacacaact 19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
ctactgtgta cacacaagt 19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
cattagtgtc ccgttaaaa 19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
cactactgtc ccgtaaaag 19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
cattactgtc ccgtaaaag 19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
acttgtgatc aagagacag 19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
acttgtgatc aagagacah 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
atgtctcttg atcacaagt 19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
acttgtgatc aagagacav 19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gtgtctcttg atcacaagt 19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
acttgtgatc aagagacad 19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
ttgtctcttg atcacaagt 19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
acttgtgatc aagagacab 19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, t or g

<400> SEQUENCE: 30
nntgtctctt gatcacaagt 20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: a, c, t or g

<400> SEQUENCE: 31
acttgtgatc aagagacan 19

<210> SEQ ID NO 32
<211> LENGTH: 19

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t or g

<400> SEQUENCE: 32
ntgtctcttg atcacaagt 19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(20)
<223> OTHER INFORMATION: a, c, t or g

<400> SEQUENCE: 33
acttgtgatc aagagacann 20

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
dtgtctcttg atcacaagt 19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
vtgtctcttg atcacaagt 19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
acttgtgatc aagagacaa 19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (2)..(2)
<223> OTHER INFORMATION: a, c, t or g

<400> SEQUENCE: 37
nntgtctctt gatcacaagt 20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
btgtctcttg atcacaagt 19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
acttgtgatc aagagacat 19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
htgtctcttg atcacaagt 19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
acttgtgatc aagagacac 19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
tgtctcttga tcacaagt 18

<210> SEQ ID NO 43

-continued

<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
acttgtgatc aagagaca 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
tgtctcttga tcacaagt 18

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 45
ntgtctcttg atcacaagt 19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: a, c, t, g, unknown or other

<400> SEQUENCE: 46
acttgtgatc aagagacan 19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: a, c, t or g
<220> FEATURE:
<221> NAME/KEY: modified_base
<222> LOCATION: (20)..(20)
<223> OTHER INFORMATION: a, c, t, g, unknown or other

<400> SEQUENCE: 47
acttgtgatc aagagacann 20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
agatgtgtat aagagacag 19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
agatgtgtat aagagacah 19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
atgtctctta tacacatct 19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
agatgtgtat aagagacav 19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
gtgtctctta tacacatct 19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
agatgtgtat aagagacad 19

-continued

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
ttgtctctta tacacatct 19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
agatgtgtat aagagacab 19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, t or g

<400> SEQUENCE: 56
nntgtctctt atacacatct 20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: a, c, t or g

<400> SEQUENCE: 57
agatgtgtat aagagacan 19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: a, c, t or g

<400> SEQUENCE: 58
ntgtctctta tacacatct 19

<210> SEQ ID NO 59
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, t or g

<400> SEQUENCE: 59

agatgtgtat aagagacann                                          20


<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

dtgtctctta tacacatct                                           19


<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

vtgtctctta tacacatct                                           19


<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

agatgtgtat aagagacaa                                           19


<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

btgtctctta tacacatct                                           19


<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

agatgtgtat aagagacat                                           19
```

-continued

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
htgtctctta tacacatct 19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
agatgtgtat aagagacac 19

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
tgtctcttat acacatct 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
agatgtgtat aagagaca 18

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 69
ntgtctctta tacacatct 19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: a, c, t, g, unknown or other

<400> SEQUENCE: 70
agatgtgtat aagagacan 19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (2)..(2)
<223> OTHER INFORMATION: a, c, t or g

<400> SEQUENCE: 71
nntgtctctt atacacatct 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: a, c, t or g
<220> FEATURE:
<221> NAME/KEY: modified_base
<222> LOCATION: (20)..(20)
<223> OTHER INFORMATION: a, c, t, g, unknown or other

<400> SEQUENCE: 72
agatgtgtat aagagacann 20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
tctgtctctt gatcacaagt 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
acttgtgatc aagagacaga 20

<210> SEQ ID NO 75
<211> LENGTH: 20
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 75
actgtctctt gatcacaagt 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
acttgtgatc aagagacagt 20

<210> SEQ ID NO 77
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
aatgatacgg cgaccaccga gatctacacg ctgacgtcga gacttgtga 49

<210> SEQ ID NO 78
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
caagcagaag acggcatacg agatcggtgg agctgtgcgt agatgtga 48

<210> SEQ ID NO 79
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
aatgatacgg cgaccaccga gatctacacg ctgacgtcga gacttgtga 49

<210> SEQ ID NO 80
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (25)..(30)
<223> OTHER INFORMATION: a, c, t, g, unknown or other

<400> SEQUENCE: 80
caagcagaag acggcatacg agatnnnnnn cggtggagct gtgcgtagat gtga 54

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
gctgacgtcg agacttgtga tcaagagaca g 31

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
ggagctgtgc gtagatgtga tcaagagaca g 31

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
ctgtctcttg atcacaagt 19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
ctgtctcttg atcacatct 19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 85
ctgtctctug aucacaagt 19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 86
ctgtctctug aucacatct 19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 87
ctgtcucuug aucacaagt 19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 88
ctgtcucuug aucacatct 19

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(20)
<223> OTHER INFORMATION: Phosphorothioate bond between nucleotides
<220> FEATURE:
<221> NAME/KEY: modified_base
<222> LOCATION: (20)..(20)
<223> OTHER INFORMATION: Inverted thymidine

<400> SEQUENCE: 89
ctgtctcttg atcacaagtt 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(20)
<223> OTHER INFORMATION: Phosphorothioate bond between nucleotides
<220> FEATURE:
<221> NAME/KEY: modified_base
<222> LOCATION: (20)..(20)
<223> OTHER INFORMATION: Inverted thymidine

<400> SEQUENCE: 90
ctgtctcttg atcacatctt 20

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctgtctcttg atcacaagtc tc 22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctgtctcttg atcacatcta cg 22

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agatgtgatc aagagacag 19

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctgtctcttg atcacatct 19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: Phosphorothioate bond between nucleotides
<220> FEATURE:
<221> NAME/KEY: misc_feature
<222> LOCATION: (18)..(19)
<223> OTHER INFORMATION: Phosphorothioate bond between nucleotides

<400> SEQUENCE: 95
agatgtgatc aagagacag 19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(3)
<223> OTHER INFORMATION: Phosphorothioate bond between nucleotides
<220> FEATURE:
<221> NAME/KEY: misc_feature
<222> LOCATION: (18)..(19)
<223> OTHER INFORMATION: Phosphorothioate bond between nucleotides

<400> SEQUENCE: 96
agatgtgatc aagagacag 19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
ctgtctcttg atcacatct 19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(10)
<223> OTHER INFORMATION: Phosphorothioate bond between nucleotides
<220> FEATURE:
<221> NAME/KEY: misc_feature
<222> LOCATION: (18)..(19)
<223> OTHER INFORMATION: Phosphorothioate bond between nucleotides

<400> SEQUENCE: 98
agatgtgatc aagagacag 19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: Phosphorothioate bond between nucleotides

<400> SEQUENCE: 99
ctgtctcttg atcacatct 19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(10)
<223> OTHER INFORMATION: Phosphorothioate bond between nucleotides

<400> SEQUENCE: 100
agatgtgatc aagagacag 19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(11)
<223> OTHER INFORMATION: Phosphorothioate bond between nucleotides
<220> FEATURE:
<221> NAME/KEY: misc_feature
<222> LOCATION: (17)..(19)
<223> OTHER INFORMATION: Phosphorothioate bond between nucleotides

<400> SEQUENCE: 101
agatgtgatc aagagacag 19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(11)
<223> OTHER INFORMATION: Phosphorothioate bond between nucleotides
<220> FEATURE:
<221> NAME/KEY: misc_feature
<222> LOCATION: (16)..(19)
<223> OTHER INFORMATION: Phosphorothioate bond between nucleotides

<400> SEQUENCE: 102
agatgtgatc aagagacag 19

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(12)
<223> OTHER INFORMATION: Phosphorothioate bond between nucleotides
<220> FEATURE:
<221> NAME/KEY: misc_feature
<222> LOCATION: (14)..(15)
<223> OTHER INFORMATION: Phosphorothioate bond between nucleotides
<220> FEATURE:
<221> NAME/KEY: misc_feature
<222> LOCATION: (17)..(19)
<223> OTHER INFORMATION: Phosphorothioate bond between nucleotides

<400> SEQUENCE: 103
agatgtgatc aagagacag 19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<221> NAME/KEY: misc_feature
<222> LOCATION: (1)..(12)
<223> OTHER INFORMATION: Phosphorothioate bond between nucleotides
<220> FEATURE:
<221> NAME/KEY: misc_feature
<222> LOCATION: (13)..(14)
<223> OTHER INFORMATION: Phosphorothioate bond between nucleotides
<220> FEATURE:
<221> NAME/KEY: misc_feature
<222> LOCATION: (15)..(16)
<223> OTHER INFORMATION: Phosphorothioate bond between nucleotides
<220> FEATURE:
<221> NAME/KEY: misc_feature
<222> LOCATION: (17)..(19)
<223> OTHER INFORMATION: Phosphorothioate bond between nucleotides

<400> SEQUENCE: 104
agatgtgatc aagagacag 19

<210> SEQ ID NO 105
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(15)
<223> OTHER INFORMATION: Phosphorothioate bond between nucleotides
<220> FEATURE:
<221> NAME/KEY: misc_feature
<222> LOCATION: (30)..(31)
<223> OTHER INFORMATION: Phosphorothioate bond between nucleotides

<400> SEQUENCE: 105
ggagctgtgc gtagatgtga tcaagagaca g 31

<210> SEQ ID NO 106
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(15)
<223> OTHER INFORMATION: Phosphorothioate bond between nucleotides
<220> FEATURE:
<221> NAME/KEY: misc_feature
<222> LOCATION: (30)..(31)
<223> OTHER INFORMATION: Phosphorothioate bond between nucleotides

<400> SEQUENCE: 106
gctgacgtcg agacttgtga tcaagagaca g 31

<210> SEQ ID NO 107
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(3)
<223> OTHER INFORMATION: Phosphorothioate bond between nucleotides
<220> FEATURE:
<221> NAME/KEY: misc_feature
<222> LOCATION: (30)..(31)
<223> OTHER INFORMATION: Phosphorothioate bond between nucleotides

<400> SEQUENCE: 107
ggagctgtgc gtagatgtga tcaagagaca g 31

<210> SEQ ID NO 108
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(3)
<223> OTHER INFORMATION: Phosphorothioate bond between nucleotides
<220> FEATURE:
<221> NAME/KEY: misc_feature
<222> LOCATION: (30)..(31)
<223> OTHER INFORMATION: Phosphorothioate bond between nucleotides

<400> SEQUENCE: 108
gctgacgtcg agacttgtga tcaagagaca g 31

<210> SEQ ID NO 109
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(3)
<223> OTHER INFORMATION: Phosphorothioate bond between nucleotides
<220> FEATURE:
<221> NAME/KEY: misc_feature
<222> LOCATION: (13)..(15)
<223> OTHER INFORMATION: Phosphorothioate bond between nucleotides
<220> FEATURE:
<221> NAME/KEY: misc_feature
<222> LOCATION: (30)..(31)
<223> OTHER INFORMATION: Phosphorothioate bond between nucleotides

<400> SEQUENCE: 109
ggagctgtgc gtagatgtga tcaagagaca g 31

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(3)
<223> OTHER INFORMATION: Phosphorothioate bond between nucleotides
<220> FEATURE:
<221> NAME/KEY: misc_feature
<222> LOCATION: (13)..(15)
<223> OTHER INFORMATION: Phosphorothioate bond between nucleotides
<220> FEATURE:
<221> NAME/KEY: misc_feature
<222> LOCATION: (30)..(31)
<223> OTHER INFORMATION: Phosphorothioate bond between nucleotides

<400> SEQUENCE: 110
gctgacgtcg agacttgtga tcaagagaca g 31

<210> SEQ ID NO 111
<211> LENGTH: 19
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(10)
<223> OTHER INFORMATION: Phosphorothioate bond between nucleotides

<400> SEQUENCE: 111
agatgtgatc aagagacaa 19

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(10)
<223> OTHER INFORMATION: Phosphorothioate bond between nucleotides
<220> FEATURE:
<221> NAME/KEY: misc_feature
<222> LOCATION: (18)..(19)
<223> OTHER INFORMATION: Phosphorothioate bond between nucleotides

<400> SEQUENCE: 112
agatgtgatc aagagacaa 19

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(10)
<223> OTHER INFORMATION: Phosphorothioate bond between nucleotides
<220> FEATURE:
<221> NAME/KEY: misc_feature
<222> LOCATION: (18)..(19)
<223> OTHER INFORMATION: Phosphorothioate bond between nucleotides

<400> SEQUENCE: 113
agatgtgatc aagagacag 19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(20)
<223> OTHER INFORMATION: Phosphorothioate bond between nucleotides
<220> FEATURE:
<221> NAME/KEY: modified_base
<222> LOCATION: (20)..(20)
<223> OTHER INFORMATION: Inverted thymidine

<400> SEQUENCE: 114
ctgtctcttg atcacatctt 20

<210> SEQ ID NO 115
<211> LENGTH: 19

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: Phosphorothioate bond between nucleotides
<220> FEATURE:
<221> NAME/KEY: misc_feature
<222> LOCATION: (18)..(19)
<223> OTHER INFORMATION: Phosphorothioate bond between nucleotides

<400> SEQUENCE: 115

agatgtgatc aagagacaa                                                19


<210> SEQ ID NO 116
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

caagcagaag acggcatacg agatcggtgg agctgtgcgt agatgtga                48


<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule: Synthetic
      oligonucleotide
<220> FEATURE:
<221> NAME/KEY: misc_feature
<222> LOCATION: (19)..(20)
<223> OTHER INFORMATION: Phosphorothioate bond between nucleotides
<220> FEATURE:
<221> NAME/KEY: modified_base
<222> LOCATION: (20)..(20)
<223> OTHER INFORMATION: Inverted thymidine

<400> SEQUENCE: 117

ctgtcucuug aucacatctt                                               20


<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule: Synthetic
      oligonucleotide

<400> SEQUENCE: 118

ctgtcucuug aucacatct                                                19


<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 119
aatgatacgg cgaccaccga gatcacacgc tgacgtcgat ga 42

<210> SEQ ID NO 120
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
caagcagaag acggcatacg agatcggtgg agctgtgcgt aga 43

<210> SEQ ID NO 121
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
acacgctgac gtcgatgaga tgtgatcaag agacag 36

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
cggtggagct gtgcgtagat gtgatcaaga gacag 35

<210> SEQ ID NO 123
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
caagcagaag acggcatacg agatcgtgat cggtggagct gtgcgtaga 49

<210> SEQ ID NO 124
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
caagcagaag acggcatacg agatacatcg cggtggagct gtgcgtaga 49

<210> SEQ ID NO 125
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
caagcagaag acggcatacg agatgcctaa cggtggagct gtgcgtaga 49

<210> SEQ ID NO 126
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
caagcagaag acggcatacg agattggtca cggtggagct gtgcgtaga 49

<210> SEQ ID NO 127
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
caagcagaag acggcatacg agatcactgt cggtggagct gtgcgtaga 49

<210> SEQ ID NO 128
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
caagcagaag acggcatacg agatattggc cggtggagct gtgcgtaga 49

<210> SEQ ID NO 129
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
caagcagaag acggcatacg agatgatctg cggtggagct gtgcgtaga 49

<210> SEQ ID NO 130
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
caagcagaag acggcatacg agattcaagt cggtggagct gtgcgtaga 49

<210> SEQ ID NO 131
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131

-continued caagcagaag acggcatacg agatctgatc cggtggagct gtgcgtaga 49

<210> SEQ ID NO 132
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132
caagcagaag acggcatacg agataagcta cggtggagct gtgcgtaga 49

UNITED STATES PATENT AND TRADEMARK OFFICE
CERTIFICATE OF CORRECTION

PATENT NO. : 10,287,622 B2
APPLICATION NO. : 15/035038
DATED : May 14, 2019
INVENTOR(S) : Alexander S. Belyaev Page 1 of 2

It is certified that error appears in the above-identified patent and that said Letters Patent is hereby corrected as shown below:

In the Drawings

On Sheet 3 of 22, in Figure 3, Line 19, delete "nucleitide" and insert -- nucleotide --, therefor.

On Sheet 3 of 22, in Figure 3, Line 19, delete "Glycoic" and insert -- Glycolic --, therefor.

In the Specification

In Column 3, Line 33, delete "nucleitide" and insert -- nucleotide --, therefor.

In Column 3, Line 34, delete "glycoic" and insert -- glycolic --, therefor.

In Column 5, Line 61, delete "NOs." and insert -- NOs, --, therefor.

In Column 5, Line 62, after "72" insert -- , --.

In Column 7, Line 7, delete "3i1b, 8i1b," and insert -- 3ilb, 8ilb, --, therefor.

In Column 13, Line 18, after "20120301925" insert -- . --.

In Column 15, Line 25, delete "(eQLTs)." and insert -- (eQTLs). --, therefor.

In Column 15, Line 55, delete "trofectoderm" and insert -- trophectoderm --, therefor.

In Column 17, Line 4, delete "nucleitide" and insert -- nucleotide --, therefor.

In Column 17, Line 4, delete "Glycoic" and insert -- Glycolic --, therefor.

In Column 27, Line 54, delete "Pollonator" and insert -- Pollinator --, therefor.

Signed and Sealed this
Tenth Day of September, 2019

Andrei Iancu
*Director of the United States Patent and Trademark Office*

CERTIFICATE OF CORRECTION (continued)
U.S. Pat. No. 10,287,622 B2

In Column 31, Line 37, after "preparation" insert -- . --.

In Column 31, Line 45, after "used" insert -- . --.

In Column 31, Lines 59-60, after "performance" insert -- . --.

In Column 43, Line 39, delete "FIG." and insert -- FIGS. --, therefor.

In the Claims

In Column 96, Line 52, in Claim 7, delete "nucleitide" and insert -- nucleotide --, therefor.

In Column 96, Line 52, in Claim 7, delete "glycoic" and insert -- glycolic --, therefor.